US011965194B2

(12) United States Patent
Liang et al.

(10) Patent No.: US 11,965,194 B2
(45) Date of Patent: *Apr. 23, 2024

(54) KETOREDUCTASE POLYPEPTIDES FOR THE PRODUCTION OF (R)-3-HYDROXYTHIOLANE

(71) Applicant: Codexis, Inc., Redwood City, CA (US)

(72) Inventors: Jack S. Liang, South San Francisco, CA (US); Stephan Jenne, Foster City, CA (US); Emily Mundorff, Garden City, NY (US); Rama Voladri, Pleasanton, CA (US); James J. Lalonde, San Mateo, CA (US); Gjalt W. Huisman, Redwood City, CA (US)

(73) Assignee: Codexis, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/813,950

(22) Filed: Jul. 21, 2022

(65) Prior Publication Data

US 2023/0068040 A1    Mar. 2, 2023

Related U.S. Application Data

(60) Continuation of application No. 17/080,676, filed on Oct. 26, 2020, now Pat. No. 11,427,841, which is a continuation of application No. 16/457,396, filed on Jun. 28, 2019, now Pat. No. 10,851,397, which is a continuation of application No. 15/902,301, filed on Feb. 22, 2018, now Pat. No. 10,385,371, which is a continuation of application No. 15/184,018, filed on Jun. 16, 2016, now Pat. No. 9,932,615, which is a continuation of application No. 14/597,996, filed on Jan. 15, 2015, now Pat. No. 9,394,552, which is a continuation of application No. 13/525,048, filed on Jun. 15, 2012, now Pat. No. 8,962,285, which is a continuation of application No. 13/110,789, filed on May 18, 2011, now Pat. No. 8,227,229, which is a division of application No. 12/197,286, filed on Aug. 24, 2008, now Pat. No. 7,977,078.

(60) Provisional application No. 60/957,974, filed on Aug. 24, 2007.

(51) Int. Cl.
*C12P 17/00* (2006.01)
*C12N 9/04* (2006.01)
*C12P 17/16* (2006.01)

(52) U.S. Cl.
CPC ............ *C12P 17/00* (2013.01); *C12N 9/0006* (2013.01); *C12P 17/167* (2013.01); *C12Y 101/01184* (2013.01); *Y02P 20/52* (2015.11)

(58) Field of Classification Search
CPC ...... C12P 17/00; C12P 17/167; C12N 9/0006; C12Y 101/01184; Y02P 20/52
See application file for complete search history.

(56) References Cited

U.S. PATENT DOCUMENTS

| | | |
|---|---|---|
| 4,443,373 A | 4/1984 | Girijavallabhan et al. |
| 4,530,793 A | 7/1985 | Girijavallabhan et al. |
| 4,619,924 A | 10/1986 | Hamanaka |
| 4,695,626 A | 9/1987 | Brighty |
| 4,739,047 A | 4/1988 | Volkmann et al. |
| 4,864,046 A | 9/1989 | Volkmann |
| 4,874,877 A | 10/1989 | Urban |
| 4,940,823 A | 7/1990 | Volkmann |
| 4,954,647 A | 9/1990 | Urban |
| 5,013,729 A | 5/1991 | Volkmann |
| 5,191,077 A | 3/1993 | Volkmann |
| 5,200,335 A | 4/1993 | Hummel et al. |
| 5,206,399 A | 4/1993 | Sayo et al. |
| 5,225,339 A | 7/1993 | Wong et al. |
| 5,319,103 A | 6/1994 | Volkmann |
| 5,326,884 A | 7/1994 | Urban |
| 5,342,767 A | 8/1994 | Wong et al. |
| 5,427,933 A | 6/1995 | Chen et al. |
| 5,491,077 A | 2/1996 | Chartrain et al. |
| 5,559,030 A | 9/1996 | Matsuyama et al. |
| 5,700,670 A | 12/1997 | Yamagishi et al. |
| 5,891,685 A | 4/1999 | Yamagishi et al. |
| 6,037,158 A | 3/2000 | Hummel et al. |
| 6,225,099 B1 | 5/2001 | Hummel et al. |
| 6,399,339 B1 | 6/2002 | Wolberg et al. |
| 6,413,750 B1 | 7/2002 | Hummel et al. |
| 6,645,746 B1 | 11/2003 | Kizaki et al. |
| 6,689,591 B2 | 2/2004 | Muller et al. |

(Continued)

FOREIGN PATENT DOCUMENTS

| | | |
|---|---|---|
| EP | 1323830 A2 | 7/2003 |
| EP | 1582518 A1 | 10/2005 |

(Continued)

OTHER PUBLICATIONS

Amidjojo et al., 2005, "Asymmetric Synthesis of Tert-butyl (3R, 5S)6-chloro-dihydroxyhexanoate with *Lactobacillus kefir*," *Appl Microbiol Biotechnol.*, 69:9-15.
Bisel et al., 2007, "Stereochemical clarification of the enzyme-catalysed reduction of 2-acetylchromen-4-one," *Tetrahedron Asymmetry*, 18(9):1142-1144.
Bradshaw et al., 1992, "*Lactobacillus kefir* Alcohol Dehydrogenase: A Useful Catalyst for Synthesis," *J. Org. Chem.* 57(5):1532-1536.
Breyer-Pfaff et al., 1999, "High-affinity Stereoselective Reduction of the Enantiomers of Ketotifen and of Ketonic Nortriptyline Metabolites by Aldo-Keto Reductases from Human Liver," *Biochem. Pharmacol.*, 59:249-260.

(Continued)

*Primary Examiner* — Ganapathirama Raghu

(57) ABSTRACT

The present disclosure provides engineered ketoreductase enzymes having improved properties as compared to a naturally occurring wild-type ketoreductase enzyme. Also provided are polynucleotides encoding the engineered ketoreductase enzymes, host cells capable of expressing the engineered ketoreductase enzymes, and methods of using the engineered ketoreductase enzymes to synthesize chiral compounds.

19 Claims, 1 Drawing Sheet

Specification includes a Sequence Listing.

(56) References Cited

U.S. PATENT DOCUMENTS

| | | | |
|---|---|---|---|
| 6,800,477 B2 | 10/2004 | Patel et al. | |
| 7,052,885 B2 | 5/2006 | Poechlauer et al. | |
| 7,083,962 B2 | 8/2006 | Kimoto et al. | |
| 7,820,421 B2 | 10/2010 | Ching et al. | |
| 7,883,879 B2 | 2/2011 | Campopiano et al. | |
| 7,977,078 B2 | 7/2011 | Liang et al. | |
| 8,071,347 B2 | 12/2011 | Ching et al. | |
| 8,088,610 B2 | 1/2012 | Liang et al. | |
| 8,227,229 B2 | 7/2012 | Liang et al. | |
| 8,257,952 B2 | 9/2012 | Campopiano et al. | |
| 8,273,554 B2 | 9/2012 | Mundorff et al. | |
| 8,288,131 B2 | 10/2012 | Voladri et al. | |
| 8,415,126 B2 | 4/2013 | Mundorff et al. | |
| 8,415,127 B2 | 4/2013 | Ching et al. | |
| 8,455,230 B2 | 6/2013 | Voladri et al. | |
| 8,470,572 B2 | 6/2013 | Campopiano et al. | |
| 8,512,973 B2 | 8/2013 | Liang et al. | |
| 8,617,853 B2 | 12/2013 | Liang et al. | |
| 8,748,143 B2 | 6/2014 | Liang et al. | |
| 8,852,909 B2 | 10/2014 | Liang et al. | |
| 8,962,285 B2 | 2/2015 | Liang et al. | |
| 9,394,552 B2 | 7/2016 | Liang et al. | |
| 9,932,615 B2 | 4/2018 | Liang et al. | |
| 10,385,371 B2 | 8/2019 | Liang et al. | |
| 10,851,397 B2 | 12/2020 | Liang et al. | |
| 11,427,841 B2 * | 8/2022 | Liang | C12Y 101/01184 |
| 2002/0061564 A1 | 5/2002 | Rozzell | |
| 2003/0054520 A1 | 3/2003 | Bommanus et al. | |
| 2003/0068811 A1 | 4/2003 | Patel et al. | |
| 2004/0265978 A1 | 12/2004 | Gupta et al. | |
| 2006/0195947 A1 | 8/2006 | Davis et al. | |
| 2006/0286646 A1 | 12/2006 | Patel et al. | |
| 2008/0248539 A1 | 10/2008 | Giver et al. | |
| 2008/0318295 A1 | 12/2008 | Ching et al. | |
| 2009/0155863 A1 | 6/2009 | Liang et al. | |
| 2009/0162909 A1 | 6/2009 | Campopiano et al. | |
| 2009/0191605 A1 | 7/2009 | Liang et al. | |
| 2010/0055751 A1 | 3/2010 | Voladri et al. | |
| 2010/0062499 A1 | 3/2010 | Mundorff et al. | |
| 2010/0151534 A1 | 6/2010 | Savile et al. | |
| 2010/0173369 A1 | 7/2010 | Savile et al. | |
| 2012/0149073 A1 | 6/2012 | Alvizo et al. | |
| 2013/0196408 A1 | 8/2013 | Ching et al. | |
| 2013/0210098 A1 | 8/2013 | Mundorff et al. | |
| 2013/0344552 A1 | 12/2013 | Liang et al. | |
| 2014/0057330 A1 | 2/2014 | Campopiano et al. | |
| 2014/0199735 A1 | 7/2014 | Gohel et al. | |

FOREIGN PATENT DOCUMENTS

| | | | |
|---|---|---|---|
| EP | | 1712633 A1 | 10/2006 |
| WO | WO 2001/040450 A1 | | 6/2001 |
| WO | WO 2002/086126 | | 10/2002 |
| WO | WO 2005/017135 A1 | | 2/2005 |
| WO | WO 2005/018579 A2 | | 3/2005 |
| WO | WO 2005/033094 A2 | | 4/2005 |
| WO | WO 2005/054491 A1 | | 6/2005 |
| WO | WO 2007/010944 | | 1/2007 |
| WO | WO 2007/012428 A1 | | 2/2007 |
| WO | WO 2008/042876 | | 4/2008 |
| WO | WO 2008/103248 | | 8/2008 |
| WO | | 2009/029554 A2 | 3/2009 |
| WO | | 2009/036404 A2 | 3/2009 |
| WO | | 2009/042984 A1 | 4/2009 |
| WO | | 2009/046153 A1 | 4/2009 |
| WO | | 2010/025085 A2 | 3/2010 |
| WO | | 2010/027710 A2 | 3/2010 |
| WO | | 2011/022548 A2 | 2/2011 |
| WO | | 2012/142302 A2 | 10/2012 |
| WO | | 2013/074650 A1 | 5/2013 |

OTHER PUBLICATIONS

Cha et al., 2002, "Stereochemical control in diastereoselective reduction of α-substituted-β-ketoesters using a reductase purified from *Kluyveromyces marxianus*," *Biotechnol. Lett*, 24:1695-1698.

Database EPO Proteins, Apr. 2007, "Sequence 4 from Patent WO2007012428," XP002488479, retrieved from EBI Accession No. EPOP:CS539287, Database Accession No. CS539287.

Daussmann et al., 2006, "Oxidoreductases and Hydroxynitrilase Lyases: Complementary Enzymatic Technologies for Chiral Alcohols," *Eng Life Sci.*, 6(2):125-129.

Fuganti et al., 1993, "Microbial Generation of (2R,3S)- and (2S,3S)-Ethyl 2-Benzamidomethyl-3-hydroxybutyrate, a Key Intermediate in the Synthesis of (3S,1'R)-3-(1'-Hydroxyethyl)azetidin-2-one," *J Chem. Soc. Perkin Trans.* 1:2247-2249.

Genbank Accession No. 1NXQ_A, Sep. 24, 2009.

Genbank Accession No. AJ544275, Feb. 17, 2003.

Genbank Accession No. AAP94029, Apr. 1, 2004.

Genbank Accession No. BAA24528.1, Jan. 29, 1998.

Genbank Accession No. CAD66648, Feb. 17, 2003.

Genbank Accession No. JC7338, Jun. 3, 2002.

Genbank Accession No. NP010159.1, Jun. 16, 2008.

Genbank Accession No. P41747, May 5, 2009.

Genbank Accession No. Q07551, Nov. 28, 2006.

Ghosh et al., 1993, "Cyclic Sulfolanes as Novel and High Affinity $P_2$ Ligands for HIV-1 Protease Inhibitors," *J. Med. Chem.*, 36(7):924-927.

Ghosh et al., 1994, "The Development of Cyclic Sulfolanes as Novel and High-Affinity $P_2$ Ligands for HIV-1 Protease Inhibitors," *J. Med. Chem.* 37:1177-1188.

Goldberg et al., 2007, "Biocatalytic ketone reduction—a powerful tool for the production of chiral alcohols—part I: processes with isolated enzymes," *Appl Microbiol Biotechnol*, 76(2):237-248.

Gröger et al., 2004, "Preparative asymmetric reduction of ketones in a biphasic medium with an (S)-alcohol dehydrogenase under in situ-cofactor-recycling with a formate dehydrogenase," *Tetrahedron* 60:633-640.

Hönig et al., 1994, "Enzymatic Resolutions of Heterocyclic Alcohols," *Biocatalysis* 9:61-69.

Hummel et al., 1989, "Dehydrogenases for the synthesis of chiral compounds," *Eur. J. Biochem.* 184:1-13.

Hummel, 1990, "Reduction of acetophenone to R(+)-phenylethanol by a new alcohol dehydrogenase from *Lactobacillus kefir*," *Appl Microbiol Biotechnol*, 34(1):15-19.

Hummel, 1999, "Large-scale applications of NAD(P)-dependent oxidoreductases: recent developments," *Trends Biotechnol.* 17(12):487-492.

Jones et al., 1981, "Enzymes in organic syntheses. 19.[1] Evaluation of the stereoselectivities of horse liver alcohol dehydrogenase; catalyzed oxidoreductions of hydroxy- and ketothiolanes, -thianes, and -thiepanes," *Can. J. Chem.*, 59:1574-1579.

Jörnvall et al., 1995, "Short-Chain Dehydrogenase/Reductases (SDR)," *Biochemistry* 34(18):6003-6013.

Kallberg et al., 2002, "Short-chain dehydrogenase/reductase (SDR) relationships: A large family with eight clusters common to human, animal, and plant genomes," *Protein Sci.* 11(3):636-641.

Kallberg et al., 2002, "Short-chain dehydrogenases/reductases (SDRs) Coenzyme-based functional assignments in completed genomes," *Eur. J. Biochem.* 269:4409-4417.

Niefind et al., 2003, "The Crystal Structure of R-specific Alcohol Dehydrogenase from *Lactobacillus brevis* Suggests the Structural Basis of its Metal Dependency," *J Mol Bio.* 327(2):317-28.

Partial PCT International Search Report from PCT/US2008/074135 dated Jan. 9, 2009.

PCT International Search Report from PCT/US2008/074135 dated May 20, 2009.

PCT International Search Report from PCT/US2008/078046 dated Jan. 13, 2009.

Petrash et al., 2001, "Functional Genomic Studies of Aldo-keto Reductases," *Chem Biol Interact.*, 130-132(1-3):673-83.

Rodrigues et al., 2004, "Recent Advances in the Biocatalytic Asymmetric Reduction of Acetophenones and α,β-Unsaturated Carbonyl Compounds," *Food Technol. Biotechnol.* 42 (4) 295-303.

Schlieben et al., 2005, "Atomic Resolution Structures of R-specific Alcohol Dehydrogenase from *Lactobacillus brevis* Provide the Structural Bases of its Substrate and Cosubstrate Specificity," *J. Mol. Biol.* 349(4):801-13.

(56) References Cited

OTHER PUBLICATIONS

Shimoda et al., 2006, "Diastereoselective reduction of β-keto carbonyl compounds by cultured plant cells," *Tetrahedron Lett.* 47(10):1541-1544.

Tandon et al., 1983, "Synthesis of Enantiomerically Pure (S)-(+)-3-Hydroxytetrahydrofuran and Its R Enantiomer from Malic or Tartaric Acid," *J. Org. Chem.* 48:2767-2769.

Temiño et al., 2005, "Entrapment of the alcohol dehydrogenase from *Lactobacillus kefir* in polyvinyl alcohol for the synthesis of chiral hydrophobic alcohols in organic solvents," *Enzyme Microb. Technol.*, 36(1):3-9.

U.S. Appl. No. 12/210,195, filed Sep. 13, 2008.

U.S. Appl. No. 12/243,968, filed Oct. 1, 2008.

Urban et al., 1999, "Synthesis of Optically Active 3(R)-[(Alkylsulfonyl)oxy]thiolanes from 2(R)-Hydroxy-4-(methylthio)butanoic Acid or D-Methionine," *J. Org. Chem.* 55:3670-3672.

Volkmann et al., 1992, "2-Thioalkyl Penems: An Efficient Synthesis of Sulopenem, a (5R,6S)-6-(1(R)-Hydroxyethyl)-2-[(cis-1-oxo-3-thiolanyl)thio]-2-penem Antibacterial," *J. Org. Chem.* 57(16):4352-61.

Weckbecker et al., 2006, "Cloning, expression, and characterization of an (R)-specific alcohol dehydrogenase from *Lactobacillus kefir*," *Biocatal. Biotransform.*, 24(5):380-389.

Wolberg et al., 2000, "Highly Regio- and Enantioselective Reduction of 3,5-Dioxocarboxylates," *Angew Chem. Int. Ed. Engl.* 39(23):4306-4308.

Wolberg, 2001, "Enzymatic Reduction of Hydrophobic beta, delta-Diketo Esters," *Synthesis* 937-942.

Xie et al., 2006, "Asymmetric Reduction of o-Chloroacetophenone with *Candida pseudotropicalis* 104," *Biotechnol. Prog.* 22:1301-1304.

Zhou et al., 1983, "Stereochemical Control of Yeast Reductions. 1. Asymmetric Synthesis of L-Carnitine," *J. Am. Chem. Soc.*, 105:5925-5926.

Zhu et al., 2005, "Evaluation of substituent effects on activity and enantioselectivity in the enzymatic reduction of aryl ketones," *Tetrahedron Asymm.* 16:1541-1546.

Broun et al., 1998, "Catalytic plasticity of fatty acid modification enzymes underlying chemical diversity of plant lipids," *Science*, vol. 282: 1315-1317.

Chica et al., 2005, "Semi-rational approaches to engineering enzyme activity: combining the benefits of directed evolution and rational design," *Curr. Opi. Bioctechol.*, vol. 16:378-384.

Devos, et al., 2000, "Practical limits of function prediction," *Proteins: Structure, Function and Genetics*, vol. 41:98-107.

Seffernick et al., 2001, "Melamine deaminase and Atrazine chlorohydrolase: 98 percent identical but functionally different," *J. Bacteriol.*, vol. 183(8):2405-2410.

Whisstock et al., 2003, "Prediction of protein function from protein sequence," *Q. Rev. Biophysics.*, 2003, vol. 36(3):307-340.

Witkowski et al., 1999, "Coversion of b-ketoacyl synthase to a malonyl decarboxylase by replacement of the active cysteine with glutamine," *Biochemistry*, vol. 38:11643-11.

* cited by examiner

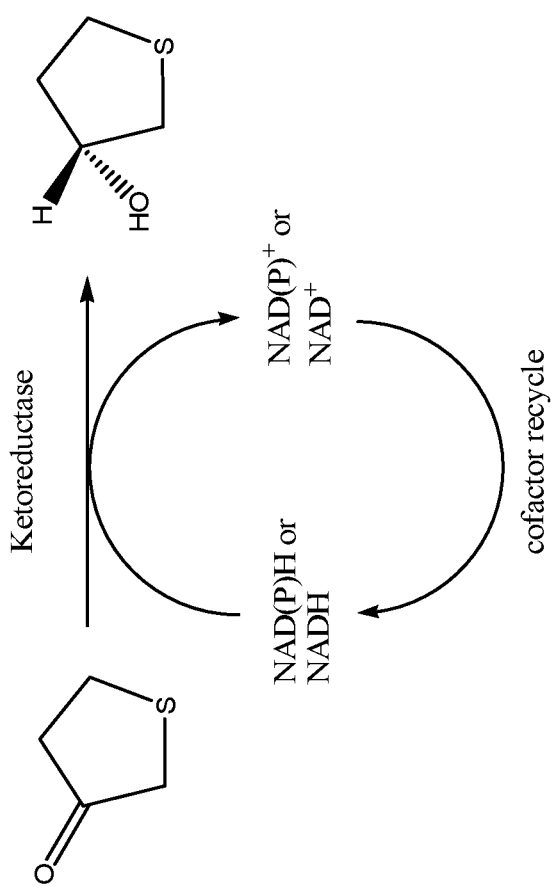

SEQUENCE LISTING

```
Sequence total quantity: 155
SEQ ID NO: 1            moltype = DNA  length = 762
FEATURE                 Location/Qualifiers
misc_feature            1..762
                        note = Codon Optimized L. Brevis Sequence
source                  1..762
                        mol_type = other DNA
                        organism = synthetic construct
SEQUENCE: 1
atgtctaacc gtctggatgg caaagtagcc atcattaccg gcgggactct gggtatcggt   60
ttggcaatcg ccacgaaatt tgtagaggag ggtgcgaaag taatgattac tggtcgtcac  120
tccgatgtag gtgaaaaggc cgccaaatca gtaggcactc cggatcagat tcagtttttt  180
cagcacgatt catccgatga agatggctgg acgaaactgt tcgacgccac cgagaaagca  240
ttcggcccgg ttagcacctt agtgaacaat gcagggattg cagttaacaa aagcgttgaa  300
gaaactacca cggccgaatg gcgtaaactg ctggccgtta atctggatgg tgtttttttc  360
ggcacccgtc tgggcattca gcgcatgaaa aataaaggct tgggcgctag catcatcaat  420
atgagcagta ttgaggggtt cgtaggcgat ccgagcctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctgccg  600
ggtgctgagg aagcgatgtc acagcgtacg aaaaccccta tgggccacat tggcgaaccg  660
aatgacatcg catatatctg tgtgtacctg gcatctaatg aatcgaaatt tgcgacgggt  720
tccgaatttg tggtcgacgg cgggtatacc gcacagtaat ga                    762

SEQ ID NO: 2            moltype = AA  length = 252
FEATURE                 Location/Qualifiers
REGION                  1..252
                        note = Translation of Codon Optimized L. Brevis Sequence
source                  1..252
                        mol_type = protein
```

```
                        organism = synthetic construct
SEQUENCE: 2
MSNRLDGKVA IITGGTLGIG LAIATKFVEE GAKVMITGRH SDVGEKAAKS VGTPDQIQFF    60
QHDSSDEDGW TKLFDATEKA FGPVSTLVNN AGIAVNKSVE ETTTAEWRKL LAVNLDGVFF   120
GTRLGIQRMK NKGLGASIIN MSSIEGFVGD PSLGAYNASK GAVRIMSKSA ALDCALKDYD   180
VRVNTVHPGY IKTPLVDDLP GAEEAMSQRT KTPMGHIGEP NDIAYICVYL ASNESKFATG   240
SEFVVDGGYT AQ                                                      252

SEQ ID NO: 3            moltype = DNA   length = 759
FEATURE                 Location/Qualifiers
misc_feature            1..759
                        note = Codon Optimized L. Kefir Sequence
source                  1..759
                        mol_type = other DNA
                        organism = synthetic construct
SEQUENCE: 3
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgt ttacgaccgt cgtgaacaat gcagggattg cagtttccaa aagcgttgaa   300
gacactacca cggaggaatg gcgtaaactg ctgtccgtta tctggatgg tgttttttc    360
ggcacccgtc tgggcattca gcgcatgaaa aataaaggct gggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccggggtat atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 4            moltype = AA   length = 252
FEATURE                 Location/Qualifiers
REGION                  1..252
                        note = Translation of Codon Optimized L. kefir Sequence
source                  1..252
                        mol_type = protein
                        organism = synthetic construct
SEQUENCE: 4
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 5            moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 5
atgaccgatc gtctgaaaag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgtttccaa aagcgttgaa   300
gacactacca cggaggaatg gcacaaactg ctgtccgtta tctggatag tgttttttc    360
ggcacccgtc tgggcattca gcgcatgaag aataaaggct gggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccggggtat atcaagaccc cgctggtcga tgatctggaa   600
ggtgctgagg aaatgatgtc acatcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 6            moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 6
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSHRT KTPMGHIGEP NDVAWICVYL ASDESKFATG   240
AEFVVDGGYT AQ                                                      252
```

```
SEQ ID NO: 7                 moltype = DNA  length = 759
FEATURE                      Location/Qualifiers
misc_feature                 1..759
                             note = Variant of L. kefir
source                       1..759
                             mol_type = other DNA
                             organism = synthetic construct
SEQUENCE: 7
atgaccgatc gtctgaagaa caaagtagcc atcgtaaccg gcgggactct gggtataggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgtttccaa aagcgttgaa   300
gacactacca cggaggattg cacaaactg ctgtccgtta atctggatag tgttttttc    360
ggcacccgtc tgggcattca gcgcatgaag aataaaggct gggcgctag catcatcaat   420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 8                 moltype = AA  length = 252
FEATURE                      Location/Qualifiers
REGION                       1..252
                             note = Variant of L. kefir
source                       1..252
                             mol_type = protein
                             organism = synthetic construct
SEQUENCE: 8
MTDRLKNKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEDWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                      252

SEQ ID NO: 9                 moltype = DNA  length = 759
FEATURE                      Location/Qualifiers
misc_feature                 1..759
                             note = Variant of L. kefir
source                       1..759
                             mol_type = other DNA
                             organism = synthetic construct
SEQUENCE: 9
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgtttccaa aagcgttgaa   300
gacactacca cggaggaatg cacaaactg ctgtccgtta atctggatag tgttttttc    360
ggcacccgtc tgggcattca gcgcatgaag aataaaggct gggcgctag catcatcaat   420
atgagcagta tcagtgggtt cgtaggcgat ccgacgctgg ggcatacac tgcttccaag    480
ggggcggtac gtatcatgtc gaaaagcgca gcgctggatt gcgcactgag ggactacgat   540
gtgcgtgtca acacagtaca tccgggctat atcaagaccc cgctggtcga tgatctggaa   600
ggtgctgagg aaatgcaatc acggcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 10                moltype = AA  length = 252
FEATURE                      Location/Qualifiers
REGION                       1..252
                             note = Variant of L. kefir
source                       1..252
                             mol_type = protein
                             organism = synthetic construct
SEQUENCE: 10
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWHKL LSVNLDSVFF   120
GTRLGIQRMK NKGLGASIIN MSSISGFVGD PTLGAYTASK GAVRIMSKSA ALDCALRDYD   180
VRVNTVHPGY IKTPLVDDLE GAEEMQSRRT KTPMGHIGEP NDVAWICVYL ASDESKFATG   240
AEFVVDGGYT AQ                                                      252

SEQ ID NO: 11                moltype = DNA  length = 759
FEATURE                      Location/Qualifiers
misc_feature                 1..759
                             note = Variant of L. kefir
source                       1..759
                             mol_type = other DNA
```

```
                      organism = synthetic construct
SEQUENCE: 11
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gcgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatag tgttttttc  360
ggcacccgtc tgggcattca gcgcatgaaa aataaaggct gggcgctag catcatcaat  420
atgagcagta tcagtgggtt cgtaggcgat ccgacgctgg gggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaacccta tggccacat tggcgaaccg  660
aatgacatcg catggatctg tgtgtacctg gcatctgacg aatcgaaatt tgcgacgggt  720
gcagaatttg tggtcgacgg cgggtatacc gcacagtga                          759

SEQ ID NO: 12          moltype = AA  length = 252
FEATURE                Location/Qualifiers
REGION                 1..252
                       note = Variant of L. kefir
source                 1..252
                       mol_type = protein
                       organism = synthetic construct
SEQUENCE: 12
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                      252

SEQ ID NO: 13          moltype = DNA  length = 759
FEATURE                Location/Qualifiers
misc_feature           1..759
                       note = Variant of L. kefir
source                 1..759
                       mol_type = other DNA
                       organism = synthetic construct
SEQUENCE: 13
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcacaaactg ctgtccgtta atctggatag tgttttttc  360
ggcacccgtc tgggcattca gcgcatgaaa aataaaggct gggcgctag catcatcaat  420
atgagcagta tcagtgggtt cgtaggcgat ccgacgctgg gggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaacccta tggccacat tggcgaaccg  660
aatgacatcg catggatctg tgtgtacctg gcatctgacg aatcgaaatt tgcgacgggt  720
gcagaatttg tggtcgacgg cgggtatacc gcacagtga                          759

SEQ ID NO: 14          moltype = AA  length = 252
FEATURE                Location/Qualifiers
REGION                 1..252
                       note = Variant of L. kefir
source                 1..252
                       mol_type = protein
                       organism = synthetic construct
SEQUENCE: 14
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                      252

SEQ ID NO: 15          moltype = DNA  length = 759
FEATURE                Location/Qualifiers
misc_feature           1..759
                       note = Variant of L. kefir
source                 1..759
                       mol_type = other DNA
                       organism = synthetic construct
SEQUENCE: 15
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
```

```
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta tcagtgggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctagtcga tgatctggaa   600
ggtgctgagg aaatgatgtc acagcgtacg aaaaccccta tgggccacat tggcgaaccg   660
aatgacgtcg catggatctg tgtgtacctg gcatctgacg aatcgaaatt tgcgacgggt   720
gcagaatttg tggtcgacgg cgggtatacc gcacagtga                         759

SEQ ID NO: 16             moltype = AA   length = 252
FEATURE                   Location/Qualifiers
REGION                    1..252
                          note = Variant of L. kefir
source                    1..252
                          mol_type = protein
                          organism = synthetic construct
SEQUENCE: 16
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSISGFVGD PTLGAYNASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                      252

SEQ ID NO: 17             moltype = DNA   length = 759
FEATURE                   Location/Qualifiers
misc_feature              1..759
                          note = Variant of L. kefir
source                    1..759
                          mol_type = other DNA
                          organism = synthetic construct
SEQUENCE: 17
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgacg catccgatga agcaggctgg acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgttttttc    360
ggcacccgtc tgggcattca gcgcatgaag aataaaggct tgggcgctag catcatcaat   420
atgagcagta tcagtgggct cgttgtcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc tgctggtcga tgatctggaa   600
ggtgctgagg aaatgatgtc acagcgtacg aaaaccccta tgggccacat tggcgaaccg   660
aatgacgtcg catggatctg tgtgtacctg gcatctgacg aatcgaaatt tgcgacgggt   720
gcagaatttg tggtcgacgg cgggtatacc gcacagtga                         759

SEQ ID NO: 18             moltype = AA   length = 252
FEATURE                   Location/Qualifiers
REGION                    1..252
                          note = Variant of L. kefir
source                    1..252
                          mol_type = protein
                          organism = synthetic construct
SEQUENCE: 18
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDGVFF   120
GTRLGIQRMK NKGLGASIIN MSSISGLVGD PTLGAYTASK GAVRIMSKSA ALDCALKDYD   180
VRVNTVHPGY IKTLLVDDLE GAEEMMSQRT KTPMGHIGEP NDVAWICVYL ASDESKFATG   240
AEFVVDGGYT AQ                                                      252

SEQ ID NO: 19             moltype = DNA   length = 759
FEATURE                   Location/Qualifiers
misc_feature              1..759
                          note = Variant of L. kefir
source                    1..759
                          mol_type = other DNA
                          organism = synthetic construct
SEQUENCE: 19
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgata catccgatga agcaggctga acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgttttttc    360
ggcacccgtc tgggcattca gcgcatgaag aataaaggct tgggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
```

```
gcagaatttg tggtcgacgg cgggtatacc gcacagtga                              759

SEQ ID NO: 20          moltype = AA   length = 252
FEATURE                Location/Qualifiers
REGION                 1..252
                       note = Variant of L. kefir
source                 1..252
                       mol_type = protein
                       organism = synthetic construct
SEQUENCE: 20
MTDRLKSKVA IVTGGTLGIG LAIADKFVEE GAKVVITGRH ADVGEKAAKS IGGTDVIRFV         60
QHDTSDEAGW TKLFDTTEEA FGPVTTVVNN AGITVPKSVE DTTTEEWHKL LSVNLDSVFF        120
GTRLGIQRMK NKGLGASIIN MSSISGFVGD PTLGAYTASK GAVRIMSKSA ALDCALKDYD        180
VRVNTVHPGY IKTPLVDDLE GAEEMMSQRT KTPMGHIGEP NDVAWICVYL ASDESKFATG        240
AEFVVDGGYT AQ                                                           252

SEQ ID NO: 21          moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 21
atgaccgatc gtctgaagag caaagtagcc atcgtaaccg gcgggactct gggtatcggt         60
ttggcaatcg ccgataaatt tgtagaggag ggtgcgaaag tagttattac tggtcgccac        120
gcggatgtag gtgaaaaggc cgccaaatca atcggcggta ctgatgttat tcgctttgtc        180
cagcacgatg catccgatga agcaggctgg acgaaactgt tcgacaccac cgaggaggca        240
ttcggcccgg ttacgaccgt cgtgaacaat gcaggggatta ccgttccaaa aagcgttgaa       300
gacactacca cggaggaatg gcacaaactg ctgtccgtta atctggatag tgttttttc        360
ggcacccgtc tgggcattca gcgcatgaag aataaaggct ggggcgctag catcatcaat       420
atgagcagta tcagtgggtt cgtaggcgat ccgacgctgg gggcatacac tgcttccaag       480
ggggcggtac gtatcatgtc gaaaagcgca gcgctggatt gcgcactgaa ggactacgat       540
gtgcgtgtca acacagtaca tccgggctat atcaagaccc acctggtcga tgatctgaa        600
ggtgctgagg aaatgcaatc acagcgtacg aaaaccccta tgggcacat tggcgaaccg        660
aatgacgtgg catggatctg tgtgtacctg gcatctgacg aatcgaaatt tgcgacgggt       720
gcagaatttg tggtcgacgg cgggtatacc gcacagtga                              759

SEQ ID NO: 22          moltype = AA   length = 252
FEATURE                Location/Qualifiers
REGION                 1..252
                       note = Variant of L. kefir
source                 1..252
                       mol_type = protein
                       organism = synthetic construct
SEQUENCE: 22
MTDRLKSKVA IVTGGTLGIG LAIADKFVEE GAKVVITGRH ADVGEKAAKS IGGTDVIRFV         60
QHDASDEAGW TKLFDTTEEA FGPVTTVVNN AGITVPKSVE DTTTEEWHKL LSVNLDSVFF        120
GTRLGIQRMK NKGLGASIIN MSSISGFVGD PTLGAYTASK GAVRIMSKSA ALDCALKDYD        180
VRVNTVHPGY IKTNLVDDLE GAEEMQSQRT KTPMGHIGEP NDVAWICVYL ASDESKFATG        240
AEFVVDGGYT AQ                                                           252

SEQ ID NO: 23          moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 23
atgaccgatc gtctgaagag caaagtagcc atcgtaaccg gcgggactct gggtatcggt         60
ttggcaatcg ccgataaatt tgtagaggag ggtgcgaaag tagttattac tggtcgccac        120
gcggatgtag gtgaaaaggc cgccaaatca atcggcggta ctgatgttat tcgctttgtc        180
cagcacgatg catccgatga agcaggctgg acgaaactgt tcgacaccac cgaggaggca        240
ttcggcccgg ttacgaccgt cgtgaacaat gcaggggatta ccgttccaaa aagcgttgaa       300
gacactacca cggaggaatg gcacaaactg ctgtccgtta atctggatag tgttttttc        360
ggcacccgtc tgggcattca gcgcatgaag aataaaggct ggggcgctag catcatcaat       420
atgagcagta tcagtgggtt cgtaggcgat ccgacgctgg gggcatacac tgcttccaag       480
ggggcggtac gtatcatgtc gaaaagcgca gcgctggatt gcgcactgaa ggactacgat       540
gtgcgtgtca acacagtaca tccgggctat atcaagaccc gctggtcga tgatctgaa         600
ggtgctgagg aaatgatgtc acagcgtacg aaaaccccta tgggccacat tggcgaaccg       660
aatgacgtgg catggatctg tgtgtacctg gcatctgacg aatcgaaatt tgcgacgggt       720
gcagaatttg tggtcgacgg cgggtatacc gcacagtga                              759

SEQ ID NO: 24          moltype = AA   length = 252
FEATURE                Location/Qualifiers
REGION                 1..252
                       note = Variant of L. kefir
source                 1..252
```

```
                        mol_type = protein
                        organism = synthetic construct
SEQUENCE: 24
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 25           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 25
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgtttttttc   360
ggcacccgtc tgggcattca gcgcatgaag aataaaggct gggcgctag catcatcaat    420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgcaatc acagcgtacg aaaacccta tgggccacat tggcgaaccg    660
aatgacgtga catggatctg tgtgtacctg gcatctgacg aatcgaaatt tgcgacgggt   720
gcagaatttg tggtcgacgg cgggtatacc gcacagtga                          759

SEQ ID NO: 26           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 26
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMQSQRT KTPMGHIGEP NDVAWICVYL ASDESKFATG   240
AEFVVDGGYT AQ                                                       252

SEQ ID NO: 27           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 27
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgtttttttc   360
ggcacccgtc tgggcattca gcgcatgaag aataaaggct gggcgctag catcatcaat    420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc acctggtcga tgatctggaa   600
ggtgctgagg aaatgcaatc acagcgtacg aaaacccta tgggccacat tggcgaaccg    660
aatgacgtga catggatctg tgtgtacctg gcatctgacg aatcgaaatt tgcgacgggt   720
gcagaatttg tggtcgacgg cgggtatacc gcacagtga                          759

SEQ ID NO: 28           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 28
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTDLVDDLE GAEEMQSQRT KTPMGHIGEP NDVAWICVYL ASDESKFATG   240
```

-continued

```
AEFVVDGGYT AQ                                                         252

SEQ ID NO: 29           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 29
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttccaaa aagcgttgaa  300
gacactacca cggaggaatg gcacaaactg ctgtccgtta atctggatag tgttttttc  360
ggcacccgtc tgggcattca gcgcatgaag aataaaggct gggcgctag catcatcaat  420
atgagcagta tcagtgggtt cgtaggcgat ccgacgctgg ggcatacac tgcttccaag  480
ggggcggtac gtatcatgtc gaaaagcgca gcgctggatt gcgcactgaa ggactacgat  540
gtgcgtgtca acacagtaca tccgggctat atcaagaccg gctggtcga tgatctggaa  600
ggtgctgagg aaatgcaatc acagcgtacg aaaaccccta tgggccacat tggcgaaccg  660
aatgacgtgg catggatctg tgtgtacctg gcatctgacg aatcgaaatt tgcgacgggt  720
gcagaatttg tggtcgacgg cgggtatacc gcacagtga                          759

SEQ ID NO: 30           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 30
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGITVPKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTGLVDDLE GAEEMQSQRT KTPMGHIGEP NDVAWICVYL ASDESKFATG  240
AEFVVDGGYT AQ                                                      252

SEQ ID NO: 31           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 31
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttgagaa aagcgttgaa  300
gacactacca cggaggaatg gcacaaactg ctgtccgtta atctggatag tgttttttc  360
ggcacccgtc tgggcattca gcgcatgaag aataaaggct gggcgctag catcatcaat  420
atgagcagta tcagtgggtt cgtaggcgat ccgacgctgg gggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc gctggtcga tgatctggaa  600
ggtgctgagg aaatgatgtc acagcgtacg aaaaccccta tgggccacat tggcgaaccg  660
aatgacgtgg catggatctg tgtgtacctg gcatctgacg aatcgaaatt tgcgacgggt  720
gcagaatttg tggtcgacgg cgggtatacc gcacagtga                          759

SEQ ID NO: 32           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 32
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGITVEKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHIGEP NDVAWICVYL ASDESKFATG  240
AEFVVDGGYT AQ                                                      252

SEQ ID NO: 33           moltype = DNA  length = 759
FEATURE                 Location/Qualifiers
misc_feature            1..759
                        note = Variant of L. kefir
source                  1..759
```

```
                    mol_type = other DNA
                    organism = synthetic construct
SEQUENCE: 33
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttgccaa aagcgttgaa   300
gacactacca cggaggaatg gcacaaactg ctgtccgtta atctggatag tgttttttc    360
ggcacccgtc tgggcattca gcgcatgaag aataaaggct tgggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                           759

SEQ ID NO: 34        moltype = AA  length = 252
FEATURE              Location/Qualifiers
REGION               1..252
                     note = Variant of L. kefir
source               1..252
                     mol_type = protein
                     organism = synthetic construct
SEQUENCE: 34
MTDRLKSKVA IVTGGTLGIG LAIADKFVEE GAKVVITGRH ADVGEKAAKS IGGTDVIRFV     60
QHDASDEAGW TKLFDTTEEA FGPVTTVVNN AGITVAKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 35        moltype = DNA  length = 759
FEATURE              Location/Qualifiers
misc_feature         1..759
                     note = Variant of L. kefir
source               1..759
                     mol_type = other DNA
                     organism = synthetic construct
SEQUENCE: 35
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgtttccaa aagcgttgaa   300
gacactacca cggaggaatg gcacaaactg ctgtccgtta atctggatag tgttttttc    360
ggcacccgtc tgggcattca gcgcatgaag aataaaggct tgggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                           759

SEQ ID NO: 36        moltype = AA  length = 252
FEATURE              Location/Qualifiers
REGION               1..252
                     note = Variant of L. kefir
source               1..252
                     mol_type = protein
                     organism = synthetic construct
SEQUENCE: 36
MTDRLKSKVA IVTGGTLGIG LAIADKFVEE GAKVVITGRH ADVGEKAAKS IGGTDVIRFV     60
QHDASDEAGW TKLFDTTEEA FGPVTTVVNN AGITVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 37        moltype = DNA  length = 759
FEATURE              Location/Qualifiers
misc_feature         1..759
                     note = Variant of L. kefir
source               1..759
                     mol_type = other DNA
                     organism = synthetic construct
SEQUENCE: 37
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
```

```
ttcggcccgg ttacgaccgt cgtgaacaat gcagggatta ccgtttccaa aagcgttgaa    300
gacactacca cggaggaatg gcacaaactg ctgtccgtta atctggatag tgttttttc    360
ggcacccgtc tgggcattca gcgcatgaag aataaaggct tgggcgctag catcatcaat    420
atgagcagta tcagtgggtt cgtaggcgat ccgacgctgg gggcatacac tgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgcaatc acagcgtacg aaaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759

SEQ ID NO: 38            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 38
MTDRLKSKVA IVTGGTLGIG LAIADKFVEE GAKVVITGRH ADVGEKAAKS IGGTDVIRFV     60
QHDASDEAGW TKLFDTTEEA FGPVTTVVNN AGITVSKSVE DTTTEEWHKL LSVNLDSVFF    120
GTRLGIQRMK NKGLGASIIN MSSISGFVGD PTLGAYTASK GAVRIMSKSA ALDCALKDYD    180
VRVNTVHPGY IKTPLVDDLE GAEEMQSQRT KTPMGHIGEP NDVAWICVYL ASDESKFATG    240
AEFVVDGGYT AQ                                                        252

SEQ ID NO: 39            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 39
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta ccgtttccag aagcgttgaa    300
gacactacca cggaggaatg gcacaaactg ctgtccgtta atctggatag tgttttttc    360
ggcacccgtc tgggcattca gcgcatgaag aataaaggct tgggcgctag catcatcaat    420
atgagcagta tcagtgggtt cgtaggcgat ccgacgctgg gggcatacac tgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgcaatc acagcgtacg aaaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759

SEQ ID NO: 40            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 40
MTDRLKSKVA IVTGGTLGIG LAIADKFVEE GAKVVITGRH ADVGEKAAKS IGGTDVIRFV     60
QHDASDEAGW TKLFDTTEEA FGPVTTVVNN AGITVSRSVE DTTTEEWHKL LSVNLDSVFF    120
GTRLGIQRMK NKGLGASIIN MSSISGFVGD PTLGAYTASK GAVRIMSKSA ALDCALKDYD    180
VRVNTVHPGY IKTPLVDDLE GAEEMQSQRT KTPMGHIGEP NDVAWICVYL ASDESKFATG    240
AEFVVDGGYT AQ                                                        252

SEQ ID NO: 41            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 41
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta ccgtttccct tagcgttgaa    300
gacactacca cggaggaatg gcacaaactg ctgtccgtta atctggatag tgttttttc    360
ggcacccgtc tgggcattca gcgcatgaag aataaaggct tgggcgctag catcatcaat    420
atgagcagta tcagtgggtt cgtaggcgat ccgacgctgg gggcatacac tgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
```

```
aatgacgtgg catggatctg tgtgtacctg gcatctgacg aatcgaaatt tgcgacgggt    720
gcagaatttg tggtcgacgg cgggtatacc gcacagtga                          759

SEQ ID NO: 42              moltype = AA  length = 252
FEATURE                    Location/Qualifiers
REGION                     1..252
                           note = Variant of L. kefir
source                     1..252
                           mol_type = protein
                           organism = synthetic construct
SEQUENCE: 42
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVSLSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 43              moltype = DNA  length = 759
FEATURE                    Location/Qualifiers
misc_feature               1..759
                           note = Variant of L. kefir
source                     1..759
                           mol_type = other DNA
                           organism = synthetic construct
SEQUENCE: 43
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcacaaactg ctgtccgtta atctggatag tgttttttc    360
ggcacccgtc tgggcattca gcgcatgaag aataaaggct gggcgctag catcatcaat    420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat   540
gtgcgtgtca acacagtaca tccgggctat atcgaaaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 44              moltype = AA  length = 252
FEATURE                    Location/Qualifiers
REGION                     1..252
                           note = Variant of L. kefir
source                     1..252
                           mol_type = protein
                           organism = synthetic construct
SEQUENCE: 44
MTDRLKSKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 45              moltype = DNA  length = 759
FEATURE                    Location/Qualifiers
misc_feature               1..759
                           note = Variant of L. kefir
source                     1..759
                           mol_type = other DNA
                           organism = synthetic construct
SEQUENCE: 45
atgaccgatc gtctgaagag caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcacaaactg ctgtccgtta atctggatag tgttttttc    360
ggcacccgtc tgggcattca gcgcatgaag aataaaggct gggcgctag catcatcaat    420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat   540
gtgcgtgtca acacagtaca tccgggctat atcgaaaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 46              moltype = AA  length = 252
FEATURE                    Location/Qualifiers
REGION                     1..252
                           note = Variant of L. kefir
```

```
source                  1..252
                        mol_type = protein
                        organism = synthetic construct
SEQUENCE: 46
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IETPLVDDLE GAEEMMSQRT KTPMGHIGEP NDVAWICVYL ASDESKFATG  240
AEFVVDGGYT AQ                                                     252

SEQ ID NO: 47           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 47
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcacaaactg ctgtccgtta atctggatag tgttttttc   360
ggcacccgtc tgggcattca gcgcatgaag aataaaggct gggcgctag catcatcaat  420
atgagcagta tcagtgggtt cgtaggcgat ccgacgctgg ggcatacac tgcttccaag  480
ggggcggtac gtatcatgtc gaaaagcgca gcgctggatt gcgcactgaa ggactacgat  540
gtgcgtgtca acacagtaca tccgggctat atcgagaccc cgctggtcga tgatctggaa  600
ggtgctgagg aaatgatgtc acagcgtacg aaaaccccta tgggccactt tggcgaaccg  660
aatgacgtgg catggatctg tgtgtacctg gcatctgacg aatcgaaatt tgcgacgggt  720
gcagaatttg tggtcgacgg cgggtatacc gcacagtga                        759

SEQ ID NO: 48           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 48
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IETPLVDDLE GAEEMMSQRT KTPMGHFGEP NDVAWICVYL ASDESKFATG  240
AEFVVDGGYT AQ                                                     252

SEQ ID NO: 49           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 49
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cggttcctaa aagcgttgaa  300
gacactacca cggaggaatg gcacaaactg ctgtccgtta atctggatag tgttttttc   360
ggcacccgtc tgggcattca gcgcatgaag aataaaggct gggcgctag catcatcaat  420
atgagcagta tcagtgggtt cgtaggcgat ccgacgctgg ggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgcaatc acagcgtacg aaaaccccta tgggccacat tggcgaaccg  660
aatgacgtgg catggatctg tgtgtacctg gcatctgacg aatcgaaatt tgcgacgggt  720
gcagaatttg tggtcgacgg cgggtatacc gcacagtga                        759

SEQ ID NO: 50           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 50
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVPKSVE DTTTEEWHKL LSVNLDSVFF  120
GTRLGIQRMK NKGLGASIIN MSSISGFVGD PTLGAYTASK GAVRIMSKSA ALDCALKDYD  180
```

```
VRVNTVHPGY IKTPLVDDLE GAEEMQSQRT KTPMGHIGEP NDVAWICVYL ASDESKFATG  240
AEFVVDGGYT AQ                                                     252

SEQ ID NO: 51           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 51
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cggttccaa aagcgttgaa   300
gacactacca cggaggaatg gcacaaactg ctgtccgtta atctggatag tgttttttc   360
ggcacccgtc tgggcattca cgcatgaag aataaaggct tgggcgctag catcatcaat   420
atgagcagta tcagtgggtt cgtaggcgat ccgacgctgg gggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctgaa   600
ggtgctgagg aaatgcaatc acagcgtacg aaaaccccta tggcccacat tggcgaaccg  660
aatgacgtgg catggatctg tgtgtacctg gcatctgacg aatcgaaatt tgcgacgggt  720
gcagaatttg tggtcgacgg cgggtatacc gcacagtga                        759

SEQ ID NO: 52           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 52
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMQSQRT KTPMGHIGEP NDVAWICVYL ASDESKFATG  240
AEFVVDGGYT AQ                                                     252

SEQ ID NO: 53           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 53
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg cgtccgatga agcaggctgg acgaaactgt tcgacaccac cgaggaggca  240
ttcggcccgg ttacgaccgt cgtgaacaat gcagggatta ccgttccaaa aagcgttgaa  300
gacactacca cggaggaatg gcacaaactg ctgtccgtta atctggatag tgttttttc   360
ggcacccgtc tgggcattca cgcatgaag aataaaggct tgggcgctag catcatcaat   420
atgagcagta tcagtgggtt cgtaaggcgat ccgacgctgg gggcatacac tgcttccaag  480
ggggcggtac gtatcatgtc gaaaagcgca gcgctggatt gcgcactgaa ggactacgat  540
gtgcgtgtca acacagtaca tccgggctat atcaagaccc gctggtcga tgatctggaa  600
ggtgctgagg aaatgatgtc acagcgtacg aaaaccccga tggtcactt ggcgagcca   660
aatgatgtgg catggatctg tgtgtacctg gcatctgacg aatcgaaatt tgcgacgggt  720
gcagaatttg tggtcgacgg cgggtatacc gcacagtga                        759

SEQ ID NO: 54           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 54
MTDRLKSKVA IVTGGTLGIG LAIADKFVEE GAKVVITGRH ADVGEKAAKS IGGTDVIRFV   60
QHDASDEAGW TKLFDTTEEA FGPVTTVVNN AGITVPKSVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHFGEP NDVAWICVYL ASDESKFATG  240
AEFVVDGGYT AQ                                                     252

SEQ ID NO: 55           moltype = DNA  length = 759
FEATURE                 Location/Qualifiers
misc_feature            1..759
                        note = Variant of L. kefir
```

```
source                   1..759
                         mol_type = other DNA
                         organism = synthetic construct
SEQUENCE: 55
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc tgccaaatca atcggcggta ctgatgttgt ccgctttgtc  180
cagcacgatg catccgatga agcaggctgg acgaaactgt tcgacaccac cgaggaggca  240
ttcggcccgg ttacgaccgt cgtgaacaat gcagggattc cagtttccga aagcgttgaa  300
gacactacca cggaggaatg gcacaaactg ctgtccgtta atctggatag tgttttttc   360
ggcacccgtc tgggcattca gcgcatgaaa aataaaggct gggcgctag catcatcaat   420
atgagcagta tcagtgggtt cgtaggcgat ccgacgctgg ggcatacac tgcttccaag   480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaaccccta tgggccacat tggcgaaccg  660
aatgacgtgg catggatctg tgtgtacctg gcatctgacg aatcgaaatt tgcgacgggt  720
gcagaatttg tggtcgacgg cgggtatacc gcacagtga                         759

SEQ ID NO: 56           moltype = AA    length = 252
FEATURE                 Location/Qualifiers
REGION                  1..252
                        note = Variant of L. kefir
source                  1..252
                        mol_type = protein
                        organism = synthetic construct
SEQUENCE: 56
MTDRLKSKVA IVTGGTLGIG LAIADKFVEE GAKVVITGRH ADVGEKAAKS IGGTDVVRFV   60
QHDASDEAGW TKLFDTTEEA FGPVTTVVNN AGIAVSESVE DTTTEEWHKL LSVNLDSVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHIGEP NDVAWICVYL ASDESKFATG  240
AEFVVDGGYT AQ                                                      252

SEQ ID NO: 57           moltype = DNA    length = 759
FEATURE                 Location/Qualifiers
misc_feature            1..759
                        note = Variant of L. kefir
source                  1..759
                        mol_type = other DNA
                        organism = synthetic construct
SEQUENCE: 57
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgagaaggc cgcccgttca atcggcggta ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttccaaa aagcgttgaa  300
gacactacca cggaggaatg cgcaaactg atgtccgtta atctggatag tgttttttc    360
ggcacccgtc tgggcattca gcgcatgaag aataaaggct tgggcgctag catcatcaat  420
atgagcagta tcagtgggtt cgtaggcgat ccgacgctgg ggcatacac tgcttccaag   480
ggggcggtac gtatcatgtc gaaaagcgca gcgctgggtt gcgcactgaa ggactacgat  540
gtgcgtgtca acacagtaca tccgggctat atcaagaccc gctggtcga tgatctgaa   600
ggtgctgagg aaatgcaatc acagcgtacg aaaaccccta tgggccacat tggcgaaccg  660
aatgacgtcg catggatctg tgtgtacctg gcatctgacg agtcgaaatt tgcgacgggt  720
gcagaatttg tggtcgacgg cgggtatacc gcacagtga                         759

SEQ ID NO: 58           moltype = AA    length = 252
FEATURE                 Location/Qualifiers
REGION                  1..252
                        note = Variant of L. kefir
source                  1..252
                        mol_type = protein
                        organism = synthetic construct
SEQUENCE: 58
MTDRLKSKVA IVTGGTLGIG LAIADKFVEE GAKVVITGRH ADVGEKAARS IGGTDVIRFV   60
QHDASDEAGW TKLFDTTEEA FGPVTTVVNN AGITVPKSVE DTTTEEWRKL MSVNLDSVFF  120
GTRLGIQRMK NKGLGASIIN MSSISGFVGD PTLGAYTASK GAVRIMSKSA ALGCALKDYD  180
VRVNTVHPGY IKTPLVDDLE GAEEMQSQRT KTPMGHIGEP NDVAWICVYL ASDESKFATG  240
AEFVVDGGYT AQ                                                      252

SEQ ID NO: 59           moltype = DNA    length = 759
FEATURE                 Location/Qualifiers
misc_feature            1..759
                        note = Variant of L. kefir
source                  1..759
                        mol_type = other DNA
                        organism = synthetic construct
SEQUENCE: 59
atgaccgatc gtctgaagag caaagtagcc atcgtaaccg gcgggactct gggtatcggt   60
ttggcaatcg ccgataaatt tgtagaggag ggtgcgaaag tagttattac tggtcgccac  120
gcggatgtag gtgagaaggc cgcccgttca atcggcggta ctgatgttat tcgctttgtc  180
```

```
cagcacgatg catccgatga agcaggctgg acgaaactgt tcgacaccac cgaggaggca    240
ttcggcccgg ttacgaccgt cgtgaacaat gcagggatta ccgtttccaa aagcgttgaa    300
gacactacca cggaggaatg gcgcaaactg atgtccgtta atctggatag tgttttttc     360
ggcacccgtc tgggcattca gcgcatgaag aataaaggct gggcgctag catcatcaat     420
atgagcagta tcagtgggtt cgtagccgat ccgacgctgg ggcatacac tgcttccaag     480
ggggcggtac gtatcatgtc gaaaagcgca gcgctgggtt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacgtgg catggatctg tgtgtacctg gcatctgacg agtcgaaatt tgcgacgggt    720
gcagaatttg tggtcgacgg cgggtatacc gcacagtga                           759

SEQ ID NO: 60           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 60
MTDRLKSKVA IVTGGTLGIG LAIADKFVEE GAKVVITGRH ADVGEKAARS IGGTDVIRFV     60
QHDASDEAGW TKLFDTTEEA FGPVTTVVNN AGITVSKSVE DTTTEEWRKL MSVNLDSVFF    120
GTRLGIQRMK NKGLGASIIN MSSISGFVGD PTLGAYTASK GAVRIMSKSA ALGCALKDYD    180
VRVNTVHPGY IKTPLVDDLE GAEEMMSQRT KTPMGHIGEP NDVAWICVYL ASDESKFATG    240
AEFVVDGGYT AQ                                                        252

SEQ ID NO: 61           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 61
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgagaaggc cgcccgttca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta ccgtttccaa aagcgttgaa    300
gacactacca cggaggaatg gcgcaaactg atgtccgtta atctggatag tgttttttc     360
ggcacccgtc tgggcattca gcgcatgaag aataaaggct gggcgctag catcatcaat     420
atgagcagta tcagtgggtt cgtaggcgat ccgacgctgg ggcatacac tgcttccaag     480
ggggcggtac gtatcatgtc gaaaagcgca gcgctgggtt gcgcactgaa ggactacgat    540
gtgcgtgtca acacagtaca tccgggctat atcaagaccc cgctggtcga tgatctggaa    600
ggtgctgagg aaatgcaatc acagcgtacg aaaaccccta tgggccacat tggcgaaccg    660
aatgacgtgg catggatctg tgtgtacctg gcatctgacg agtcgaaatt tgcgacgggt    720
gcagaatttg tggtcgacgg cgggtatacc gcacagtga                           759

SEQ ID NO: 62           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 62
MTDRLKSKVA IVTGGTLGIG LAIADKFVEE GAKVVITGRH ADVGEKAARS IGGTDVIRFV     60
QHDASDEAGW TKLFDTTEEA FGPVTTVVNN AGITVSKSVE DTTTEEWRKL MSVNLDSVFF    120
GTRLGIQRMK NKGLGASIIN MSSISGFVGD PTLGAYTASK GAVRIMSKSA ALGCALKDYD    180
VRVNTVHPGY IKTPLVDDLE GAEEMQSQRT KTPMGHIGEP NDVAWICVYL ASDESKFATG    240
AEFVVDGGYT AQ                                                        252

SEQ ID NO: 63           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 63
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgagaaggc cgcccgttca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttccaaa aagcgttgaa    300
gacactacca cggaggaatg gcgcaaactg atgtccgtta atctggatag tgttttttc     360
ggcacccgtc tgggcattca gcgcatgaag aataaaggct gggcgctag catcatcaat     420
atgagcagta tcagtgggtt cgtaggcgat ccgacgctgg ggcatacac tgcttccaag     480
ggggcggtac gtatcatgtc gaaaagcgca gcgctgggtt gcgcactgaa ggactacgat    540
gtgcgtgtca acacagtaca tccgggctat atcaagaccc cgctggtcga tgatctggaa    600
```

```
ggtgctgagg aaatgatgtc acagcgtacg aaaacccta tgggccacat tggcgaaccg    660
aatgacgtgg catggatctg tgtgtacctg gcatctgacg agtcgaaatt tgcgacgggt    720
gcagaatttg tggtcgacgg cgggtatacc gcacagtga                           759

SEQ ID NO: 64           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 64
MTDRLKSKVA IVTGGTLGIG LAIADKFVEE GAKVVITGRH ADVGEKAARS IGGTDVIRFV     60
QHDASDEAGW TKLFDTTEEA FGPVTTVVNN AGIAVPKSVE DTTTEEWRKL MSVNLDSVFF    120
GTRLGIQRMK NKGLGASIIN MSSISGFVGD PTLGAYTASK GAVRIMSKSA ALGCALKDYD    180
VRVNTVHPGY IKTPLVDDLE GAEEMMSQRT KTPMGHIGEP NDVAWICVYL ASDESKFATG    240
AEFVVDGGYT AQ                                                        252

SEQ ID NO: 65           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 65
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgagaaggc cgcccgttca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttccaaa aagcgttgaa    300
gacactacca cggaggaatg gcgcaaactg atgtccgtta atctggatag tgttttttc    360
ggcacccgtc tgggcattca gcgcatgaag aataaaggct gggcgctag catcatcaat   420
atgagcagta tcagtgggtt cgtaggcgat ccgacgctgg gggcatacac tgcttccaag    480
ggggcggtac gtatcatgtc gaaaagcgca gcgctgggtt gcgcactgaa ggactacgat    540
gtgcgtgtca acacagtaca tccgggctat atcaagaccc cgctggtcga tgatctggaa    600
ggtgctgagg aaatgcaatc acagcgtacg aaaacccta tgggccacat tggcgaaccg    660
aatgacgtgg catggatctg tgtgtacctg gcatctgacg agtcgaaatt tgcgacgggt    720
gcagaatttg tggtcgacgg cgggtatacc gcacagtga                           759

SEQ ID NO: 66           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 66
MTDRLKSKVA IVTGGTLGIG LAIADKFVEE GAKVVITGRH ADVGEKAARS IGGTDVIRFV     60
QHDASDEAGW TKLFDTTEEA FGPVTTVVNN AGIAVPKSVE DTTTEEWRKL MSVNLDSVFF    120
GTRLGIQRMK NKGLGASIIN MSSISGFVGD PTLGAYTASK GAVRIMSKSA ALGCALKDYD    180
VRVNTVHPGY IKTPLVDDLE GAEEMQSQRT KTPMGHIGEP NDVAWICVYL ASDESKFATG    240
AEFVVDGGYT AQ                                                        252

SEQ ID NO: 67           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 67
atgaccgatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgagaaggc cgcccgttca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttccaaa aagcgttgaa    300
gacactacca cggaggaatg gcgcaaactg atgtccgtta atctggatag tgttttttc    360
ggcacccgtc tgggcattca gcgcatgaag aataaaggct gggcgctag catcatcaat    420
atgagcagta tcagtgggtt cgtaggcgat ccgacgctgg gggcatacac tgcttccaag    480
ggggcggtac gtatcatgtc gaaaagcgca gcgctgggtt gcgcactgaa ggactacgat    540
gtgcgtgtca acacagtaca tccgggctat atcaagaccc cgctggtcga tgatctggaa    600
ggtgctgagg aaatgatgtc acagcgtacg aaaacccta tgggccacat tggcgaaccg    660
aatgacgtgg catggatctg tgtgtacctg gcatctgacg agtcgaaatt tgcgacgggt    720
gcagaatttg tggtcgacgg cgggtatacc gcacagtga                           759

SEQ ID NO: 68           moltype = AA  length = 252
FEATURE                 Location/Qualifiers
REGION                  1..252
```

```
                        note = Variant of L. kefir
source                  1..252
                        mol_type = protein
                        organism = synthetic construct
SEQUENCE: 68
MTDRLKSKVA IVTGGTLGIG LAIADKFVEE GAKVVITGRH ADVGEKAARS IGGTDVIRFV    60
QHDASDEAGW TKLFDTTEEA FGPVTTVVNN AGIAVSKSVE DTTTEEWRKL MSVNLDSVFF   120
GTRLGIQRMK NKGLGASIIN MSSISGFVGD PTLGAYTASK GAVRIMSKSA ALGCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 69           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 69
atgaccgatc gtctgaagag caaagtagcc atcgtaaccg cgggactct gggtatcggt     60
ttggcaatcg ccgataaatt tgtagaggag ggtgcgaaag tagttattac tggtcgccac   120
gcggatgtag gtgagaaggc cgcccgttca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgcaaactg atgtccgtta atctggatag tgttttttc   360
ggcacccgtc tgggcattca gcgcatgaag aataaaggct gggcgctag catcatcaat   420
atgagcagta tcagtgggtt cgtaggcgat ccgacgctgg gggcatacac tgcttccaag   480
ggggcggtac gtatcatgtc gaaaagcgca gcgctgggtt gcgcactgaa ggactacgat   540
gtgcgtgtca acacagtaca tccgggctat atcaagaccc cgctggtcga tgatctggaa   600
ggtgctgagg aaatgcaatc acagcgtacg aaaaccccta tgggccacat tggcgaaccg   660
aatgacgtgg catggatctg tgtgtacctg gcatctgacg agtcgaaatt tgcgacgggt   720
gcagaatttg tggtcgacgg cgggtatacc gcacagtga                         759

SEQ ID NO: 70           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 70
MTDRLKSKVA IVTGGTLGIG LAIADKFVEE GAKVVITGRH ADVGEKAARS IGGTDVIRFV    60
QHDASDEAGW TKLFDTTEEA FGPVTTVVNN AGIAVSKSVE DTTTEEWRKL MSVNLDSVFF   120
GTRLGIQRMK NKGLGASIIN MSSISGFVGD PTLGAYTASK GAVRIMSKSA ALGCALKDYD   180
VRVNTVHPGY IKTPLVDDLE GAEEMQSQRT KTPMGHIGEP NDVAWICVYL ASDESKFATG   240
AEFVVDGGYT AQ                                                       252

SEQ ID NO: 71           moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 71
atgaccgatc gtctgaagag caaagtagcc atcgtaaccg cgggggact gggtatcggt     60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgttttttc   360
ggcacccgtc tgggcattca gcgcatgaag aataaaggct gggcgctag catcatcaat   420
atgagcagta tcagtgggtt cgtaggcgat ccgacgctgg gggcatacac tgcttccaag   480
ggggcggtac gtatcatgtc gaaaagcgca gcgctgggtt gcgcactgaa ggactacgat   540
gtgcgtgtca acacagtaca tccgggctat atcaagaccc cgctggtcga tgatctggaa   600
ggtgctgagg aaatgcaatc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 72           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 72
MTDRLKSKVA IVTGGGLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDSVFF   120
```

```
GTRLGIQRMK NKGLGASIIN MSSISGFVGD PTLGAYTASK GAVRIMSKSA ALDCALKDYD    180
VRVNTVHPGY IKTPLVDDLE GAEEMQSQRT KTPMGHIGEP NDVAWICVYL ASDESKFATG    240
AEFVVDGGYT AQ                                                        252

SEQ ID NO: 73           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 73
atgaccgatc gtctgaagag caaagtagcc atcgtaaccg gcggggggact gggtatcggt    60
ttggcaatcg ccgataaatt tgtagaggag ggtgcgaaacg tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg cacaaaactg ctgtccgtta atctggatag tgttttttc   360
ggcacccgtc tgggcattca gcgcatgaag aataaaggct tgggcgctag catcatcaat   420
atgagcagta tcagtgggtt cgtaggcgat ccgacgctgg ggcatacac tgcttccaag    480
ggggcggtac gtatcatgtc gaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759

SEQ ID NO: 74           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 74
MTDRLKSKVA IVTGGGLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                        252

SEQ ID NO: 75           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 75
atgaccgatc gtctgaagag caaagtagcc atcgtaaccg gcggggggact gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cggttcctaa aagcgttgaa   300
gacactacca cggaggaatg cacaaaactg ctgtccgtta atctggatag tgttttttc   360
ggcacccgtc tgggcattca gcgcatgaag aataaaggct tgggcgctag catcatcaat   420
atgagcagta tcagtgggtt cgtaggcgat ccgacgctgg ggcatacac tgcttccaag    480
ggggcggtac gtatcatgtc gaaagcgca gcgctggatt gcgcactgaa ggactacgat    540
gtgcgtgtca acacagtaca tccgggctat atcaagaccc cgctggtcga tgatctggaa    600
ggtgctgagg aaatgcaatc acagcgtacg aaaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759

SEQ ID NO: 76           moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 76
MTDRLKSKVA IVTGGGLGIG LAIADKFVEE GAKVVITGRH ADVGEKAAKS IGGTDVIRFV    60
QHDASDEAGW TKLFDTTEEA FGPVTTVVNN AGIAVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMQSQRT KTPMGHIGEP NDVAWICVYL ASDESKFATG   240
AEFVVDGGYT AQ                                                        252

SEQ ID NO: 77           moltype = DNA  length = 759
FEATURE                 Location/Qualifiers
misc_feature            1..759
```

```
                        note = Variant of L. kefir
source                  1..759
                        mol_type = other DNA
                        organism = synthetic construct
SEQUENCE: 77
atgaccgatc gtctgaagag caaagtagcc atcgtaaccg gcggggggact gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg tggttcctaa aagcgttgaa   300
gacactacca cggaggaatg gcacaaactg ctgtccgtta atctggatag tgttttttc    360
ggcacccgtc tgggcattca gcgcatgaag aataaaggct gggcgctag catcatcaat    420
atgagcagta tcagtgggtt cgtaggcgat ccgacgctgg ggcatacac tgcttccaag    480
ggggcggtac gtatcatgtc gaaaagcgca gcgctgaatt gcgcactgaa ggactacgat   540
gtgcgtgtca acacagtaca tccgggctat atcaagaccc cgctggtcga tgatctggaa   600
ggtgctgagg aaatgcaatc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 78           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 78
MTDRLKSKVA IVTGGGLGIG LAIADKFVEE GAKVVITGRH ADVGEKAAKS IGGTDVIRFV    60
QHDASDEAGW TKLFDTTEEA FGPVTTVVNN AGIVVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMQSQRT KTPMGHIGEP NDVAWICVYL ASDESKFATG   240
AEFVVDGGYT AQ                                                       252

SEQ ID NO: 79           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 79
atgaccgatc gtctgaagag caaagtagcc atcgtaaccg gcggggtcct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttccaaa aagcgttgaa   300
gacactacca cggaggaatg gcacaaactg ctgtccgtta atctggatag tgttttttc    360
ggcacccgtc tgggcattca gcgcatgaag aataaaggct gggcgctag catcatcaat    420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgcaatc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 80           moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 80
MTDRLKSKVA IVTGGVLGIG LAIADKFVEE GAKVVITGRH ADVGEKAAKS IGGTDVIRFV    60
QHDASDEAGW TKLFDTTEEA FGPVTTVVNN AGITVPKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMQSQRT KTPMGHIGEP NDVAWICVYL ASDESKFATG   240
AEFVVDGGYT AQ                                                       252

SEQ ID NO: 81           moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 81
atgaccgatc gtctgaagca caaagtagcc atcgtaaccg gcgggactct gggtatcggt    60
ttggcaatcg ccgataaatt tgtagaggag ggtgcgaaag tagttattac tggtcgccac   120
```

```
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcacaaactg ctgtccgtta atctggatag tgttttttc    360
ggcacccgtc tgggcattca gcgcatgaag aataaaggct tgggcgctag catcatcaat   420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat   540
gtgcgtgtca acacagtaca tccgggctat atcaagaccc cgctggtcga tgatctgaa   600
ggtgctgagg aaatgatgtc acagcgtacg aaaaccccta tgggcacat tggcgaaccg    660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 82            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 82
MTDRLKHKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 83            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 83
atgaccgatc gtctgaaggg caaagtagcc accgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcatgatg catccgatga agcaggctgg acgaaactgt tcgacaccac cgaggaggca   240
ttcggcccgg ttacgactgt cgtgaacaat gcagggtta cagtttccaa aagcgttgaa    300
gacactacca cggaggaatg gcgcaaactg ctgtccgtta atctggatgg tgttttttc    360
ggcacccgtc tgggcattca gcgcatgaaa aataaaggct tgggcgctag catcatcaat   420
atgagcagta tgagggggtt cgtaggcgat ccgacgctgg ggcatacag cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctgaa   600
ggtgctgagg aaatgatgtc acagcgtacg aaaaccccta tgggcacat tggtgaaccg    660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 84            moltype = AA  length = 252
FEATURE                  Location/Qualifiers
REGION                   1..252
                         note = Variant of L. kefir
source                   1..252
                         mol_type = protein
                         organism = synthetic construct
SEQUENCE: 84
MTDRLKGKVA TVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYSASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                       252

SEQ ID NO: 85            moltype = DNA  length = 759
FEATURE                  Location/Qualifiers
misc_feature             1..759
                         note = Variant of L. kefir
source                   1..759
                         mol_type = other DNA
                         organism = synthetic construct
SEQUENCE: 85
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcacaaactg ctgtccgtta atctggatag tgttttttc    360
ggcacccgtc tgggcattca gcgcatgaaa aataaaggct tgggcgctag catcatcaat   420
atgagcagta tcagcgggtt cgtaggcgat ccgacgctgg ggcatacac tgcttccaag    480
ggggcggtac gtatcatgtc gaaaagcgca gcgctggatt gcgcactgaa ggactacgat   540
```

```
gtgcgtgtca acacagtaca tccgggctat atccgcaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 86          moltype = AA   length = 252
FEATURE                Location/Qualifiers
REGION                 1..252
                       note = Variant of L. kefir
source                 1..252
                       mol_type = protein
                       organism = synthetic construct
SEQUENCE: 86
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IRTPLVDDLE GAEEMMSQRT KTPMGHIGEP NDVAWICVYL ASDESKFATG   240
AEFVVDGGYT AQ                                                      252

SEQ ID NO: 87          moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 87
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggac ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa agcgttgaa    300
gacactacca cggaggaatg gcgtaaactg ctgtccgtta atctggatag tgttttttc    360
ggcacccgtc tgggcattca gcgcatgaaa aataaaggct gggcgctag catcatcaac    420
atgagcagta tcagtgggtt cgtaggcgat ccgacgctgg gggcatacac cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759

SEQ ID NO: 88          moltype = AA   length = 252
FEATURE                Location/Qualifiers
REGION                 1..252
                       note = Variant of L. kefir
source                 1..252
                       mol_type = protein
                       organism = synthetic construct
SEQUENCE: 88
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 89          moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 89
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa agcgttgaa    300
gacactacca cggaggaatg gcgtaaactg ctgtccgtta atctggatag tgttttttc    360
ggcacccgtc tgggcattca gcgcatgaaa aataaaggct gggcgctag catcatcaat    420
atgagcagta tcagtgggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacatgg catggatctg tgtgtacctg gcatctgacg aatcgaaatt tgcgacgggt   720
gcagaatttg tggtcgacgg cgggtatacc gcacagtga                          759

SEQ ID NO: 90          moltype = AA   length = 252
FEATURE                Location/Qualifiers
```

```
REGION                      1..252
                            note = Variant of L. kefir
source                      1..252
                            mol_type = protein
                            organism = synthetic construct
SEQUENCE: 90
MTDRLKGKVA IVTGGTLGIG LAIADKFVEE GAKVVITGRH ADVGEKAAKS IGGTDVIRFV      60
QHDASDEAGW TKLFDTTEEA FGPVTTVVNN AGIAVSKSVE DTTTEEWRKL LSVNLDSVFF     120
GTRLGIQRMK NKGLGASIIN MSSISGFVGD PTLGAYNASK GAVRIMSKSA ALDCALKDYD     180
VRVNTVHPGY IKTPLVDDLE GAEEMMSQRT KTPMGHIGEP NDIAWICVYL ASDESKFATG     240
AEFVVDGGYT AQ                                                         252

SEQ ID NO: 91               moltype = DNA   length = 759
FEATURE                     Location/Qualifiers
misc_feature                1..759
                            note = Variant of L. kefir
source                      1..759
                            mol_type = other DNA
                            organism = synthetic construct
SEQUENCE: 91
atgaccgatc gtctgaaggg caaagtagcc atcgtaaccg gcgggactct gggtatcggt      60
ttggcaatcg ccgataaatt tgtagaggag ggtgcgaaag tagttattac tggtcgccac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgt tacgaccgt cgtgaacaat gcagggattg cagtttccaa aagcgttgaa     300
gacactacca cggaggaatg gcgtaaactg ctgtccgtta atctggatag tgttttttc     360
ggcacccgtc tgggcattca gcgcatgaaa aataaaggct tgggcgctag catcatcaat     420
atgagcagta tcagtgggtt cgtaggcgat ccgacgctgg ggcatacac tgcttccaag     480
ggggcggtac gtatcatgtc gaaaagcgca gcgctggatt gcgcactgaa ggactacgat     540
gtgcgtgtca acacagtaca tccgggctat atccgcaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759

SEQ ID NO: 92               moltype = AA   length = 252
FEATURE                     Location/Qualifiers
REGION                      1..252
                            note = Variant of L. kefir
source                      1..252
                            mol_type = protein
                            organism = synthetic construct
SEQUENCE: 92
MTDRLKGKVA IVTGGTLGIG LAIADKFVEE GAKVVITGRH ADVGEKAAKS IGGTDVIRFV      60
QHDASDEAGW TKLFDTTEEA FGPVTTVVNN AGIAVSKSVE DTTTEEWRKL LSVNLDSVFF     120
GTRLGIQRMK NKGLGASIIN MSSISGFVGD PTLGAYTASK GAVRIMSKSA ALDCALKDYD     180
VRVNTVHPGY IRTPLVDDLE GAEEMMSQRT KTPMGHIGEP NDIAWICVYL ASDESKFATG     240
AEFVVDGGYT AQ                                                         252

SEQ ID NO: 93               moltype = DNA   length = 759
FEATURE                     Location/Qualifiers
misc_feature                1..759
                            note = Variant of L. kefir
source                      1..759
                            mol_type = other DNA
                            organism = synthetic construct
SEQUENCE: 93
atgaccgatc gtctgaaggg caaagtagcc atcgtaaccg gcgggactct gggtatcggt      60
ttggcaatcg ccgataaatt tgtagaggag ggtgcgaaag tagttattac tggtcgccac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatag tgttttttc     360
ggcacccgtc tgggcattca gcgcatgaaa aataaaggct tgggcgctag catcatcaat     420
atgagcagta tcagtgggtt cgtaggcgat ccgatgctgg ggcatacac tgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759

SEQ ID NO: 94               moltype = AA   length = 252
FEATURE                     Location/Qualifiers
REGION                      1..252
                            note = Variant of L. kefir
source                      1..252
                            mol_type = protein
                            organism = synthetic construct
SEQUENCE: 94
MTDRLKGKVA IVTGGTLGIG LAIADKFVEE GAKVVITGRH ADVGEKAAKS IGGTDVIRFV      60
```

```
QHDASDEAGW TKLFDTTEEA FGPVTTVVNN AGIAVSKSVE DTTTEEWRKL LSVNLDSVFF    120
GTRLGIQRMK NKGLGASIIN MSSISGFVGD PMLGAYTASK GAVRIMSKSA ALDCALKDYD    180
VRVNTVHPGY IKTPLVDDLE GAEEMMSQRT KTPMGHIGEP NDIAWICVYL ASDESKFATG    240
AEFVVDGGYT AQ                                                        252

SEQ ID NO: 95             moltype = DNA   length = 759
FEATURE                   Location/Qualifiers
misc_feature              1..759
                          note = Variant of L. kefir
source                    1..759
                          mol_type = other DNA
                          organism = synthetic construct
SEQUENCE: 95
atgaccgatc gtctgaaggg caaagtagcc atcgtaaccg gcgggactct gggtatcggt     60
ttggcaatcg ccgataaatt tgtagaggag ggtgcgaaag tagttattac tggtcgccac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta tcagtgggtt cgtaggcgat ccgacgctgg ggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta cgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                           759

SEQ ID NO: 96             moltype = AA   length = 252
FEATURE                   Location/Qualifiers
REGION                    1..252
                          note = Variant of L. kefir
source                    1..252
                          mol_type = protein
                          organism = synthetic construct
SEQUENCE: 96
MTDRLKGKVA IVTGGTLGIG LAIADKFVEE GAKVVITGRH ADVGEKAAKS IGGTDVIRFV     60
QHDASDEAGW TKLFDTTEEA FGPVTTVVNN AGIAVSKSVE DTTTEEWRKL LSVNLDGVFF    120
GTRLGIQRMK NKGLGASIIN MSSISGFVGD PTLGAYNASK GAVRIMSKSA ALDCALKDYD    180
VRVNTVHPGY IKTPLVDDLE GAEEMMSQRT KTPTGHIGEP NDIAWICVYL ASDESKFATG    240
AEFVVDGGYT AQ                                                        252

SEQ ID NO: 97             moltype = DNA   length = 759
FEATURE                   Location/Qualifiers
misc_feature              1..759
                          note = Variant of L. kefir
source                    1..759
                          mol_type = other DNA
                          organism = synthetic construct
SEQUENCE: 97
atgaccgatc gtctgaaggg caaagtagcc atcgtaaccg gcgggactct gggtatcggt     60
ttggcaatcg ccgataaatt tgtagaggag ggtgcgaaag tagttattac tggtcgccac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta tcagtgggtt cgtaggcgat ccgacgctgg ggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta cgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                           759

SEQ ID NO: 98             moltype = AA   length = 252
FEATURE                   Location/Qualifiers
REGION                    1..252
                          note = Variant of L. kefir
source                    1..252
                          mol_type = protein
                          organism = synthetic construct
SEQUENCE: 98
MTDRLKGKVA IVTGGTLGIG LAIADKFVEE GAKVVITGRH ADVGEKAAKS IGGTDVIRFV     60
QHDASDEAGW TKLFDTTEEA FGPVTTVVNN AGIAVSKSVE DTTTEEWRKL LSVNLDGVFF    120
GTRLGIQRMK NKGLGASIIN MSSISGFVGD PTLGAYNASK GAVRIMSKSA ALDCALKDYD    180
VRVNTVHPGY IKTPLVDDLE GAEEMMSQRT KTPMGHIGEP NDIAWICVYL ASDESKFATG    240
AEFVVDGGYT AQ                                                        252

SEQ ID NO: 99             moltype = DNA   length = 759
FEATURE                   Location/Qualifiers
```

| | | |
|---|---|---|
| misc_feature | 1..759 | |
| | note = Variant of L. kefir | |
| source | 1..759 | |
| | mol_type = other DNA | |
| | organism = synthetic construct | |

SEQUENCE: 99
```
atgaccgatc gtctgaaggg caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta tcagtgggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaaccccta tgggccactt tggcgaaccg  660
aatgacatcg cgtggatctg tgtgtacctg gcatctgacg aatcgaaatt tgcgacgggt  720
gcagaatttg tggtcgacgg cgggtatacc gcacagtga                         759
```

| | | |
|---|---|---|
| SEQ ID NO: 100 | moltype = AA   length = 252 | |
| FEATURE | Location/Qualifiers | |
| REGION | 1..252 | |
| | note = Variant of L. kefir | |
| source | 1..252 | |
| | mol_type = protein | |
| | organism = synthetic construct | |

SEQUENCE: 100
```
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSISGFVGD PTLGAYNASK GAVRIMSKSA ALDCALKDYD  180
VRVNTVHPGY IKTPLVDDLE GAEEMMSQRT KTPMGHFGEP NDIAWICVYL ASDESKFATG  240
AEFVVDGGYT AQ                                                     252
```

| | | |
|---|---|---|
| SEQ ID NO: 101 | moltype = DNA   length = 759 | |
| FEATURE | Location/Qualifiers | |
| misc_feature | 1..759 | |
| | note = Variant of L. kefir | |
| source | 1..759 | |
| | mol_type = other DNA | |
| | organism = synthetic construct | |

SEQUENCE: 101
```
atgaccgatc gtctgaaggg caaagtagcc atcgtaaccg gcgggactct gggtatcggt   60
ttggcaatcg ccgataaatt tgtagaggag ggtgcgaaag tagttattac tggtcgccac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta tcagtgggtt cgtaggcgat ccgacgctgg gggcatacac cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgctgagg aaatgatgtc acagcgtacg aaaaccccta tgggccacat tggcgaaccg  660
aatgacatcg catggatctg tgtgtacctg gcatctgacg aatcgaaatt tgcgacgggt  720
gcagaatttg tggtcgacgg cgggtatacc gcacagtga                         759
```

| | | |
|---|---|---|
| SEQ ID NO: 102 | moltype = AA   length = 252 | |
| FEATURE | Location/Qualifiers | |
| REGION | 1..252 | |
| | note = Variant of L. kefir | |
| source | 1..252 | |
| | mol_type = protein | |
| | organism = synthetic construct | |

SEQUENCE: 102
```
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSISGFVGD PTLGAYTASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                     252
```

| | | |
|---|---|---|
| SEQ ID NO: 103 | moltype = DNA   length = 759 | |
| FEATURE | Location/Qualifiers | |
| misc_feature | 1..759 | |
| | note = Variant of L. kefir | |
| source | 1..759 | |
| | mol_type = other DNA | |
| | organism = synthetic construct | |

SEQUENCE: 103
```
atgaccgatc gtctgaaggg caaagtagcc atcgtaaccg gcgggactct gggtatcggt   60
```

```
ttggcaatcg ccgataaatt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgagactgt tcgacaccac cgaggaggca   240
ttcggccccg ttacgaccgt cgtgaacaat gcagggattg cagtttccaa aagcgttgaa   300
gacactacca cggaggaatg gcgtaaactg ctgtccgtta atctggatag tgttttttc    360
ggcacccgtc tgggcattca gcgcatgaaa aataaaggct tgggcgctag catcatcaat   420
atgagcagta tcagtgggtt cgtaggcgat ccgacgctgg gggcatacac cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 104          moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 104
MTDRLKGKVA IVTGGTLGIG LAIADKFVEE GAKVVITGRH ADVGEKAAKS IGGTDVIRFV    60
QHDASDEAGW TRLFDTTEEA FGPVTTVVNN AGIAVSKSVE DTTTEEWRKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                      252

SEQ ID NO: 105          moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 105
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgccagatca atcggcggca ctgatgttat tcgctttgtc   180
cagcacgatg catccgatga agcaggctgg acgaaactgt ttgacaccac cgaggaggca   240
ttcggcccgg ttacgaccgt cgtgaacaat gcagggattg cagtttccaa aagcgttgaa   300
gacactacca cggaggaatg gcacaaactg ctgtccgtta atctggatag tgttttttc    360
ggcacccgtc tgggcattca gcgcatgaaa aataaaggct tgggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759

SEQ ID NO: 106          moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 106
MTDRLKGKVA IVTGGTLGIG LAIADKFVEE GAKVVITGRH ADVGEKAARS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                      252

SEQ ID NO: 107          moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 107
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtgaaaaggc cgcgaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta tcagtgggtt cgtaggcgat ccgacgctgg gggcatacaa cgcttccaag   480
```

```
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccctg tgggccacat tggcgaaccg   660
aatgacatcg catggatctg tgtgtacctg gcatctgacg aatcgaaatt tgcgacgggt    720
gcagaatttg tggtcgacgg cgggtatacc gcacagtga                           759
```

```
SEQ ID NO: 108          moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 108
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSISGFVGD PTLGAYNASK GAVRIMSKSA ALDCALKDYD   180
VRVNTVHPGY IKTPLVDDLE GAEEMMSQRT KTPVGHIGEP NDIAWICVYL ASDESKFATG   240
AEFVVDGGYT AQ                                                       252

SEQ ID NO: 109          moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 109
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtggcaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagttccaa aagcgttgaa    300
gacactacca cggaggaatg gcacaaactg ctgtccgtta atctggatag tgttttttc    360
ggcacccgtc tgggcattca gcgcatgaaa aataaaggct gggcgctag catcatcaat    420
atgagcagta tcagtgggtt cgtaggcgat ccgacgttgg gggcatacac tgcttccaag   480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccctg tgggccacat cggcgaaccg   660
aatgacgtgg catggatctg tgtgtacctg gcatctgacg aatcgaaatt tgcgacgggt    720
gcggaatttg tggtcgacgg cgggtatacc gcacagtga                           759
```

```
SEQ ID NO: 110          moltype = AA   length = 252
FEATURE                 Location/Qualifiers
REGION                  1..252
                        note = Variant of L. kefir
source                  1..252
                        mol_type = protein
                        organism = synthetic construct
SEQUENCE: 110
MTDRLKGKVA IVTGGTLGIG LAIADKFVEE GAKVVITGRH ADVGGKAAKS IGGTDVIRFV    60
QHDASDEAGW TKLFDTTEEA FGPVTTVVNN AGIAVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                       252

SEQ ID NO: 111          moltype = DNA   length = 759
FEATURE                 Location/Qualifiers
misc_feature            1..759
                        note = Variant of L. kefir
source                  1..759
                        mol_type = other DNA
                        organism = synthetic construct
SEQUENCE: 111
atgaccgatc gtctgaaggg caaagtagcc atcgtaaccg gcgggactct gggtatcggt    60
ttggcaatcg ccgataaatt tgtagaggag ggtgcgaaag tagttattac tggtcgccac   120
gcggatgtag gtggcaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cggtttccaa aagcgttgaa    300
gacactacca cggaggaatg gcacaaactg ctgtccgtta atctggatag tgttttttc    360
ggcacccgtc tgggcattca gcgcatgaaa aataaaggct gggcgctag catcatcaat    420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat    540
gtgcgtgtca acacagtaca tccgggctat atccgtggtcga tgatctggaa            600
ggtgctgagg aaatgatgtc acagcgtacg aaaaccccta tgggccacat tggcgaaccg   660
aatgacgtgg catggatctg tgtgtacctg gcatctgacg aatcgaaatt tgcgacgggt    720
gcagagtttg tggtcgacgg cgggtatacc gcacagtga                           759
```

```
SEQ ID NO: 112          moltype = AA   length = 252
```

```
FEATURE                 Location/Qualifiers
REGION                  1..252
                        note = Variant of L. kefir
source                  1..252
                        mol_type = protein
                        organism = synthetic construct
SEQUENCE: 112
MTDRLKGKVA IVTGGTLGIG LAIADKFVEE GAKVVITGRH ADVGGKAAKS IGGTDVIRFV      60
QHDASDEAGW TKLFDTTEEA FGPVTTVVNN AGIAVSKSVE DTTTEEWHKL LSVNLDSVFF     120
GTRLGIQRMK NKGLGASIIN MSSISGFVGD PTLGAYTASK GAVRIMSKSA ALDCALKDYD     180
VRVNTVHPGY IRTPLVDGLE GAEEMMSQRT KTPMGHIGEP NDVAWICVYL ASDESKFATG     240
AEFVVDGGYT AQ                                                         252

SEQ ID NO: 113          moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 113
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttgaggggtt cgtaggcgat ccgacgctgg ggcatacag cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctgaa      600
ggtgctgagg aaatgatgtc acagcgtacg aaaaccccta tgggccacat tggcgaaccg     660
aatgacatcg catggatctg tgcgtacctg gcatctgacg aatcgaaatt tgcgacgggt     720
gcagaatttg tggtcgacgg cgggtatacc gcacagtga                            759

SEQ ID NO: 114          moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 114
MTDRLKGKVA IVTGGTLGIG LAIADKFVEE GAKVVITGRH ADVGEKAAKS IGGTDVIRFV      60
QHDASDEAGW TKLFDTTEEA FGPVTTVVNN AGIAVSKSVE DTTTEEWRKL LSVNLDGVFF     120
GTRLGIQRMK NKGLGASIIN MSSIEGFVGD PTLGAYSASK GAVRIMSKSA ALDCALKDYD     180
VRVNTVHPGY IKTPLVDDLE GAEEMMSQRT KTPMGHIGEP NDIAWICAYL ASDESKFATG     240
AEFVVDGGYT AQ                                                         252

SEQ ID NO: 115          moltype = DNA  length = 759
FEATURE                 Location/Qualifiers
misc_feature            1..759
                        note = Variant of L. kefir
source                  1..759
                        mol_type = other DNA
                        organism = synthetic construct
SEQUENCE: 115
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttgatgggtt cgtaggcgat ccgacgctgg ggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctgaa      600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759

SEQ ID NO: 116          moltype = AA  length = 252
FEATURE                 Location/Qualifiers
REGION                  1..252
                        note = Variant of L. kefir
source                  1..252
                        mol_type = protein
                        organism = synthetic construct
SEQUENCE: 116
```

```
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIDGFVGD PTLGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 117           moltype = DNA   length = 759
FEATURE                  Location/Qualifiers
misc_feature             1..759
                         note = Variant of L. kefir
source                   1..759
                         mol_type = other DNA
                         organism = synthetic construct
SEQUENCE: 117
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta cagtttccaa aagcgttgaa   300
gacactacca cggaggaatg gcgtaaactg ctgtccgtta atctggatgg tgttttttc   360
ggcacccgtc tgggcgttca gcgcatgaaa aataaaggct gggcgctag catcatcaat   420
atgagcagta ttgaggggtt cgtaggcgat ccgacgctgg ggcatacag cgcttccaag   480
ggggcggtac gtatcatgtc gaaaagcgca gcgctggatt gcgcactgaa ggactacgat   540
gtgcgcgtca acacagtaca tccgggctat atcaagaccc cgctggtcga tgatctggaa   600
ggtgctgagg aaatgatgtc acagcgtacg aaaaacccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 118           moltype = AA   length = 252
FEATURE                  Location/Qualifiers
REGION                   1..252
                         note = Variant of L. kefir
source                   1..252
                         mol_type = protein
                         organism = synthetic construct
SEQUENCE: 118
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGVQRMK NKGLGASIIN MSSIEGFVGD PTLGAYSASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 119           moltype = DNA   length = 759
FEATURE                  Location/Qualifiers
misc_feature             1..759
                         note = Variant of L. kefir
source                   1..759
                         mol_type = other DNA
                         organism = synthetic construct
SEQUENCE: 119
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcatgatg catccgatga agcaggctgg acgaaactgt tcgacaccac cgaggaggca   240
ttcggcccgg ttacgactgt cgtgaacaat gcagggatta cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggtt cgtaggcgat ccgacgctgg gggcatacag cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaacccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 120           moltype = AA   length = 252
FEATURE                  Location/Qualifiers
REGION                   1..252
                         note = Variant of L. kefir
source                   1..252
                         mol_type = protein
                         organism = synthetic construct
SEQUENCE: 120
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTLGAYSASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 121           moltype = DNA   length = 759
```

| FEATURE | Location/Qualifiers |
|---|---|
| misc_feature | 1..759 |
| | note = Variant of L. kefir |
| source | 1..759 |
| | mol_type = other DNA |
| | organism = synthetic construct |

SEQUENCE: 121

```
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcgtca ctgatgttat tcgctttgtc   180
cagcacgacg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgtttttttc   360
ggcacccgtc tgggcattca gcgcatgaaa aataaaggct tgggcgctag catcatcaat   420
atgagcagta ttgaggggtt cgtaggcgat ccgacgctgg gggcatacag cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctgaaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                          759
```

| SEQ ID NO: 122 | moltype = AA length = 252 |
|---|---|
| FEATURE | Location/Qualifiers |
| REGION | 1..252 |
| | note = Variant of L. kefir |
| source | 1..252 |
| | mol_type = protein |
| | organism = synthetic construct |

SEQUENCE: 122

```
MTDRLKGKVA IVTGGTLGIG LAIADKFVEE GAKVVITGRH ADVGEKAAKS IGVTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTLGAYSASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                       252
```

| SEQ ID NO: 123 | moltype = DNA length = 759 |
|---|---|
| FEATURE | Location/Qualifiers |
| misc_feature | 1..759 |
| | note = Variant of L. kefir |
| source | 1..759 |
| | mol_type = other DNA |
| | organism = synthetic construct |

SEQUENCE: 123

```
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gtggatgtag gtgaaaaggc cgccagatca atcggcggca ctgatgttat tcgctttgtc   180
cagcacgacg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgtttttttc   360
ggcacccgtc tgggcattcg cgcatgaaa aataaaggct tgggcgctag catcatcaat   420
atgagcagta ttgaggggct cgtaggcgat ccgacgctgg gggcatacaa cgcttccaag   480
ggggcggtac gcatcatgtc gaaaagcgca gcgctggatt gcgcactgaa ggactacgat   540
gtgcgtgtca acacagtaca tccgggctat atcaagaccc cgctggtcga tgatctgaaa   600
ggtgctgagg aaatgatgtc acagcgtacg aaaaccccta tgggccactt ggcgaaccg    660
aatgacatcg catggatctg tgtgtacctg gcatctgacg aatcgaaatt tgcgacgggt   720
gcagaatttg tggtcgacgg cgggtatacc gcacagtga                          759
```

| SEQ ID NO: 124 | moltype = AA length = 252 |
|---|---|
| FEATURE | Location/Qualifiers |
| REGION | 1..252 |
| | note = Variant of L. kefir |
| source | 1..252 |
| | mol_type = protein |
| | organism = synthetic construct |

SEQUENCE: 124

```
MTDRLKGKVA IVTGGTLGIG LAIADKFVEE GAKVVITGRH VDVGEKAARS IGGTDVIRFV    60
QHDASDEAGW TKLFDTTEEA FGPVTTVVNN AGIAVSKSVE DTTTEEWRKL LSVNLDGVFF   120
GTRLGIRRMK NKGLGASIIN MSSIEGLVGD PTLGAYNASK GAVRIMSKSA ALDCALKDYD   180
VRVNTVHPGY IKTPLVDDLK GAEEMMSQRT KTPMGHFGEP NDIAWICVYL ASDESKFATG   240
AEFVVDGGYT AQ                                                       252
```

| SEQ ID NO: 125 | moltype = DNA length = 759 |
|---|---|
| FEATURE | Location/Qualifiers |
| misc_feature | 1..759 |
| | note = Variant of L. kefir |
| source | 1..759 |
| | mol_type = other DNA |
| | organism = synthetic construct |

SEQUENCE: 125

```
atgaccgatc gtctgaaggg caaagtagcc atcgtaaccg gcgggactct gggtgttggt    60
ttggcaatcg ccgataaatt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta tcagtgggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 126         moltype = AA   length = 252
FEATURE                Location/Qualifiers
REGION                 1..252
                       note = Variant of L. kefir
source                 1..252
                       mol_type = protein
                       organism = synthetic construct
SEQUENCE: 126
MTDRLKGKVA IVTGGTLGVG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSISGFVGD PTLGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                       252

SEQ ID NO: 127         moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 127
atgaccgatc gtctgaaggg caaagtagcc atcgtaaccg gcggggctct gggtatcggt    60
ttggcaatcg ccgataaatt tgtagaggag ggtgcgaaag tagttattac tggtcgccac   120
gcggatgtag gtgaaaaggc cgccaaatca atcggcggca ctgatgttgt tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta tcagtgggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 128         moltype = AA   length = 252
FEATURE                Location/Qualifiers
REGION                 1..252
                       note = Variant of L. kefir
source                 1..252
                       mol_type = protein
                       organism = synthetic construct
SEQUENCE: 128
MTDRLKGKVA IVTGGALGIG LAIADKFVEE GAKVVITGRH ADVGEKAAKS IGGTDVVRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSISGFVGD PTLGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                       252

SEQ ID NO: 129         moltype = DNA   length = 759
FEATURE                Location/Qualifiers
misc_feature           1..759
                       note = Variant of L. kefir
source                 1..759
                       mol_type = other DNA
                       organism = synthetic construct
SEQUENCE: 129
atgaccgatc gtctgaaggg caaagtagcc atcgtaaccg gcggggctct gggtatcggt    60
ttggcaatcg ccgataagtt tgtagaggag ggtgcgaaag tagttattac tggtcgccac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtctccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
```

```
atgagcagta tcagtgggtt cgtaggcgac ccgacgttag gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                           759

SEQ ID NO: 130              moltype = AA    length = 252
FEATURE                     Location/Qualifiers
REGION                      1..252
                            note = Variant of L. kefir
source                      1..252
                            mol_type = protein
                            organism = synthetic construct
SEQUENCE: 130
MTDRLKGKVA IVTGGALGIG LAIADKFVEE GAKVVITGRH ADVGEKAAKS IGGTDVIRFV     60
QHDASDEAGW TKLFDTTEEA FGPVTTVVNN AGIAVSKSVE DTTTEEWRKL LSVNLDGVFF    120
GTRLGIQRMK NKGLGASIIN MSSISGFVGD PTLGAYNASK GAVRIMSKSA ALDCALKDYD    180
VRVNTVHPGY IKTPLVDDLE GAEEMMSQRT KTPMGHIGEP NDIAWICVYL ASDESKFATG    240
AEFVVDGGYT AQ                                                        252

SEQ ID NO: 131              moltype = DNA    length = 759
FEATURE                     Location/Qualifiers
misc_feature                1..759
                            note = Variant of L. kefir
source                      1..759
                            mol_type = other DNA
                            organism = synthetic construct
SEQUENCE: 131
atgaccgatc gtctgaaggg cagagtagcc atcgtaaccg gcgggactct gggtatcggt     60
ttggcattcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta cagcttccaa aagcgttgaa    300
gacactacca cggaggaatg gcataaactg ctgtccgtta atctggatgg tgttttttc    360
ggcacccgtc tgggcattca gcgcatgaaa aataaaggct gggcgctag catcatcaat    420
atgagcagta ttgaggggtt cgtaggcgat ccgacgctgg ggcatacag cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggtgaaccg    660
aatgacatcg catggatctg tgtgtacctg gcatctgacg aatcgaaatt tgcgacgggt    720
gcagaatttg tggtcgacgg cgggtatacc gcacagtga                           759

SEQ ID NO: 132              moltype = AA    length = 252
FEATURE                     Location/Qualifiers
REGION                      1..252
                            note = Variant of L. kefir
source                      1..252
                            mol_type = protein
                            organism = synthetic construct
SEQUENCE: 132
MTDRLKGRVA IVTGGTLGIG LAFADKFVEE GAKVVITGRH ADVGEKAAKS IGGTDVIRFV     60
QHDASDEAGW TKLFDTTEEA FGPVTTVVNN AGITASKSVE DTTTEEWHKL LSVNLDGVFF    120
GTRLGIQRMK NKGLGASIIN MSSIEGFVGD PTLGAYSASK GAVRIMSKSA ALDCALKDYD    180
VRVNTVHPGY IKTPLVDDLE GAEEMMSQRT KTPMGHIGEP NDIAWICVYL ASDESKFATG    240
AEFVVDGGYT AQ                                                        252

SEQ ID NO: 133              moltype = DNA    length = 759
FEATURE                     Location/Qualifiers
misc_feature                1..759
                            note = Variant of L. kefir
source                      1..759
                            mol_type = other DNA
                            organism = synthetic construct
SEQUENCE: 133
atgacctatc gtctgaagag caaagtagcc atcgtaaccg gcgggactct gggtatcggt     60
ttggcaatcg ccgataaatt tgtagaggag ggtgcgaaag tagttattac tggtcgccac    120
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta ccgtttccaa aagcgttgaa    300
gacactacca cggaggaatg gcacaaacta ctgtccgtta atctggatag tgttttttc    360
ggcacccgtc tgggcattca gcgcatgaaa aataaaggct gggcgctag catcatcaat    420
atgagcagta tcagtgggtt cgtaggcgat ccgacgctgg ggcatacac tgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat tggcgaaccg    660
aatgacgtgc catggatctg tgtgtacctg gcatctgacg aatcgaaatt tgcgacgggt    720
gcagaatttg tggtcgacgg cgggtatacc gcacagtga                           759
```

```
SEQ ID NO: 134            moltype = AA  length = 252
FEATURE                   Location/Qualifiers
REGION                    1..252
                          note = Variant of L. kefir
source                    1..252
                          mol_type = protein
                          organism = synthetic construct
SEQUENCE: 134
MTYRLKSKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWHKL LSVNLDSVFF   120
GTRLGIQRMK NKGLGASIIN MSSISGFVGD PTLGAYTASK GAVRIMSKSA ALDCALKDYD   180
VRVNTVHPGY IKTPLVDDLE GAEEMMSQRT KTPMGHIGEP NDVAWICVYL ASDESKFATG   240
AEFVVDGGYT AQ                                                      252

SEQ ID NO: 135            moltype = DNA  length = 1041
FEATURE                   Location/Qualifiers
misc_feature              1..1041
                          note = Codon optimized ADH-SB from S. salmonicolor
source                    1..1041
                          mol_type = other DNA
                          organism = synthetic construct
SEQUENCE: 135
atgaaggcac tgcagtaccg caccatcggc gccccgcccg aggtcgtcac cgtcccggac     60
ccggagccgg gccccggcca ggtgctgttg aaggtgaccg cggccggagt ctgccactcc    120
gacatcgcgg tgatgagctg gcccgccgag ggcttcccgt acgagctgcc gctcaccctc    180
ggccacgagg gcgtcggcac cgtggccgcg ctcggcgcgg gggtgacggg cgtcgccgag    240
ggcgacgcgg tcgccgtgta cgggccctgg ggctgcggca cctgcgccaa gtgcgccgag    300
ggcaaggaga actactgcct gcgcgccgac gagctgggca tccgtccgcc ggggctcggg    360
cgtccggggt ccatggccga gtacctgctg atcgacgacc cccggcacct ggtcccgctg    420
gacgggctcg acccggtcgc ggccgtgccg ctcaccgacg ccggactgac gccgtaccac    480
gcgatcaagc ggtcgctgcc caagctggtc cccggctcca ccggggtggt catcggcacc    540
ggtggtctcg gccacgtcgc catccagctg ctgcgcgccc tgacgtccgc ccgggtggtc    600
gccctggacg tcagcgagga agctgcgcgc tcgcccgtg cggtgggcgc gcacgaggcg    660
gtgctgtcgg acgcgaaggc cgcggacgcg gtgcgcgaga tcaccggcgg tctcggtgcc    720
gaggccgtgt tcgacttcgt cggcgtggcg cccaccgtgc agaccgccgg agccgtcgcg    780
gccgtcgagg gcgatgtcac cctggtcggc atcggcggcg gatcgctgcc cgtcggcttc    840
ggcatgctgc cgttcgaggt gtcggtcaac gccccctact ggggcagccg cagcgagctg    900
accgaggtgc tgaacctggc ccgctccggt gccgtgtcgg tgcacaccga gacgtactcc    960
ctggacgacg cccccgctcgc ctacgagcgg ctgcacgagg gcagggtcaa cggccgcgcg   1020
gtgatcctgc cccacggctg a                                              1041

SEQ ID NO: 136            moltype = AA  length = 346
FEATURE                   Location/Qualifiers
REGION                    1..346
                          note = ADH-SB from S. salmonicolor
source                    1..346
                          mol_type = protein
                          organism = synthetic construct
SEQUENCE: 136
MKALQYRTIG APPEVVTVPD PEPGPGQVLL KVTAAGVCHS DIAVMSWPAE GFPYELPLTL    60
GHEGVGTVAA LGAGVTGLAE GDAVAVYGPW GCGTCAKCAE GKENYCLRAD ELGIRPPGLG   120
RPGSMAEYLL IDDPRHLVPL DGLDPVAAVP LTDAGLTPYH AIKRSLPKLV PGSTAVVIGT   180
GGLGHVAIQL LRALTSARVV ALDVSEEKLR LARAVGAHEA VLSDAKAADA VREITGLGLA   240
EAVFDFVGVA PTVQTAGAVA AVEGDVTLVG IGGGSLPVGF GMLPFEVSVN APYWGSRSEL   300
TEVLNLARSG AVSVHTETYS LDDAPLAYER LHEGRVNGRA VILPHG                  346

SEQ ID NO: 137            moltype = DNA  length = 1032
FEATURE                   Location/Qualifiers
misc_feature              1..1032
                          note = Codon optimized ADH-SC from S. coelicolor
source                    1..1032
                          mol_type = other DNA
                          organism = synthetic construct
SEQUENCE: 137
atggcaaaga tcgacaacgc agttctgccg gagggttctc tggtgctggt caccggcgcg    60
aacggctttg tcgctagcca tgtggtcgaa caactgctgg aacacggcta aaggtgcgc   120
ggcactgctc gctctgcctc caaactggcg aacctgcaga aacgttggga cgccaaatac   180
cctggtcgtt tcgagactgc cgttgttgaa gacatgctga gcagggtgc atatgatgaa   240
gttattaaag gcgcggcagg tgtcgcccac atcgcgtccg tggtcagctt ttctaacaaa   300
tatgatgagg tggtaactcc tgcgatcggt ggcacgctga atgccctgcg tgccgcagct   360
gctacgcctt ccgtgaaacg ttttgtgctg accagcagca ctgtttctgc actgattcca   420
aaacctaacg tcgaaggtat ttatctggat gagaagagct ggaacctgga agcattgat   480
aaggctaaaa cctgcctga atctgatccg cagaaaagcc tgtgggtcta cgccgcaagc   540
aaaacggaag ggaactggc tgcctggaaa ttcatgaacg aaaacaaacc gcacttact   600
ctgaatgccg ttctgccaaa ctacactatc ggtaccattt tgacccaga acccaatcc   660
ggttccactt ccggctggat gatgtctctg ttcaatggcg aagtatctcc ggcactggcg   720
ctgatgccgc gcagtacta tgtctctgca gttgatatcg gtctgctgca cctgggttgt   780
ctggttctgc gcaaatcga acgccgtcgt gtttacggca ccgcaggcac ctttgattgg   840
aacaccgttc tggcgacctt ccgtaaactg tatccgtcca gacgttccc ggctgacttt   900
```

```
ccggatcagg gccaggatct gtccaaattt gataccgccc cgagcctgga gattctgaaa   960
tccctgggcc gccctggctg gcgtagcatc gaggaatcta tcaaagatct ggtgggttcc  1020
gagaccgcct aa                                                      1032

SEQ ID NO: 138         moltype = AA   length = 343
FEATURE                Location/Qualifiers
REGION                 1..343
                       note = ADH-SC from S. coelicolor
source                 1..343
                       mol_type = protein
                       organism = synthetic construct
SEQUENCE: 138
MAKIDNAVLP EGSLVLVTGA NGFVASHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                    343

SEQ ID NO: 139         moltype = DNA   length = 1056
FEATURE                Location/Qualifiers
misc_feature           1..1056
                       note = Codon optimized ADH-TB from T brockii
source                 1..1056
                       mol_type = other DNA
                       organism = synthetic construct
SEQUENCE: 139
atgaaaggct cgccatgct gagcatcggc aaagtgggtt ggattgaaaa agaaaaaccg    60
gcgccaggc cgttcgatgc aattgtgcgc cctctggcag tagcgccgtg taccagcgat   120
attcatactg tgtttgaagg tgccattggc gagcgtcaca atatgattct gggccatgaa   180
gccgttggtg aagttgttga ggttggcagc gaagtgaagg atttcaaacc gggcgatcgc   240
gttgtcgttc cagcgattac cccggattgg cgcaccagcg aagtccagcg cggctaccat   300
cagcactctg gcggcatgct ggccggctgg aaattcagca atgtaaagga tggtgtgttc   360
ggtgaattt tcacgttaa cgacgcagac atgaatctgg cgcacctgcc gaaagaaatc   420
ccgctggaag cagcggttat gattccggat atgatgacca cgggtttca cggcgcagag   480
ctggcggaca ttgaactggg cgctacggta gccgtactgg gcatcggtcc ggtgggcctg   540
atggcagttg caggcgctaa gctgcgcggc gcaggtcgta ttattgccgt tggttctcgc   600
ccggtgtgtg tggacgccgc taagtattat ggtgcaacgg acattgtcaa ttacaaggac   660
ggcccaattg aatctcagat catgaacctg acggaaggta aaggcgttga cgccgcgatt   720
atcgctggcg gcaacgccga catcatggcg accgcagtta aaatcgtcaa gccaggtggt   780
actattgcta acgtcaacta cttcggcgaa ggtgaggtcc tgcctgtccc acgtctggaa   840
tggggttgcg gtatggcaca taaaaccatt aaaggtggcc tgtgcccagg cggccgtctg   900
cgtatggaac gcctgatcga tctggtcttc tacaaacgcg ttgatccag caaactggtg   960
actcacgttt tccgcggctt tgataacatc gaaaaagctt ttatgctgat gaaagataaa  1020
ccgaaagatc tgattaaacc ggttgtcatc ctggct                           1056

SEQ ID NO: 140         moltype = AA   length = 352
FEATURE                Location/Qualifiers
REGION                 1..352
                       note = ADH-TB from T brockii
source                 1..352
                       mol_type = protein
                       organism = synthetic construct
SEQUENCE: 140
MKGFAMLSIG KVGWIEKEKP APGPFDAIVR PLAVAPCTSD IHTVFEGAIG ERHNMILGHE    60
AVGEVVEVGS EVKDFKPGDR VVVPAITPDW RTSEVQRGYH QHSGGMLAGW KFSNVKDGVF   120
GEFFHVNDAD MNLAHLPKEI PLEAAVMIPD MMTTGFHGAE LADIELGATV AVLGIGPVGL   180
MAVAGAKLRG AGRIIAVGSR PVCVDAAKYY GATDIVNYKD GPIESQIMNL TEGKGVDAAI   240
IAGGNADIMA TAVKIVKPGG TIANVNYFGE GEVLPVPRLE WGCGMAHKTI KGGLCPGGRL   300
RMERLIDLVF YKRVDPSKLV THVFRGFDNI EKAFMLMKDK PKDLIKPVVI LA          352

SEQ ID NO: 141         moltype = DNA   length = 759
FEATURE                Location/Qualifiers
source                 1..759
                       mol_type = other DNA
                       organism = Lactobacillus minor
SEQUENCE: 141
atgaccgatc ggttgaaggg gaaagtagca attgtaactg gcggtaccct gggaattggc    60
ttggcaatcg ctgataagtt tgttgaagaa ggcgcaaagg tcgttattac cggccgtcac   120
gctgatgtag tgaaaaagc tgccagatca atcggcggca cagacgttat ccgttttgtc   180
caacacgatg cttctgatga accggctgg actaagttgt tgatacgac tgaagaagca   240
tttggcccga ttaccacggt tgtcaacaat gccggaattg cggtcagcaa gagtgttgaa   300
gataccacaa ctgaagaatg cgcaagctg ctctcagtta acttggatgg tgtcttcttc   360
ggtacccgtc ttggaatcca acgtatgaag aataaaggac tcggagcatc aatcatcaat   420
atgtcatcta tcgaaggttt tgttggtgat ccagctctgg gtgcatacaa cgcttccaaa   480
ggtgctgtca gaattatgtc taaatcagct gccttggatt gcgctttgaa ggactacgat   540
gttcgggtta acactgttca tccaggttat atcaagacac cattggttga cgatcttgaa   600
ggggcagaag aaatgatgtc acagcggacc aagacaccaa tgggtcatat cggtgaacct   660
aacgatatcg cttggatctg tgtttacctg gcatctgacg aatctaaatt tgccactggt   720
```

```
gcagaattcg ttgtcgacgg agggtacacc gcccaatag                    759
```

```
SEQ ID NO: 142          moltype = AA  length = 252
FEATURE                 Location/Qualifiers
source                  1..252
                        mol_type = protein
                        organism = Lactobacillus minor
SEQUENCE: 142
MTDRLKGKVA IVTGGTLGIG LAIADKFVEE GAKVVITGRH ADVGEKAARS IGGTDVIRFV   60
QHDASDETGW TKLFDTTEEA FGPVTTVVNN AGIAVSKSVE DTTTEEWRKL LSVNLDGVFF  120
GTRLGIQRMK NKGLGASIIN MSSIEGFVGD PALGAYNASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                     252

SEQ ID NO: 143          moltype = AA  length = 252
FEATURE                 Location/Qualifiers
REGION                  1..252
                        note = Synthetic Construct
SITE                    3
                        note = MISC_FEATURE - Xaa is a polar, acidic, or aromatic
                         residue
SITE                    7
                        note = MISC_FEATURE - Xaa is a polar, non-polar, or
                         constrained residue
SITE                    11
                        note = MISC_FEATURE - Xaa is an aliphatic, non-polar, or
                         polar residue
SITE                    16
                        note = MISC_FEATURE - Xaa is an aliphatic or non-polar
                         residue
SITE                    19
                        note = MISC_FEATURE - Xaa is a non-polar or aliphatic
                         residue
SITE                    23
                        note = MISC_FEATURE - Xaa is a non-polar or aromatic residue
SITE                    41
                        note = MISC_FEATURE - Xaa is an aliphatic, polar, or
                         non-polar residue
SITE                    45
                        note = MISC_FEATURE - Xaa is an aliphatic, non-polar, or
                         polar residue
SITE                    49
                        note = MISC_FEATURE - Xaa is a basic residue
SITE                    57
                        note = MISC_FEATURE - Xaa is an aliphatic ornonpolar residue
SITE                    60
                        note = MISC_FEATURE - Xaa is an aromatic, aliphatic, polar
                         or non-polar residue
SITE                    64
                        note = MISC_FEATURE - Xaa is an aliphatic or non-polar
                         residue
SITE                    72
                        note = MISC_FEATURE - Xaa is a basic residue
SITE                    82
                        note = MISC_FEATURE - Xaa is a polar or non-polar residue
SITE                    94
                        note = MISC_FEATURE - Xaa is a polar, non-polar, basic, or
                         aliphatic residue
SITE                    95
                        note = MISC_FEATURE - Xaa is a non-polar or aliphatic
                         residue
SITE                    96
                        note = MISC_FEATURE - Xaa is a constrained, aliphatic,
                         acidic, polar or non-polarresidue
SITE                    97
                        note = MISC_FEATURE - Xaa is an acidic, basic, or aliphatic
                         residue
SITE                    106
                        note = MISC_FEATURE - Xaa is an acidic residue
SITE                    108
                        note = MISC_FEATURE - Xaa is a basic, constrained, or
                         aromatic residue
SITE                    111
                        note = MISC_FEATURE - Xaa is an aliphatic or nonpolar
                         residue
SITE                    117
                        note = MISC_FEATURE - Xaa is a polar or non-polar residue
SITE                    126
                        note = MISC_FEATURE - Xaa is an aliphatic or nonpolar
```

```
                            residue
SITE            127
                note = MISC_FEATURE - Xaa is a polar or basic residue
SITE            145
                note = MISC_FEATURE - Xaa is a polar residue
SITE            147
                note = MISC_FEATURE - Xaa is an aromatic, aliphatic, polar,
                    or non-polar residue
SITE            152
                note = MISC_FEATURE - Xaa is a polar, aliphatic or nonpolar
                    residue
SITE            157
                note = MISC_FEATURE - Xaa is a polar or acidic residue
SITE            163
                note = MISC_FEATURE - Xaa is an aliphatic or nonpolar
                    residue
SITE            173
                note = MISC_FEATURE - Xaa is an acidic or non-polar residue
SITE            177
                note = MISC_FEATURE - Xaa is a basic residue
SITE            192
                note = MISC_FEATURE - Xaa is a basic or acidic residue
SITE            194
                note = MISC_FEATURE - Xaa is a constrained, acidic,
                    aliphatic, polar, or non-polarresidue
SITE            198
                note = MISC_FEATURE - Xaa is an acidic or non-polar residue
SITE            200
                note = MISC_FEATURE - Xaa is a constrained, acidic, or
                    basic residue
SITE            206
                note = MISC_FEATURE - Xaa is a polar or non-polar residue
SITE            208
                note = MISC_FEATURE - Xaa is a polar, constrained, or basic
                    residue
SITE            210
                note = MISC_FEATURE - Xaa is an aliphatic, polar or
                    non-polar residue
SITE            211
                note = MISC_FEATURE - Xaa is a basic or acidic residue
SITE            214
                note = MISC_FEATURE - Xaa is a nonpolar, aliphatic or polar
                    residue
SITE            217
                note = MISC_FEATURE - Xaa is an aromatic, aliphatic or
                    non-polar residue
SITE            223
                note = MISC_FEATURE - Xaa is an aliphatic or nonpolar
                    residue
SITE            226
                note = MISC_FEATURE - Xaa is a nonpolar or aliphatic residue
SITE            228
                note = MISC_FEATURE - Xaa is a nonpolar or aliphatic residue
source          1..252
                mol_type = protein
                organism = synthetic construct
SEQUENCE: 143
MTXRLKXKVA XVTGGXLGXG LAXADKFVEE GAKVVITGRH XDVGXKAAXS IGGTDVXRFX    60
QHDXSDETGW TXLFDTTEEA FXPVTTVVNN AGIXXXXSVE DTTTEXWXKL XSVNLDXVFF   120
GTRLGXXRMK NKGLGASIIN MSSIXGXVGD PXLGAYXASK GAXRIMSKSA ALXCALXDYD   180
VRVNTVHPGY IXTXLVDXLX GAEEMXSXRX XTPXGHXGEP NDXAWXCXYL ASDESKFATG   240
AEFVVDGGYT AQ                                                      252

SEQ ID NO: 144      moltype = AA  length = 252
FEATURE             Location/Qualifiers
REGION              1..252
                note = Synthetic Construct
SITE            3
                note = MISC_FEATURE - Xaa is a polar, acidic, or aromatic
                    residue
SITE            7
                note = MISC_FEATURE - Xaa is a polar, non-polar, or
                    constrained residue
SITE            11
                note = MISC_FEATURE - Xaa is an aliphatic, non-polar, or
                    polar residue
SITE            16
                note = MISC_FEATURE - Xaa is an aliphatic or non-polar
                    residue
```

-continued

| | |
|---|---|
| SITE | 19<br>note = MISC_FEATURE - Xaa is a non-polar or aliphatic residue |
| SITE | 23<br>note = MISC_FEATURE - Xaa is a non-polar or aromatic residue |
| SITE | 41<br>note = MISC_FEATURE - Xaa is an aliphatic, polar, or non-polar residue |
| SITE | 45<br>note = MISC_FEATURE - Xaa is an aliphatic, non-polar, or polar residue |
| SITE | 49<br>note = MISC_FEATURE - Xaa is an basic residue |
| SITE | 57<br>note = MISC_FEATURE - Xaa is an aliphatic ornonpolar residue |
| SITE | 60<br>note = MISC_FEATURE - Xaa is an aromatic, aliphatic, polar or non-polar residue |
| SITE | 64<br>note = MISC_FEATURE - Xaa is an aliphatic or non-polar residue |
| SITE | 72<br>note = MISC_FEATURE - Xaa is a basic residue |
| SITE | 82<br>note = MISC_FEATURE - Xaa is a polar or non-polar residue |
| SITE | 94<br>note = MISC_FEATURE - Xaa is a polar, non-polar, basic, or aliphatic residue |
| SITE | 95<br>note = MISC_FEATURE - Xaa is a non-polar or aliphatic residue |
| SITE | 96<br>note = MISC_FEATURE - Xaa is a constrained, aliphatic, acidic, polar or non-polarresidue |
| SITE | 97<br>note = MISC_FEATURE - Xaa is an acidic, basic, or aliphatic residue |
| SITE | 106<br>note = MISC_FEATURE - Xaa is an acidic residue |
| SITE | 108<br>note = MISC_FEATURE - Xaa is a basic, constrained, or aromatic residue |
| SITE | 111<br>note = MISC_FEATURE - Xaa is an aliphatic or nonpolar residue |
| SITE | 117<br>note = MISC_FEATURE - Xaa is a polar or non-polar residue |
| SITE | 126<br>note = MISC_FEATURE - Xaa is an aliphatic or nonpolar residue |
| SITE | 127<br>note = MISC_FEATURE - Xaa is a polar or basic residue |
| SITE | 145<br>note = MISC_FEATURE - Xaa is a polar residue |
| SITE | 147<br>note = MISC_FEATURE - Xaa is an aromatic, aliphatic, polar, or non-polar residue |
| SITE | 152<br>note = MISC_FEATURE - Xaa is a polar, aliphatic or nonpolar residue |
| SITE | 157<br>note = MISC_FEATURE - Xaa is a polar or acidic residue |
| SITE | 163<br>note = MISC_FEATURE - Xaa is an aliphatic or nonpolar residue |
| SITE | 173<br>note = MISC_FEATURE - Xaa is an acidic or non-polar residue |
| SITE | 177<br>note = MISC_FEATURE - Xaa is a basic residue |
| SITE | 192<br>note = MISC_FEATURE - Xaa is a basic or acidic residue |
| SITE | 194<br>note = MISC_FEATURE - Xaa is a constrained, acidic, aliphatic, polar, or non-polarresidue |
| SITE | 198<br>note = MISC_FEATURE - Xaa is an acidic or non-polar residue |
| SITE | 200<br>note = MISC_FEATURE - Xaa is a constrained, acidic, or basic residue |

| | |
|---|---|
| SITE | 206 |
| | note = MISC_FEATURE - Xaa is a polar or non-polar residue |
| SITE | 208 |
| | note = MISC_FEATURE - Xaa is a polar, constrained, or basic residue |
| SITE | 210 |
| | note = MISC_FEATURE - Xaa is an aliphatic, polar or non-polar residue |
| SITE | 211 |
| | note = MISC_FEATURE - Xaa is a basic or acidic residue |
| SITE | 214 |
| | note = MISC_FEATURE - Xaa is a nonpolar, aliphatic or polar residue |
| SITE | 217 |
| | note = MISC_FEATURE - Xaa is an aromatic, aliphatic or non-polar residue |
| SITE | 223 |
| | note = MISC_FEATURE - Xaa is an aliphatic or nonpolar residue |
| SITE | 226 |
| | note = MISC_FEATURE - Xaa is an nonpolar or aliphatic residue |
| SITE | 228 |
| | note = MISC_FEATURE - Xaa is a nonpolar or aliphatic residue |
| source | 1..252 |
| | mol_type = protein |
| | organism = synthetic construct |

SEQUENCE: 144
```
MSXRLDXKVA XITGGXLGXG LAXATKFVEE GAKVMITGRH XDVGXKAAXS VGTPDQXQFX  60
QHDXSDEDGW TXLFDATEKA FXPVSTLVNN AGIXXXXSVE ETTTAXWXKL XAVNLDXVFF 120
GTRLGXXRMK NKGLGASIIN MSSIXGXVGD PXLGAYXASK GAXRIMSKSA ALXCALXDYD 180
VRVNTVHPGY IXTXLVDXLX GAEEAXSXRX XTPXGHXGEP NDXAYXCXYL ASNESKFATG 240
SEFVVDGGYT AQ                                                   252
```

| | |
|---|---|
| SEQ ID NO: 145 | moltype = AA  length = 252 |
| FEATURE | Location/Qualifiers |
| REGION | 1..252 |
| | note = Synthetic Construct |
| SITE | 3 |
| | note = MISC_FEATURE - Xaa is a polar, acidic, or aromatic residue |
| SITE | 7 |
| | note = MISC_FEATURE - Xaa is a polar, non-polar, or constrained residue |
| SITE | 11 |
| | note = MISC_FEATURE - Xaa is an aliphatic, non-polar, or polar residue |
| SITE | 16 |
| | note = MISC_FEATURE - Xaa is an aliphatic or non-polar residue |
| SITE | 19 |
| | note = MISC_FEATURE - Xaa is a non-polar or aliphatic residue |
| SITE | 23 |
| | note = MISC_FEATURE - Xaa is a non-polar or aromatic residue |
| SITE | 41 |
| | note = MISC_FEATURE - Xaa is an aliphatic, polar, or non-polar residue |
| SITE | 45 |
| | note = MISC_FEATURE - Xaa is an aliphatic, non-polar, or polar residue |
| SITE | 49 |
| | note = MISC_FEATURE - Xaa is a basic residue |
| SITE | 57 |
| | note = MISC_FEATURE - Xaa is an aliphatic ornonpolar residue |
| SITE | 60 |
| | note = MISC_FEATURE - Xaa is an aromatic, aliphatic, polar or non-polar residue |
| SITE | 64 |
| | note = MISC_FEATURE - Xaa is an aliphatic or non-polar residue |
| SITE | 72 |
| | note = MISC_FEATURE - Xaa is a basic residue |
| SITE | 82 |
| | note = MISC_FEATURE - Xaa is a polar or non-polar residue |
| SITE | 94 |
| | note = MISC_FEATURE - Xaa is a polar, non-polar, basic, or aliphatic residue |
| SITE | 95 |

|  |  |
|---|---|
|  | note = MISC_FEATURE - Xaa is a non-polar or aliphatic residue |
| SITE | 96 |
|  | note = MISC_FEATURE - Xaa is a constrained, aliphatic, acidic, polar or non-polarresidue |
| SITE | 97 |
|  | note = MISC_FEATURE - Xaa is an acidic, basic, or aliphatic residue |
| SITE | 106 |
|  | note = MISC_FEATURE - Xaa is an acidic residue |
| SITE | 108 |
|  | note = MISC_FEATURE - Xaa is a basic, constrained, or aromatic residue |
| SITE | 111 |
|  | note = MISC_FEATURE - Xaa is an aliphatic or nonpolar residue |
| SITE | 117 |
|  | note = MISC_FEATURE - Xaa is a polar or non-polar residue |
| SITE | 126 |
|  | note = MISC_FEATURE - Xaa is an aliphatic or nonpolar residue |
| SITE | 127 |
|  | note = MISC_FEATURE - Xaa is a polar or basic residue |
| SITE | 145 |
|  | note = MISC_FEATURE - Xaa is a polar residue |
| SITE | 147 |
|  | note = MISC_FEATURE - Xaa is an aromatic, aliphatic, polar, or non-polar residue |
| SITE | 152 |
|  | note = MISC_FEATURE - Xaa is a polar, aliphatic or nonpolar residue |
| SITE | 157 |
|  | note = MISC_FEATURE - Xaa is a polar or acidic residue |
| SITE | 163 |
|  | note = MISC_FEATURE - Xaa is an aliphatic or nonpolar residue |
| SITE | 173 |
|  | note = MISC_FEATURE - Xaa is an acidic or non-polar residue |
| SITE | 177 |
|  | note = MISC_FEATURE - Xaa is a basic residue |
| SITE | 192 |
|  | note = MISC_FEATURE - Xaa is a basic or acidic residue |
| SITE | 194 |
|  | note = MISC_FEATURE - Xaa is a constrained, acidic, aliphatic, polar, or non-polarresidue |
| SITE | 198 |
|  | note = MISC_FEATURE - Xaa is an acidic or non-polar residue |
| SITE | 200 |
|  | note = MISC_FEATURE - Xaa is a constrained, acidic, or basic residue |
| SITE | 206 |
|  | note = MISC_FEATURE - Xaa is a polar or non-polar residue |
| SITE | 208 |
|  | note = MISC_FEATURE - Xaa is a polar, constrained, or basic residue |
| SITE | 210 |
|  | note = MISC_FEATURE - Xaa is an aliphatic, polar or non-polar residue |
| SITE | 211 |
|  | note = MISC_FEATURE - Xaa is a basic or acidic residue |
| SITE | 214 |
|  | note = MISC_FEATURE - Xaa is a nonpolar, aliphatic or polar residue |
| SITE | 217 |
|  | note = MISC_FEATURE - Xaa is an aromatic, aliphatic or non-polar residue |
| SITE | 223 |
|  | note = MISC_FEATURE - Xaa is an aliphatic or nonpolar residue |
| SITE | 226 |
|  | note = MISC_FEATURE - Xaa is an nonpolar or aliphatic residue |
| SITE | 228 |
|  | note = MISC_FEATURE - Xaa is an nonpolar or aliphatic residue |
| source | 1..252 |
|  | mol_type = protein |
|  | organism = synthetic construct |
| SEQUENCE: 145 |  |

```
MTXRLKXKVA XVTGGXLGXG LAXADKFVEE GAKVVITGRH XDVGXKAAXS IGGTDVXRFX   60
QHDXSDEAGW TXLFDTTEEA FXPVTTVVNN AGIXXXXSVE DTTTEXWXKL XSVNLDVFF  120
GTRLGXXRMK NKGLGASIIN MSSIXGXVGD PXLGAYXASK GAXRIMSKSA ALXCALXDYD 180
VRVNTVHPGY IXTXLVDXLX GAEEMXSXRX XTPXGHXGEP NDXAWXCXYL ASDESKFATG 240
AEFVVDGGYT AQ                                                    252
```

```
SEQ ID NO: 146          moltype = DNA   length = 939
FEATURE                 Location/Qualifiers
misc_feature            1..939
                        note = YDL ADH from Saccharomyces cervisiae
source                  1..939
                        mol_type = other DNA
                        organism = synthetic construct
SEQUENCE: 146
atgtctttc accaacagtt tttcacgctg aacaacggca ataaaatccc ggcgattgcc    60
atcatcggca ctggtacacg ttggtataaa aatgaagaaa ctgacgcgac cttctccaat  120
agtctggttg aacaaatcgt gtatgcgttg aaactgccgg ggattatcca catcgacgcc  180
gcggagattt atcgcaccta cccggaagtg ggtaaagcac tgtccctgac cgaaaagcct  240
cgtaacgcga tttttctgac ggataaatat tctccgcaga ttaaaatgag tgactccccct 300
gcggacggtc tggatttagc attgaagaaa atgggtacag attatgttga tttatatctg  360
ttacattccc cgtttgtttc gaaggaagtg aatggcttaa gcttagaaga ggcttggaaa  420
gatatggagc agttatacaa aagtggtaaa gctaaaaaca tcggggtttc caatttcgca  480
gtggaagacc tgcaacgtat cctgaaagtc gctgaagtta aacctcaggt caaccagatt  540
gagttctctc cgttcctgca aaaccaaaca ccaggcattt ataaattctg tcaggagcac  600
gatatcctgg tggaagcata ttctccgctg ggcccgctgc agaagaaaac cgcgcaggat  660
gacagccaac catttttga gtacgttcaa gaattgcagc aaaaatacat caaatccgag  720
gcccagatca tcctgcgctg ggtcactaaa cgcggtgtgc tgccagttac cacctcttca  780
aagcctcagc gcattagcga tgctcagaac ctgttttcct tcgacctgac agcggaagag  840
gttgataaaa tcacggagct gggtctggaa catgaaccgc tgcgcctgta ctggaataaa  900
ttgtatggca aatataacta cgccgcccag aaagtgtaa                         939
```

```
SEQ ID NO: 147          moltype = AA   length = 312
FEATURE                 Location/Qualifiers
REGION                  1..312
                        note = YDL ADH from Saccharomyces cervisiae
source                  1..312
                        mol_type = protein
                        organism = synthetic construct
SEQUENCE: 147
MSFHQQFFTL NNGNKIPAIA IIGTGTRWYK NEETDATFSN SLVEQIVYAL KLPGIIHIDA   60
AEIYRTYPEV GKALSLTEKP RNAIFLTDKY SPQIKMSDSP ADGLDLALKK MGTDYVDLYL  120
LHSPFVSKEV NGLSLEEAWK DMEQLYKSGK AKNIGVSNFA VEDLQRILKV AEVKPQVNQI  180
EFSPFLQNQT PGIYKFCQEH DILVEAYSPL GPLQKKTAQD DSQPFFEYVK ELSEKYIKSE  240
AQIILRWVTK RGVLPVTTSS KPQRISDAQN LFSFDLTAEE VDKITELGLE HEPLRLYWNK  300
LYGKYNYAAQ KV                                                     312
```

```
SEQ ID NO: 148          moltype = DNA   length = 1047
FEATURE                 Location/Qualifiers
misc_feature            1..1047
                        note = ADH from Rhodococcus erythropolis
source                  1..1047
                        mol_type = other DNA
                        organism = synthetic construct
SEQUENCE: 148
atgaaagcca ttcagtacac tcgtatcggt gcggaaccag aactgactga aatcccgaag    60
ccggaaccgg gcccgggcga agtactgctg gaagtcacgg cagctggcgt gtgccattcc  120
gatgatttca ttatgtctct gccggaagaa cagtacacct acggcctgcc gctgaccctg  180
ggtcatgaag tgctggtaa agttgccgca gttggcgaag tgttgaaggt tggatatt     240
gcaccaatg tggttgtgta cggcccatgg ggttgtggca actgttggca ttgcagtcag  300
ggcctggaga actattgctc ccgtgcgcag gaactggcgta ttaaccgcc tggtctgtgt  360
gctccggggg ctttgcaga atttatgatt gtcgactcac cacgtcattt ggtcccgatt  420
ggcgatttag accctgttaa aactgttccg ttgactgatg cgggcctgac cccataccat  480
gcaatcaaac gctccctgcc gaaactgcgc ggcggctctt atgcagtagt gatcggtacg  540
ggtggcctgg gccacgttgc tatccaactg ctgcgtcatt tatctgctgc aacggtgatc  600
gccttggacg tttctgccga taactggaa ctggctacca agtcggcgc acatgaagta   660
gtcctgtctg ataaagatgc agcggagaat gtgcgtaaaa ttactggtag ccaaggtgca  720
gctttggtgt tggattttgt gggctatcag cctaccattg acaccgccat ggcagtggcg  780
ggcgtgggct ctgacgtcac cattgttggt atcggtgatg gccaggcaca tgcgaaagtt  840
gggtttcttcc agagtcctta tgaggcatcg gttacggtac cttattgggg tctcgtaat   900
gaactgatcg aattgatcga tctgcgcat gctggtattt tcgacattgc cgttgagacc   960
ttctctttgg ataatggtgc agaggcctat cgtcgcctgg ctgcgggcac actgtcaggc 1020
cgtgcggtag tcgtcccggg cctgtaa                                     1047
```

```
SEQ ID NO: 149          moltype = AA   length = 348
FEATURE                 Location/Qualifiers
REGION                  1..348
                        note = ADH from Rhodococcus erythropolis
source                  1..348
                        mol_type = protein
```

```
                        organism = synthetic construct
SEQUENCE: 149
MKAIQYTRIG AEPELTEIPK PEPGPGEVLL EVTAAGVCHS DDFIMSLPEE QYTYGLPLTL    60
GHEGAGKVAA VGEGVEGLDI GTNVVVYGPW GCGNCWHCSQ GLENYCSRAQ ELGINPPGLG   120
APGALAEFMI VDSPRHLVPI GDLDPVKTVP LTDAGLTPYH AIKRSLPKLR GGSYAVVIGT   180
GGLGHVAIQL LRHLSAATVI ALDVSADKLE LATKVGAHEV VLSDKDAAEN VRKITGSQGA   240
ALVLDFVGYQ PTIDTAMAVA GVGSDVTIVG IGDGQAHAKV GFFQSPYEAS VTVPYWGARN   300
ELIELIDLAH AGIFDIAVET FSLDNGAEAY RRLAAGTLSG RAVVVPGL                348

SEQ ID NO: 150            moltype = DNA    length = 1047
FEATURE                   Location/Qualifiers
misc_feature              1..1047
                          note = YGL ADH from Saccharomyces cerevisiae
source                    1..1047
                          mol_type = other DNA
                          organism = synthetic construct
SEQUENCE: 150
atgaccacgg aaaaaaccgt agtgttcgtg tcaggcgcga ccggttttat tgctctgcac     60
gtggtagatg acctgctgaa aactggttac aaagtaattg gttccggtcg ttctcaggaa    120
aaaaatgacg gtttgctgaa gaagttcaag tccaacccga atctgagcat ggaaattgtg    180
gaagatattg cggcaccaaa cgccttcgat aaagtattcc agaaacatgg taaagaaatt    240
aaagtggtcc tgcatatcgc gtccccggtc catttcaaca ctaccgattt cgaaaaagac    300
ttactgatcc cggcgtaaa cggtaccaaa tctattttgg aagcaattaa gaactatgcc    360
gcagacaccg tggaaaaagt ggttattact tcatctgttg ccgcgttggc ctctccgggt    420
gatatgaaag ataccagctt cgtggttaac gaagaatcct ggaataaaga cacctgggaa    480
tcgtgtcagg cgaatgctgt gtccgcttat tgcggttcta aaaaattcgc agagaaaacg    540
gcgtgggact tcttggaaga aaccagagc agcattaaat ttactctgtc cacgattaac    600
ccaggcttcg ttttttggtcc gcagctgttc gccgactcct tgcgcaatgg tattaactct    660
agcagtgcga ttattgcgaa cctggtgtcg tataaattag gggataactt ctacaattat    720
agcggcccgt ttatcgacgt ccgtgacgtt tccaaagctc atctgctggc atttgagaaa    780
cctgaatgcg ccggtcagcg cctgtttctg tgcgaggata tgttctgttc ccaggaagcc    840
ctggacattc tgaacgaaga atttccacag ctgaagggca agatcgcaac gggcgaacct    900
ggcagcggct cgaccttcct gactaaaaat tgttgcaaat gcgacaatcg taaaactaaa    960
aacttgctgg gcttccagtt caacaaattc cgcgactgca ttgtcgatac tgcgtcccag   1020
ttgctggaag tgcaaagcaa aagctaa                                      1047

SEQ ID NO: 151            moltype = AA    length = 348
FEATURE                   Location/Qualifiers
REGION                    1..348
                          note = YGL ADH from Saccharomyces cerevisiae
source                    1..348
                          mol_type = protein
                          organism = synthetic construct
SEQUENCE: 151
MTTEKTVVFV SGATGFIALH VVDDLLKTGY KVIGSGRSQE KNDGLLKKFK SNPNLSMEIV    60
EDIAAPNAFD KVFQKHGKEI KVVLHIASPV HFNTTDFEKD LLIPAVNGTK SILEAIKNYA   120
ADTVEKVVIT SSVAALASPG DMKDTSFVVN EESWNKDTWE SCQANAVSAY CGSKKFAEKT   180
AWDFLEENQS SIKFTLSTIN PGFVFGPQLF ADSLRNGINS SSAIIANLVS YKLGDNFYNY   240
SGPFIDVRDV SKAHLLAFEK PECAGQRLFL CEDMFCSQEA LDILNEEFPQ LKGKIATGEP   300
GSGSTFLTKN CCKCDNRKTK NLLGFQFNKF RDCIVDTASQ LLEVQSKS                348

SEQ ID NO: 152            moltype = DNA    length = 939
FEATURE                   Location/Qualifiers
misc_feature              1..939
                          note = YPR ADH from Saccharomyces cerevisiae
source                    1..939
                          mol_type = other DNA
                          organism = synthetic construct
SEQUENCE: 152
atgccggcaa cgttaaaaaa cagcagtgct accttaaaat taaacacagg tgcgagcatt     60
cctgtcctgg ggttcggcac ctggcgctct gtcgataaca acggctatca tagtgtaatt    120
gcggcgctga aagcggggta ccgtcatatc gatgctgcgg ccatctatct gaatgaagaa    180
gaagtcggcc gtgcgatcaa ggactccggt gttcctcgtg aagaaatttt tattaccacc    240
aaactgtggg gcaccgaaca acgcgatcca gaagcagccc tgaacaaatc tctgaaacgt    300
ctgggtctgg actatgtgga cctgtatctg atgcactggc cggtccctct gaaaacagac    360
cgtgtaactg acggtaacgt cctgtgcatc ccgaccctgg aagatggcac cgtggacatc    420
gataccaaag agtggaattt tattaaaacc tgggaactga tgcaggaatt gccgaaaact    480
ggtaagacca aagccgtcgg tgtgtccaat ttttccatca acaatatcaa agaactgctg    540
gaatcgccaa ataacaaggt cgttccagca accaatcaga tcgaattca tccgttgctg    600
ccgcaggatg aattaatcgc cttttgtaaa gaaaaaggca ttgtggtcga agcatatagc    660
ccattcggct ccgctaacgc cccgctgctg aaagaacagg cgattatcga tatggccaaa    720
aagcacggcg tcgaaccggc gcaactgatt atcagctggt cgattcagcg cggttatgtg    780
gtattggcca agtccgtaaa tccggagcgt atcgtgtcga actttaagat ttttacccct    840
ccagaggatg atttcaaaac catctctaac ctgagcaaag tgcacggtac caaacgtgtc    900
gttgacatga aatgggctc atttccgatt tttcaataa                           939

SEQ ID NO: 153            moltype = AA    length = 312
FEATURE                   Location/Qualifiers
REGION                    1..312
```

```
                        note = YPR ADH from Saccharomyces cerevisiae
source                  1..312
                        mol_type = protein
                        organism = synthetic construct
SEQUENCE: 153
MPATLKNSSA TLKLNTGASI PVLGFGTWRS VDNNGYHSVI AALKAGYRHI DAAAIYLNEE    60
EVGRAIKDSG VPREEIFITT KLWGTEQRDP EAALNKSLKR LGLDYVDLYL MHWPVPLKTD   120
RVTDGNVLCI PTLEDGTVDI DTKEWNFIKT WELMQELPKT GKTKAVGVSN FSINNIKELL   180
ESPNNKVVPA TNQIEIHPLL PQDELIAFCK EKGIVVEAYS PFGSANAPLL KEQAIIDMAK   240
KHGVEPAQLI ISWSIQRGYV VLAKSVNPER IVSNFKIFTL PEDDFKTISN LSKVHGTKRV   300
VDMKWGSFPI FQ                                                      312

SEQ ID NO: 154          moltype = DNA  length = 1029
FEATURE                 Location/Qualifiers
misc_feature            1..1029
                        note = GRE ADH from Saccharomyces cervisiae
source                  1..1029
                        mol_type = other DNA
                        organism = synthetic construct
SEQUENCE: 154
atgtctgtgt tcgtgtcagg cgcgaatggt tttattgctc agcacatcgt agatctgctg    60
ctgaaagaag attacaaagt aattggttcc gcacgttctc aggaaaaagc tgaaaatttg   120
accgaagcct tcggtaacaa cccgaaattt agcatggaag tggtgcctga tattagcaaa   180
ctggatgcct tcgatcatgt attccagaaa catggtaaag atattaaaat cgtcctgcat   240
accgcgtccc cgttttgttt cgatattacc gattccgaac gtgacttact gatcccggcg   300
gtaaacggtg tcaaaggtat tttgcacagt attaagaaat atgccgcaga cagcgtggaa   360
cgcgtggttc tgacttcatc ttacgccgcg gtatttgata tggcgaagga aaacgataag   420
agcctgacct tcaacgaaga atcctggaat ccggcgacct gggaatcgtg tcagagtgat   480
ccggtgaacg cttattgcgg ttctaaaaaa ttcgcagaga aagcagcgtg ggaattcttg   540
gaagaaaacc gtgatagcgt gaaatttgag ctgacagcgg tcaacccagt ttacgttttt   600
ggtccgcaga tgttcgataa agatgttaaa aaacacttga acaccagctg cgaactggtg   660
aactctctga tgcatctgag ccctgaagat aaaattccgg aactgtttgg cggttacatc   720
gacgtccgtg acgttgcgaa agctcatctg gttgcatttc agaaacgtga aacaatcggt   780
cagcgcctga tcgtgtcgga ggcacgtttc acgatgcagg acgttctgga cattctgaac   840
gaagactttc cagtactgaa gggcaatatc ccggtcggca agcctggcag cggcgccacc   900
cataatactc tgggcgccac cctggacaat aaaaaaagca aaaaattgct gggcttcaaa   960
ttccgtaatc tgaaagagac tattgacgat actgcgtccc agatcctgaa attcgaaggt  1020
cgcatttaa                                                         1029

SEQ ID NO: 155          moltype = AA  length = 342
FEATURE                 Location/Qualifiers
REGION                  1..342
                        note = GRE ADH from Saccharomyces cervisiae
source                  1..342
                        mol_type = protein
                        organism = synthetic construct
SEQUENCE: 155
MSVFVSGANG FIAQHIVDLL LKEDYKVIGS ARSQEKAENL TEAFGNNPKF SMEVVPDISK    60
LDAFDHVFQK HGKDIKIVLH TASPPCFDIT DSERDLLIPA VNGVKGILHS IKKYAADSVE   120
RVVLTSSYAA VFDMAKENDK SLTFNEESWN PATWESCQSD PVNAYCGSKK FAEKAAWEFL   180
EENRDSVKFE LTAVNPVYVF GPQMFDKDVK KHLNTSCELV NSLMHLSPED KIPELFGGYI   240
DVRDVAKAHL VAFQKRETIG QRLIVSEARF TMQDVLDILN EDFPVLKGNI PVGKPGSGAT   300
HNTLGATLDN KKSKKLLGFK FRNLKETIDD TASQILKFEG RI                     342
```

KETOREDUCTASE POLYPEPTIDES FOR THE PRODUCTION OF (R)-3-HYDROXYTHIOLANE

1. CROSS REFERENCES TO RELATED APPLICATIONS

This application is a Continuation of co-pending U.S. patent application Ser. No. 17/080,676, filed Oct. 26, 2020, which is a Continuation of U.S. patent application Ser. No. 16/457,396, filed Jun. 28, 2019, now U.S. Pat. No. 10,851,397, which is a Continuation of U.S. patent application Ser. No. 15/902,301, filed Feb. 22, 2018, now U.S. Pat. No. 10,385,371, which is a Continuation of U.S. patent application Ser. No. 15/184,018, filed Jun. 16, 2016, now U.S. Pat. No. 9,932,615, which is a Continuation of U.S. patent application Ser. No. 14/597,996, filed Jan. 15, 2015, now U.S. Pat. No. 9,394,552, which is a Continuation of U.S. patent application Ser. No. 13/525,048, filed Jun. 15, 2012, now U.S. Pat. No. 8,962,285, which claims benefit under 35 U.S.C. § 120 to U.S. patent application Ser. No. 13/110,789, filed May 18, 2011, now U.S. Pat. No. 8,227,229, which claims benefit under 35 U.S.C. § 120 to U.S. patent application Ser. No. 12/197,286, filed Aug. 24, 2008, now U.S. Pat. No. 7,977,078, and under 35 U.S.C. § 119(e) of application Ser. No. 60/957,974, filed Aug. 24, 2007, the contents of each of which are incorporated herein by reference.

2. TECHNICAL FIELD

The present disclosure relates to engineered polypeptides and uses of the polypeptides.

3. REFERENCE TO SEQUENCE LISTING, TABLE OR COMPUTER PROGRAM

The Sequence Listing submitted herewith under 37 C.F.R. § 1.821 via EFS-Web in a computer readable form (CRF) as file name CX2-047USD1C7_Corrected_st26.xml is herein incorporated by reference. The electronic copy of the Sequence Listing was created on Oct. 21, 2022, with a file size of 320 kilobytes. This Sequence Listing is identical except for minor formatting corrections to file CX2-047USD1C7_st26.txt.xml created on Jul. 20, 2022, with a file size of 324 kilobytes and 376247-016.txt created on Aug. 24, 2008, with a file size of 272 kilobytes, the latter of which was incorporated by reference in the parent U.S. application Ser. No. 12/197,286.

4. BACKGROUND

Enzymes belonging to the ketoreductase (KRED) or carbonyl reductase class (EC1.1.1.184) are useful for the synthesis of optically active alcohols from the corresponding prostereoisomeric ketone substrate. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes, and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes can be found in a wide range of bacteria and yeasts (for reviews: Kraus and Waldman, Enzyme catalysis in organic synthesis Vols. 1&2.VCH Weinheim 1995; Faber, K., Biotransformations in organic chemistry, 4th Ed. Springer, Berlin Heidelberg New York. 2000; Hummel and Kula, 1989, *Eur. J. Biochem.* 184:1-13). Several KRED genes and enzyme sequences have been reported, e.g., *Candida magnoliae* (Genbank Acc. No. JC7338; GI:11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto substrates to chiral alcohol products. These applications can employ whole cells expressing the ketoreductase for biocatalytic ketone and aldehyde reductions, or purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc., is used in conjunction with the ketoreductase. Examples using ketoreductases to generate useful chemical compounds include asymmetric reduction of 4-chloroacetoacetate esters (Zhou, *J. Am. Chem. Soc.*, 1983, 105:5925-5926; Santaniello, *J. Chem. Res*. (S) 1984: 132-133; U.S. Pat. Nos. 5,559,030; 5,700,670 and 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction pyrrolotriazine-based compounds (e.g., US application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carryout conversion of various keto and aldehyde substrates to its corresponding chiral alcohol products.

5. SUMMARY

The present disclosure provides ketoreductase polypeptides having the ability to reduce 3-ketothiolane (hereafter referred to as "the substrate") to (R)-3-hydroxythiolane (hereafter referred to as "the product"), the polynucleotides encoding such polypeptides, and methods for using the polypeptides. Generally, the engineered ketoreductase polypeptides of the disclosure have an improved property as compared to the naturally-occurring wild-type ketoreductase enzymes obtained from *Lactobacillus kefir* ("*L. kefir*"; SEQ ID NO:4), *Lactobacillus brevis* ("*L. brevis*"; SEQ ID NO:2), and *Lactobacillus minor* ("*L. minor*"; SEQ ID NO:142) in converting the defined keto substrate to the corresponding chiral alcohol product. Improvements in enzyme activity can include increases in stereoselectivity, enzymatic activity, thermostability, solvent stability, reduced product inhibition, or combinations thereof.

In some embodiments, the ketoreductase polypeptides of the disclosure comprise an amino acid sequence in which the amino acid the residue corresponding to position 145 of a reference sequence of SEQ ID NO:2, 4 or 142 is not an acidic residue, i.e., glutamic acid or aspartic acid. As such, the residue corresponding to position 145 is a non-acidic residue. In some embodiments, the ketoreductase polypeptides of the disclosure have an amino acid sequence in which the residue corresponding to position 145 is a polar residue. In some embodiments, this residue corresponding to X145 is a serine.

In some embodiments, the ketoreductase polypeptides of the disclosure have an amino acid sequence that is at least about 85%, 86%, 87%, 88%, 89%, 90%, 91%, 92%, 93%, 94%, 95%, 96%, 97%, 98%, 99%, or more identical to a reference sequence based on SEQ ID NO:2 or SEQ ID NO:4 or SEQ ID NO:142 (or a region or domain thereof, such as residues 90-211) having at the residue corresponding to X145 a serine, with the proviso that the ketoreductase polypeptide amino acid sequence has at the residue corresponding to X145 a polar residue. In some embodiments, the residue corresponding to residue X145 is a serine. In some embodiments, the ketoreductase polypeptide is based on the sequence formulas of SEQ ID NO:143, 144, or 145, or a domain thereof, such as residues 90-211, in which the residue corresponding to X145 is a polar residue, particularly serine. In some embodiments, the ketoreductase polypeptides can additionally have one or more amino acid residue differences in the amino acid sequence, or the defined domain or region, as compared to the reference sequence, such as the reference sequences of SEQ ID NO:4, 2, or 142. In some embodiments, the amino acid sequence differences in the domain can comprise non-conservative, conservative, as well as a combination of non-conservative and conservative amino acid substitutions. Various amino acid residue positions where such changes can be made are described herein.

In some embodiments, the ketoreductase polypeptides described herein are capable of stereoselectively reducing the substrate to the product with at a higher stereomeric excess than the wildtype enzyme from *L. kefir* (i.e., SEQ ID NO:4). In some embodiments, the ketoreductase polypeptides described herein are capable of stereoselectively reducing the substrate ketothiolane to the product (R)-3-hydroxythiolane with at least about 70% stereomeric excess.

In some embodiments, the disclosure provides highly stereoselective ketoreductase polypeptides that can reduce the substrate to the product in greater than about 90% stereomeric excess (s.e.). Exemplary ketoreductase polypeptides with such high stereoselectivity include, but are not limited to, the polypeptides comprising the amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, and 134.

In some embodiments, the disclosure provides stereoselective ketoreductase polypeptides that can reduce the substrate to the product in greater than about 98% s.e. Exemplary polypeptides with such stereoselectivity include, but are not limited to, the polypeptides comprising the amino acid sequences corresponding to SEQ ID NO: 6, 8, 10, 18, 20, 22, 24, 26, 28, 30, 34, 36, 38, 40, 42, 50, 52, 54, 58, 62, 66, 70, 72, 76, 78, 80, and 134.

In some embodiments, the engineered ketoreductase polypeptide can have increased enzymatic activity as compared to the wild-type ketoreductase enzyme in reducing the defined keto substrate to the product. The amount of the improvement can range from 1.5 times the enzymatic activity of the corresponding wild-type ketoreductase enzyme, to as much as 2 times, 5 times, 10 times, 20 times, 25 times, 50 times, 75 times, 100 times, or more enzymatic activity. In specific embodiments, the engineered ketoreductase enzyme exhibits improved enzymatic activity in the range of 1.5 to 50 times, 1.5 to 100 times greater than that of the wild-type ketoreductase enzyme. Exemplary polypeptides that are capable of converting the substrate to the product at a rate that is improved over wild-type enzyme, include but are not limited to, polypeptides comprising the amino acid sequences corresponding to SEQ ID NO: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, and 134.

In some embodiments, the disclosure provides ketoreductase polypeptides that have improved activity and stability over the wild-type enzyme, and can reduce the substrate to the product in greater than about 95% s.e. Exemplary polypeptides with such capabilities include, but are not limited to, polypeptides comprising the amino acid sequences corresponding to SEQ ID NO: 6, 8, 12, 14, 22, 24, 26, 30, 32, 38, 42, 44, 46, 50, 52, 56, 58, 60, 64, 66, 68, 70, 74, 76, 78, 80, 82, 86, 88, 90, 92, 104, 106, 110, 112, and 134.

In some embodiments, the ketoreductase polypeptides of the disclosure are improved as compared to wild-type with respect to their thermostability, as determined by an increase in the rate of enzymatic activity as compared to wild-type under high temperatures. Exemplary ketoreductase polypeptides with improved stability, include but are not limited to, polypeptides comprising amino acid sequences corresponding to SEQ ID NO: 6, 8, 12, 14, 22, 24, 26, 32, 34, 36, 38, 42, 44, 46, 50, 52, 56, 58, 60, 64, 66, 68, 70, 74, 76, 78, 80, 82, 86, 88, 90, 92, 104, 106, 110, 112, 124, and 134.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. Exemplary polynucleotides include, but are not limited to, the nucleotide sequences corresponding to SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and 133.

In another aspect, the present disclosure provides host cells comprising the polynucleotides and/or expression vectors for purposes of manipulation and expression of the ketoreductase polypeptides. The host cells may be *L. kefir*, *L. brevis*, or *L. minor*, or they may be a different organism. The host cells can be used for the expression and isolation of the engineered ketoreductase enzymes described herein, or, alternatively, they can be used directly for the conversion of the 3-ketothiolane substrate to the chiral (R)-3-hydroxythiolane product.

Whether carrying out the method with whole cells, cell extracts or purified ketoreductase enzymes, a single ketoreductase enzyme may be used or, alternatively, mixtures of two or more ketoreductase enzymes may be used.

As noted above, the ketoreductase enzymes described herein are capable of catalyzing the reduction reaction of the keto group in the compound of structural formula (I), 3-ketothiolane,

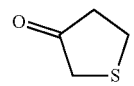

(I)

to the corresponding chiral alcohol product of structural formula (II), (R)-3-hydroxythiolane,

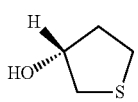

(II)

As such, in some embodiments, the present disclosure provides a method for reducing 3-ketothiolane ("the substrate") to (R)-3-hydroxythiolane ("the product"), which method comprises contacting or incubating the substrate with a ketoreductase polypeptide of the disclosure under reaction conditions suitable for reducing or converting the substrate to the product. In some embodiments of this method, the substrate is reduced to the product with a stereomeric excess at least greater than about 65% or at least greater than wild-type.

In some embodiments of this method, the substrate is reduced to the product in greater than about 90% s.e., wherein the ketoreductase polypeptides comprise amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, and 134.

In some embodiments of this method, the substrate is reduced to the product in greater than about 98% s.e., wherein the ketoreductase polypeptides comprise an amino acid sequences corresponding to SEQ ID NO: 6, 8, 10, 18, 20, 22, 24, 26, 28, 30, 34, 36, 38, 40, 42, 50, 52, 54, 58, 62, 66, 70, 72, 76, 78, 80, and 134.

In some embodiments of this method for reducing the substrate to the product, the substrate is reduced to the product at an improved rate of at least 1.5 times, 2 times, 3 times 4 times, 5 times, 10 times, 20 times or more as compared to the wild-type enzyme (SEQ ID NO:4), wherein the ketoreductase polypeptides comprise amino acid sequences corresponding to SEQ ID NO: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, and 134.

In some embodiments, the methods relate to use of the ketoreductase polypeptides in the synthesis of other compounds, such as drug compounds. In some embodiments, the methods relate to use of the ketoreductase polypeptides in the synthesis of antibiotic sulopenem (CP-70,429), having the following structural formula (III):

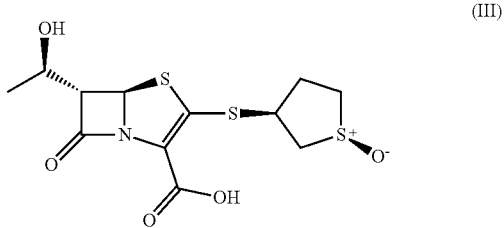

(III)

Thus, in some embodiments, in a method for the synthesis of the antibiotic of structural formula (III) (i.e., CP-70,429), a step in the method can comprise contacting the substrate of formula (I) with any of the ketoreductases described herein, under reaction conditions suitable for converting or reducing the substrate of structural formula (I) to the product of structural formula (II). The compound of structural formula (II) in stereomeric excess of at least 70%, 80%, 90%, 95%, 96%, 97%, 98%, or 99% or more can be used in the preparation of the compound of formula (III).

6. BRIEF DESCRIPTION OF THE DRAWINGS

FIG. 1 illustrates the role of ketoreductases (KRED) in the conversion of the substrate compound of formula (I), 3-ketothiolane, to the corresponding chiral alcohol product of formula (II), (R)-3-hydroxythiolane. In this reaction, the substrate is reduced biocatalytically to the corresponding (R)-alcohol. This reduction uses a KRED of the disclosure and a co-factor such as NADPH. A glucose dehydrogenase (GDH) can be used to covert/recycle NADP$^+$ to NADPH. Glucose is converted to gluconic acid, which in turn is converted to its sodium salt (sodium gluconate) with the addition of sodium hydroxide. Example 9 provides a non-limiting method for conducting the reaction.

7. DETAILED DESCRIPTION

7.1 Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol. More specifically, the ketoreductase polypeptides described herein are capable of stereoselectively reducing the compound of formula (I), supra to the corresponding product of formula (II), supra. The polypeptide typically utilizes a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

In some embodiments, a "reference sequence" can be based on a primary amino acid sequence, where the reference sequence is a sequence that can have one or more changes in the primary sequence. For instance, a reference sequence "based on SEQ ID NO:4 having at the residue corresponding to X145 a serine" refers to a reference sequence in which the corresponding residue at X145 in SEQ ID NO:4 has been changed to a serine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, amino acid residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. This can also be referred to as stereomeric excess (s.e.). Where the stereoisomers are diastereoisomers, the stereoselectivity is referred to as diastereoselectivity, the fraction (typically reported as a percentage) of one diastereomer in a mixture of two diastereomers.

"Highly stereoselective" refers to a ketoreductase polypeptide that is capable of converting or reducing the substrate to the corresponding (R)-product with at least about 85% stereomeric excess.

"Improved enzyme property" refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, and stereoselectivity (including enantioselectivity).

"Increased enzymatic activity" refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, or more enzymatic activity than the naturally occurring ketoreductase or another engineered ketoreductase from which the ketoreductase polypeptides were derived. In specific embodiments, the engineered ketoreductase enzyme exhibits improved enzymatic activity in the range of 1.5 to 50 times or 1.5 to 100 times greater than that of the parent ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}$ $s^{-1}$). Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH (see Example 6) due to its oxidation with the concomitant reduction of a ketone or aldehyde to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic reduction of the substrate to the corresponding product. "Percent conversion" refers to the percent of the substrate that is reduced to the product within a period of time under specified conditions. Thus, the "enzymatic activity" or "activity" of a ketoreductase polypeptide can be expressed as "percent conversion" of the substrate to the product.

"Thermostable" refers to a ketoreductase polypeptide that maintains similar activity (more than 60% to 80% for example) after exposure to elevated temperatures (e.g., 40-80° C.) for a period of time (e.g., 0.5-24 hrs) compared to the untreated enzyme.

"Solvent stable" refers to a ketoreductase polypeptide that maintains similar activity (more than e.g 60% to 80%) after exposure to varying concentrations (e.g., 5-99%) of solvent (e.g., isopropylalcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

"pH stable" refers to a ketoreductase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a ketoreductase polypeptide that are both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO: 134 was obtained by artificially evolving, over multiple generations the gene encoding the L. kefir ketoreductase enzyme of SEQ ID NO:4. Thus, this engineered ketoreductase enzyme is "derived from" the wild-type ketoreductase of SEQ ID NO.: 4.

"Hydrophilic Amino Acid or Residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine". The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. The table below shows exemplary conservative substitutions.

| Residue | Possible Conservative Mutations |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions in an amino acid sequence can comprise removal of 1 or more amino acids, 2 or more amino acids, 3 or more amino acids, 4 or more amino acid, 5 or more amino acids, 6 or more amino acids, 8 or more amino acids, 10 or more amino acids, 15 or more amino acids, or 20 or more amino acids, up to 10% of the total number of amino acids, up to 15% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids as compared to a reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length ketoreductase polypeptide. In some embodiments, the full length ketoreductase can be a full length engineered or wild type ketoreductase (e.g., SEQ ID NO:2 and 4).

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., 1989, *Methods Enzymology* 168: 761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra; Suggs et al., 1981, In *Developmental Biology Using Purified Genes* (Brown et al., eds.), pp. 683-693, Academic Press; and Wetmur, 1991, *Crit Rev Biochem Mol Biol* 26:227-259; all publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018 M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production in the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O., 1998, *Bioinformatics* 14:372-73; Stenico et al., 1994, *Nucleic Acids Res.* 222437-46; Wright, F., 1990, *Gene* 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polynucleotide or polypeptide of interest. Each control sequence may be native or foreign to the nucleic acid sequence encoding a polypeptide. Such control sequences include, but are not limited to, a leader sequence, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed in a functional relationship (i.e., at a position relative to) with a polynucleotide or polypeptide of interest, such as the coding sequence in the DNA sequence, such that the control sequence directs or regulates the expression of a polynucleotide and/or polypeptide.

"Promoter sequence" is a nucleic acid sequence that is recognized by a host cell for expression of a polynucleotide of interest, such as a coding region. Generally, the promoter sequence contains transcriptional control sequences, which mediate the expression of a polynucleotide of interest. The promoter may be any nucleic acid sequence which shows transcriptional activity in the host cell of choice, including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD+ or NADP+, respectively, are known in the art and may be used in the methods described herein.

7.2 Ketoreductase Enzymes

The present disclosure provides engineered ketoreductase ("KRED") enzymes that are capable of stereoselectively reducing or converting 3-ketothiolane ("the substrate") of structural formula (I):

to (R)-3-hydroxythiolane ("the product") of structural formula (II):

and having an improved property when compared with the naturally-occurring, wild-type KRED enzyme obtained from *L. kefir* (SEQ ID NO:4), *L. brevis* (SEQ ID NO:2) or *L. minor* (SEQ ID NO:142), or when compared with other engineered ketoreductase enzymes. Enzyme properties for which improvement is desirable include, but are not limited to, enzymatic activity, thermal stability, pH activity profile, cofactor requirements, refractoriness to inhibitors (e.g., product inhibition), stereospecificity, stereoselectivity, and solvent stability. The improvements can relate to a single enzyme property, such as enzymatic activity, or a combination of different enzyme properties, such as enzymatic activity and stereoselectivity.

The present disclosure provides engineered ketoreductase ("KRED") enzymes that are capable of stereoselectively reducing a defined keto substrate to its corresponding alcohol product and having an improved property when compared with the naturally-occurring, wild-type KRED enzyme obtained from *L. kefir* (SEQ ID NO:2) or *L. brevis* (SEQ ID NO:4) or *L. minor* (SEQ ID NO:142), or when compared with other engineered ketoreductase enzymes. The ketoreductase polypeptides of the disclosure have the requirement that the residue corresponding to position 145 of SEQ ID NO:2 or 4 or 142 is not an acidic residue. In some embodiments, the ketoreductase polypeptides have, as compared to the *L. kefir* or *L. brevis* or *L. minor* KRED sequences of SEQ ID NO:2 or 4 or 142, at the residue corresponding to position 145 a polar residue. In some embodiments, the ketoreductase polypeptides have, as compared to the *L. kefir* or *L. brevis* or *L. minor* KRED sequences of SEQ ID NO:2 or 4 or 142, at the residue corresponding to position 145 a serine.

In some embodiments, as noted above, the engineered ketoreductase with improved enzyme activity is described with reference to *L. kefir* ketoreductase of SEQ ID NO:4, *L. brevis* ketoreductase of SEQ ID NO:2, *L. minor* of SEQ ID NO:142, or an engineered ketoreductase. The amino acid residue position is determined in these ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. Where the amino acid residues at the same residue position differ between the ketoreductases, the different residues are denoted by an "/" with the arrangement being, for example, "kefir residue/brevis residue/minor." In some embodiments, a substitution mutation, which is a replacement of an amino acid residue in a corresponding residue of a reference sequence, for example the wildtype ketoreductase of SEQ ID NO:2, SEQ ID NO:4, or SEQ ID NO:142 with a different amino acid residue is denoted by the symbol "→".

Herein, mutations are sometimes described as a mutation "to a" type of amino acid. For example, residue X7 can be mutated glycine "to a" serine residue. But the use of the phrase "to a" does not exclude mutations from one amino acid of a class to another amino acid of the same class. For example, residue X7 can be mutated from a glycine to an arginine.

The polynucleotide sequence encoding the naturally occurring ketoreductase (also referred to as "ADH" or "alcohol dehydrogenase") of *L. kefir, L. brevis*, or of *L. minor*, and thus the corresponding amino acid sequences, are available as Genbank accession no. AAP94029 GI:33112056 or SEQ ID NO:3 for *L. kefir*; Genbank accession no. CAD66648 GI:28400789 or SEQ ID NO:1 for *L. brevis*; and SEQ ID NO:141 for *L. minor*).

In some embodiments, the ketoreductase polypeptides herein can have a number of modifications to the reference sequence (e.g., naturally occurring polypeptide or an engineered polypeptide) to result in an improved ketoreductase property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 15% of the total number of amino acids, up to 20% of the total number of amino acids, or up to 30% of the total number of amino acids of the reference polypeptide sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35 or about 40 amino acid residues. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 amino acid substitutions of the reference sequence. In some embodiments, the number of substitutions can be 1, 2, 3, 4, 5, 6, 7, 8, 9, 10, 11, 12, 14, 15, 16, 18, 20, 22, 24, 26, 30, 35 or about 40 amino acid residues.

In some embodiments, the improved property (as compared to wild-type or another engineered polypeptide) of the ketoreductase polypeptide is with respect to an increase of its stereoselectivity for reducing or converting 3-ketothiolane substrate to (R)-3-hydroxythiolane. In some embodiments, the ketoreductase polypeptide is capable of stereoselectivey reducing the substrate to the product with a percent stereomeric excess of at least about 65%, 70%, 75%, 85%, 86%, 87%, 88%, 89%, 90%, 91%, 92%, 93%, 94%, 95%, 96%, 97%, 98%, 99%, 99.9%, or 99.99%.

In some embodiments, the ketoreductase polypeptide is capable of stereoselectively reducing the substrate to the product with a percent stereomeric excess (s.e.) that is improved as compared to the wild-type *L. kefir* or *L. brevis* or *L. minor* KRED (SEQ ID NO:4 or 2 or 142). In some embodiments, the ketoreductase polypeptide is capable of stereoselectively reducing the substrate to the product with a percent stereomeric excess that is at least about 70%.

In some embodiments, the ketoreductase polypeptides of the disclosure are highly stereoselective in that the keductases can reduce the substrate to the product in greater than about 90% stereomeric excess (s.e.). Exemplary ketoreductase polypeptides with such high stereoselectivity include, but are not limited to, the polypeptides comprising the amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, and 134.

In some embodiments, the ketoreductase polypeptides of the disclosure are improved as compared to wild-type (SEQ ID NO:4) with respect to their rate of enzymatic activity, i.e., their rate or ability of converting the substrate to the product. Exemplary polypeptides that are capable of converting the substrate to the product at a rate that is improved over wild-type, include but are not limited to, polypeptides comprising the amino acid sequences corresponding to SEQ ID NO: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, and 134.

In some embodiments, the ketoreductase polypeptides of the disclosure are highly stereoselective and can reduce the substrate to the product in greater than about 98% s.e. Exemplary polypeptides with such stereoselectivity include, but are not limited to, the polypeptides comprising the amino acid sequences corresponding to SEQ ID NO: 6, 8, 10, 18, 20, 22, 24, 26, 28, 30, 34, 36, 38, 40, 42, 50, 52, 54, 58, 62, 66, 70, 72, 76, 78, 80, and 134.

In some embodiments, the ketoreductase polypeptides of the disclosure are improved as compared to wild-type with respect to their thermostability, as determined by an increase in the rate of enzymatic activity as compared to wild-type under high temperatures. Exemplary ketoreductase polypeptides with improved stability, include but are not limited to, polypeptides comprising amino acid sequences corresponding to SEQ ID NO: 6, 8, 12, 14, 22, 24, 26, 32, 34, 36, 38, 42, 44, 46, 50, 52, 56, 58, 60, 64, 66, 68, 70, 74, 76, 78, 80, 82, 86, 88, 90, 92, 104, 106, 110, 112, 124, and 134.

In some embodiments, the ketoreductase polypeptides of the disclosure have improved activity and stability over wild-type, and can reduce the substrate to the product in greater than about 95% s.e. Exemplary polypeptides with such capabilities include, but are not limited to, polypeptides comprising amino acid sequences corresponding to SEQ ID NO: 6, 8, 12, 14, 22, 24, 26, 30, 32, 38, 42, 44, 46, 50, 52, 56, 58, 60, 64, 66, 68, 70, 74, 76, 78, 80, 82, 86, 88, 90, 92, 104, 106, 110, 112, and 134.

In some embodiments, the ketoreductases of the disclosure are capable of reducing or converting at least 100 g/L of ketothiolane to the corresponding product in less than 24 hrs (e.g., about 20-24 hours) at room temperature with about 0.8-1.0 g/L of the ketoreductase polypeptide. Exemplary polypeptides with such capabilities, include, but are not limited to polypeptides comprising amino acid sequences corresponding to SEQ ID NO: 6, 8, 10, 12, 14, 18, 20, 22, 24, 26, 30, 32, 38, 40, 42, 44, 46, 48, 50, 52, 54, 56, 58, 60, 64, 66, 68, 70, 74, 76, 78, 80, 82, 86, 88, 90, 92, 104, 106, 110, 112, 126, 130, and 134.

In some embodiments, the ketoreductases of the disclosure are capable of reducing or converting at least 100 g/L of ketothiolane to product in less than 20 hrs (e.g., 12-20 hrs) at room temperature with about 0.8-1.0 g/L of the ketoreductase polypeptide. Exemplary polypeptides with such capabilities, include, but are not limited to SEQ ID NO: 26, 44, 68, and 104.

Table 2 below provides exemplary ketoreductases. All sequences below are derived from the wild-type *L. kefir* ketoreductase sequences (SEQ ID NO: 3 and 4) unless otherwise specified. Each of the polypeptide sequences in Table 2 are encoded by the nucleotide sequence having the SEQ ID NO that is one less than the number in the Table, i.e., the polypeptide of SEQ ID NO:4 is encoded by the nucleotide sequence of SEQ ID NO:3.

TABLE 2

List of Sequences and Properties

| SEQ ID NO | Mutations as Compared to SEQ ID NO: 4 | Stereo-selectivity | Activity | Stability |
|---|---|---|---|---|
| 4 | None | 0 | 0 | 0 |
| 120 | N157S | 0 | 0 | 0 |
| 116 | E145D | 0 | 0 | 0 |
| 122 | G53V N157S | 0 | 0 | 0 |
| 114 | N157S V228A | + | 0 | 0 |
| 118 | A94T I126V N157S | + | 0 | 0 |
| 132 | K8R I23F A94T V95A R108H N157S | + | 0 | 0 |
| 84 | I11T A94T N157S | + | 0 | 0 |
| 98 | E145S | ++ | 0 | 0 |
| 124 | A41V K49R Q127R F147L E200K I217F | 0 | ++ | + |
| 102 | E145S N157T | +++ | 0 | 0 |
| 90 | G117S E145S | +++ | + | + |
| 16 | G7S E145S I223V | +++ | + | 0 |
| 100 | E145S I217F | +++ | 0 | 0 |
| 108 | E145S M214V | +++ | 0 | 0 |
| 128 | T16A I57V E145S | +++ | 0 | 0 |
| 96 | E145S M214T | +++ | 0 | 0 |
| 130 | T16A E145S | +++ | + | 0 |
| 126 | I19V E145S | +++ | + | 0 |
| 104 | K72R G117S E145S N157T I223V | +++ | ++ | + |
| 88 | G117S E145S N157T | +++ | + | + |
| 106 | K49R R108H G117S E145S N157T I223V | +++ | + | + |
| 14 | G7S R108H G117S E145S N157T | +++ | + | + |
| 86 | R108H G117S E145S N157T K192R I223V | +++ | + | + |
| 44 | G7S R108H G117S E145S N157T I223V | +++ | ++ | + |
| 92 | G117S E145S N157T K192R | +++ | + | + |
| 112 | E45G R108H G117S E145S N157T K192R D198G I223V | +++ | + | + |
| 94 | G117S E145S T152M N157T | +++ | 0 | − |
| 12 | G7S G117S E145S N157T | +++ | + | + |
| 56 | G7S I57V K97E R108H G117S E145S N157T I223V | +++ | + | + |
| 110 | E45G R108H G117S E145S N157T I223V | +++ | + | + |
| 36 | G7S A94T R108H G117S E145S N157T I223V | ++++ | 0 | + |
| 46 | G7S R108H G117S E145S N157T K192E I223V | +++ | + | + |
| 68 | G7S K49R L111M G117S E145S N157T D173G I223V | +++ | ++ | + |

TABLE 2-continued

List of Sequences and Properties

| SEQ ID NO | Mutations as Compared to SEQ ID NO: 4 | Stereo-selectivity | Activity | Stability |
|---|---|---|---|---|
| 48 | G7S R108H G117S E145S N157T K192E I217F I223V | +++ | + | − |
| 74 | G7S T16G R108H G117S E145S N157T I223V | +++ | + | + |
| 82 | G7H R108H G117S E145S N157T I223V | +++ | + | + |
| 42 | G7S A94T K97L R108H G117S E145S N157T I223V I226L | ++++ | + | + |
| 24 | G7S A94T S96P R108H G117S E145S N157T I223V | ++++ | + | + |
| 34 | G7S A94T S96A R108H G117S E145S N157T I223V | ++++ | 0 | + |
| 38 | G7S A94T R108H G117S E145S N157T M206Q I223V | ++++ | + | + |
| 32 | G7S A94T S96E R108H G117S E145S N157T I223V | +++ | + | + |
| 8 | G7N A94T E106D R108H G117S E145S N157T I223V | ++++ | + | + |
| 134 | D3Y G7S A94T R108H G117S E145S N157T I223V | ++++ | + | + |
| 6 | G7S A94T R108H G117S E145S N157T Q208H I223V | ++++ | + | + |
| 26 | G7S A94T S96P R108H G117S E145S N157T M206Q I223V | +++++ | ++ | + |
| 72 | G7S T16G A94T S96P R108H G117S E145S N157T M206Q I223V | +++++ | 0 | − |
| 18 | G7S A94T S96P R108H G117S E145S F147L N157T P194L I223V | ++++ | + | 0 |
| 20 | G7S A64T A94T S96P R108H G117S E145S N157T I223V | ++++ | + | 0 |
| 54 | G7S A94T S96P R108H G117S E145S N157T I217F I223V | ++++ | + | 0 |
| 10 | G7S A94T R108H G117S E145S N157T K177R M206Q Q208R I223V | ++++ | + | 0 |
| 40 | G7S A94T K97R R108H G117S E145S N157T M206Q I223V | ++++ | + | 0 |
| 52 | G7S R108H G117S E145S N157T M206Q I223V | ++++ | + | + |
| 50 | G7S S96P R108H G117S E145S N157T M206Q I223V | ++++ | + | + |
| 76 | G7S T16G S96P R108H G117S E145S N157T M206Q I223V | ++++ | + | + |
| 80 | G7S T16V A94T S96P R108H G117S E145S N157T M206Q I223V | +++++ | + | + |
| 78 | G7S T16G A94V S96P R108H G117S E145S N157T M206Q I223V | ++++ | + | + |
| 30 | G7S A94T S96P R108H G117S E145S N157T P194G M206Q I223V | +++++ | + | + |
| 28 | G7S A94T S96P R108H G117S E145S N157T P194D M206Q I223V | +++++ | 0 | 0 |
| 22 | G7S A94T S96P R108H G117S E145S N157T P194N M206Q I223V | +++++ | + | + |
| 60 | G7S K49R A94T L111M G117S E145S N157T D173G I223V | +++ | + | + |
| 64 | G7S K49R S96P L111M G117S E145S N157T D173G I223V | +++ | + | + |
| 70 | G7S K49R L111M G117S E145S N157T D173G M206Q I223V | ++++ | + | + |
| 62 | G7S K49R A94T L111M G117S E145S N157T D173G M206Q I223V | ++++ | 0 | 0 |
| 66 | G7S K49R S96P L111M G117S E145S N157T D173G M206Q I223V | ++++ | + | + |
| 58 | G7S K49R A94T S96P L111M G117S E145S N157T D173G M206Q I223V | +++++ | + | + |

In Table 2 above, in the stereoselectivity column, "0" indicates about 61.0-71.9% s.e. for the product (R)-3-hydroxythiolane, "+" indicates about 80.0-89.9% s.e. for the product, "++" indicates about 90.0-94.9% s.e. for the product, "+++" indicates about 95.0-97.9% s.e. for the product, "++++" indicates about 98.0-98.0% s.e. for the product, and "+++++" indicates about greater than 99.0% s.e. for the product. In the activity column, "0" indicates that 1.0-4.0 g/L of KRED is needed for complete conversion of 100 g/L of ketothiolane at room temperature in more than 24 hours; "+" indicates that 0.8-1.0 g/L of KRED is needed for complete conversion of 100 g/L of ketothiolane at room temperature within 20-24 hours; and "++" indicates that 0.8-1.0 g/L of KRED is needed for complete conversion of 100 g/L of ketothiolane at room temperature within 12-20 hours. In the stability column, "−" indicates the polypeptide exhibits thermostabilty properties worse than wild-type; "0" indicates the polypeptide exhibits thermostability properties similar to wild-type; "+" indicates the polypeptide exhibits improved thermostability as compared to wild-type; and "++" indicates the polypeptide exhibits even more improved thermostability as compared to wild-type.

In some embodiments, an improved ketoreductase polypeptides herein comprises an amino acid sequence that is at least about 85%, 86%, 87%, 88%, 89%, 90%, 91%, 92%, 93%, 94%, 95%, 96%, 97%, 98%, 99% or more identical as compared to a reference sequence based on SEQ ID NO: 2, 4 or 142 in which the amino acid residue corresponding to position 145 is a polar residue, particularly a serine, with the proviso that the ketoreductase polypeptides have at the residue corresponding to position 145 a polar residue, particularly a serine. In some embodiments, the ketoreductase polypeptides can have one or more residue differences at other amino acid residues as compared to the reference sequence. The differences can include substitutions, deletions, and insertions as compared to the reference sequence. The differences can be non-conservative substitutions, conservative substitutions, or a combination of non-conservative and conservative substitutions. In some embodiments, these ketoreductase polypeptides can have optionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 differences at other amino acid residues. In some embodiments, the number of differences with the reference sequence can be 1, 2, 3, 4, 5, 6, 7, 8, 9, 10, 11, 12, 14, 15, 16, 18, 20, 22, 24, 26, 30, 35 or about 40 differences at other amino acid residues. In some embodiments, the differences comprise conservative mutations as compared to the reference sequence.

In some embodiments, an improved ketoreductase polypeptide comprises an amino acid sequence that corresponds to the sequence formulas as laid out in SEQ ID NO:143 or SEQ ID NO:144 or SEQ ID NO:145, or a domain thereof, such as residues 90-211. SEQ ID NO:145 is based on the wild-type amino acid sequence of the *L. kefir* ketoreductase (SEQ ID NO:4); SEQ ID NO:144 is based on the wild-type amino acid sequence of the *L. brevis* ketoreductase (SEQ ID NO:2); and SEQ ID NO:143 is based on the wild-type amino acid sequence of the *L. minor* ketoreductase (SEQ ID NO:142). The ketoreductases based on the sequence formula of SEQ ID NO:143, 144 and 145 specify that residue corresponding to X145 is a polar amino acid.

In some embodiments, the ketoreductase polypeptides comprising an amino acid sequence based on sequence formulas of SEQ ID NO: 143, 144, or 145, or a domain thereof, such as residues 90-211, and having a polar residue, particularly serine, at the residue corresponding to X145, can further include one or more features selected from the following: residue corresponding to X3 is a polar, acidic, or aromatic residue; residue corresponding to X7 is a non-polar, polar, or constrained residue; residue corresponding to X11 is an aliphatic, non-polar, or polar residue; residue corresponding to X16 is an aliphatic or non-polar residue; residue corresponding to X19 is a non-polar or aliphatic residue; residue corresponding to X23 is a non-polar or aromatic residue; residue corresponding to X41 is an aliphatic, non-polar, or polar residue; residue corresponding to X45 is an aliphatic, non-polar, or polar residue; residue corresponding to X49 is a basic residue; residue corresponding to X57 is an aliphatic or non-polar residue; residue corresponding to X60 is an aromatic, aliphatic, non-polar, or polar residue; residue corresponding to X64 is an aliphatic or non-polar residue; residue corresponding to X72 is a basic residue; residue corresponding to X82 is a non-polar or polar residue; residue corresponding to X94 is a polar, basic, aliphatic, or non-polar residue; residue corresponding to X95 is a non-polar or aliphatic residue; residue corresponding to X96 is a constrained, aliphatic, non-polar, acidic, or polar residue; residue corresponding to X97 is acidic, basic, or aliphatic residue; residue corresponding to X106 is an acidic residue; residue corresponding to X108 is a basic, constrained, or aromatic residue; residue corresponding to X111 is an aliphatic or non-polar residue; residue corresponding to X117 is a non-polar or polar residue; residue corresponding to X126 is an aliphatic or non-polar residue; residue corresponding to X127 is a polar or basic residue; residue corresponding to X147 is an aromatic, aliphatic residue, non-polar, or polar residue; residue corresponding to X152 is a polar, aliphatic or non-polar residue; residue corresponding to X157 is a polar or acidic residue; residue corresponding to X163 is an aliphatic or non-polar residue; residue corresponding to X173 is an acidic or non-polar residue; residue corresponding to X177 is a basic residue; residue corresponding to X192 is a basic or acidic residue; residue corresponding to X194 is a constrained, polar, acidic, non-polar, or aliphatic residue; residue corresponding to X198 is an acidic or non-polar residue; residue corresponding to X200 is a constrained, acidic, or basic residue; residue corresponding to X206 is a polar or non-polar residue; residue corresponding to X208 is a polar, constrained, or basic residue; residue corresponding to X210 is an aliphatic, non-polar, or polar residue; residue corresponding to X211 is a basic or acidic residue; residue corresponding to X214 is a non-polar, aliphatic or polar residue; residue corresponding to X217 is an aromatic, aliphatic, or non-polar residue; residue corresponding to X223 is an aliphatic or non-polar residue; and residue corresponding to X226 is a non-polar or aliphatic residue. In some embodiments, residue corresponding to X94 is not an aromatic residue, histidine, or glycine. In some embodiments, the residue corresponding to X96 is not an aromatic residue, glycine, isoleucine or cysteine. In some embodiments, the polypeptides comprising an amino acid sequence that corresponds to the sequence formulas as laid out in SEQ ID NO:143, 144 or 145 (or domain thereof) can have one or more of the residues not specified by an X to be conservatively mutated. In some embodiments, the conservative mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 amino acid residues.

In some embodiments, the polypeptides comprising an amino acid sequence based on the sequence formulas provided in SEQ ID NO:143, 144, or 145 can have one or more conservative mutations as compared to the reference sequence of SEQ ID NO: 4, 2, or 142. Exemplary conservative substitutions include amino acid replacements such as, but not limited to: replacement of residue corresponding to X19 (I) with another aliphatic residue, e.g., valine; replacement of residue corresponding to X23 (I) with another non-polar residue, e.g., phenylalanine; replacement of residue corresponding to X49 (K) with another basic residue, e.g., arginine; replacement of residue corresponding to X57 (I) with another aliphatic residue, e.g., valine; replacement of residue corresponding to X72 (K) with another basic amino acid, e.g., arginine; replacement of residue corresponding to X94 (A) with another aliphatic amino acid, e.g., valine; replacement of residue corresponding to X95 (A) with another aliphatic residue, e.g., valine; replacement of residue corresponding to X97 (K) with another basic amino acid, e.g., arginine; replacement of residue corresponding to X106 (E) with another acidic amino acid, e.g., aspartic acid; replacement of residue corresponding to X111 (L) with another non-polar or aliphatic amino acid, e.g., methionine; replacement of residue X147 (F) with another non-polar amino acid, e.g., leucine; replacement of residue corresponding to X177 (K) with another basic amino acid, e.g., arginine; replacement of residue corresponding to X192 (K) with another basic amino acid, e.g., arginine; replacement of residue corresponding to X214 (M) with another non-polar amino acid, e.g., valine; replacement of residue corresponding to X217 (I) with another non-polar amino acid, e.g., phenylalanine; replacement of residue corresponding to X223 (I) with another non-polar or aliphatic amino acid, e.g., valine; and replacement of residue corresponding to X226 (I) with another non-polar or aliphatic amino acid, e.g., leucine.

In some embodiments, the ketoreductase polypeptides comprising an amino acid sequence based on sequence formulas of SEQ ID NO: 143, 144, or 145, or a domain thereof, such as residues 90-211 and having a polar residue, particularly serine, at the residue corresponding to X145, can further include one or more features selected from the following: residue corresponding to X3 is asparagine, aspartic acid, or tyrosine; residue corresponding to X7 is glycine, histidine, serine or asparagine; residue corresponding to X11 is isoleucine or threonine; residue corresponding to X16 is threonine, alanine, valine, or glycine; residue corresponding to X19 is isoleucine or valine; residue corresponding to X23 is a isoleucine or phenylalanine; residue corresponding to X41 is serine, alanine, or valine; residue corresponding to X45 is glutamic acid or glycine; residue corresponding to X49 is lysine or arginine, particularly arginine; residue corresponding to X57 is isoleucine or valine; residue corresponding to X60 is phenylalanine, valine, or threonine; residue corresponding to X64 is alanine, serine, or threonine; residue corresponding to X72 is lysine or arginine, particularly arginine; residue corresponding to X82 is glycine or serine; residue corresponding to X94 is alanine, valine, threonine, serine, or arginine; residue corresponding to X95 is valine or alanine; residue corresponding to X96 is asparagine, serine, proline, alanine, or glutamic acid; residue corresponding to X97 is lysine, arginine or leucine; residue corresponding to X106 is glutamic acid or aspartic acid; residue corresponding to X108 is arginine or histidine; residue corresponding to X111 is leucine or methionine; residue corresponding to X117 is glycine or serine; residue corresponding to X126 is isoleucine or valine; residue corresponding to X127 is glutamine or arginine; residue corresponding to X147 is phenylalanine, leucine or serine; residue corresponding to X152 is threonine, serine, or methionine; residue corresponding to X157 is asparagine, glutamine, threonine, serine, or aspartic acid; residue corresponding to X163 is valine or isoleucine; residue corresponding to X173 is aspartic acid or glycine; residue corresponding to X177 is lysine or arginine; residue corresponding to X192 is lysine, arginine or glutamic acid; residue corresponding to X194 is proline, glycine, aspartic acid, arginine, or leucine; residue corresponding to X198 is aspartic acid or glycine; residue corresponding to X200 is proline, glutamic acid, or lysine; residue corresponding to X206 is methionine or glutamine; residue corresponding to X208 is glutamine, histidine or arginine; residue corresponding to X210 is threonine or alanine; residue corresponding to X211 is lysine or glutamic acid; residue corresponding to X214 is methionine, valine or threonine, or serine, particularly valine or threonine; residue corresponding to X217 is isoleucine or phenylalanine; residue corresponding to X223 is isoleucine or valine; and residue corresponding to X226 is isoleucine or valine. In some embodiments, the polypeptides comprising an amino acid sequence that corresponds to the sequence formulas as laid out in SEQ ID NO:143, 144 or 145 (or domain thereof) can have one or more of the residues not specified by an X to be conservatively mutated. In some embodiments, the conservative mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 amino acid residues.

In some embodiments, the ketoreductase polypeptides comprising an amino acid sequence based on sequence formulas of SEQ ID NO: 143, 144, or 145, or a domain thereof, such as residues 90-211, and having a polar residue, particularly serine, at the residue corresponding to X145, can further include one or more or at least all of the following features: residue corresponding to X7 is a non-polar, polar, or constrained residue; residue corresponding to X94 is a polar, basic, aliphatic, or non-polar residue; residue corresponding to X96 is a constrained, aliphatic, non-polar, acidic, or polar residue; residue corresponding to X108 is a basic, constrained, or aromatic residue; residue corresponding to X117 is a non-polar or polar residue; residue corresponding to X157 is a polar or acidic residue; residue corresponding to X173 is an acidic or non-polar residue; residue corresponding to X206 is a polar or non-polar residue; and residue corresponding to X223 is an aliphatic or non-polar residue. In some embodiments, the amino acid residue corresponding to X145 is serine. In some embodiments, the ketoreductase polypeptides can include further include, in addition to the preceding features, one or more of features selected from the following: residue corresponding to X3 is a polar, acidic, or aromatic residue; residue corresponding to X11 is an aliphatic, non-polar, or polar residue; residue corresponding to X16 is an aliphatic or non-polar residue; residue corresponding to X19 is a non-polar or aliphatic residue; residue corresponding to X23 is a non-polar or aromatic residue; residue corresponding to X41 is an aliphatic, non-polar, or polar residue; residue corresponding to X45 is an glycine, aliphatic, non-polar, or polar residue; residue corresponding to X49 is a basic residue; residue corresponding to X57 is an aliphatic or non-polar residue; residue corresponding to X60 is an aromatic, aliphatic, non-polar, or polar residue; residue corresponding to X64 is an aliphatic or non-polar residue; residue corresponding to X72 is a basic residue; residue corresponding to X82 is a non-polar or polar residue; residue corresponding to X95 is a non-polar or aliphatic residue; residue corresponding to X97 is acidic, basic, or aliphatic residue; residue corresponding to X106 is an acidic residue; residue corresponding to X111 is an aliphatic or non-polar residue; residue corresponding to X126 is an aliphatic or non-polar residue; residue corresponding to X127 is a polar or basic residue; residue correspond to X147 is an aromatic, aliphatic residue, non-polar, or polar residue; residue corresponding to X152 is a polar, aliphatic or non-polar residue; residue corresponding to X163 is an aliphatic or non-polar residue; residue corresponding to X177 is a basic residue; residue corresponding to X192 is a basic or acidic residue; residue corresponding to X194 is a constrained, polar, non-polar, acidic, or aliphatic residue; residue corresponding to X198 is an acidic or non-polar residue; residue corresponding to X200 is a constrained, acidic, or basic residue; residue corresponding to X208 is a polar, constrained, or basic residue; residue corresponding to X210 is an aliphatic, non-polar, or polar residue; residue corresponding to X211 is a basic or acidic residue; residue corresponding to X214 is a non-polar, aliphatic or polar residue; residue corresponding to X217 is an aromatic, aliphatic, or non-polar residue; and residue corresponding to X226 is a non-polar or aliphatic residue. In some embodiments, the polypeptides comprising an amino acid sequence that corresponds to the sequence formulas as laid out in SEQ ID NO:143, 144 or 145 (or domain thereof) can have one or more of the residues not specified by an X to be conservatively mutated. In some embodiments, the conservative mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 amino acid residues.

In some embodiments, the ketoreductase polypeptides comprising an amino acid sequence based on sequence formulas of SEQ ID NO: 143, 144, or 145, or a domain thereof, such as residues 90-211, and having a polar residue, particularly serine, at the residue corresponding to X145, can further include one or more or at least all of the features selected from the following: residue corresponding to X7 is glycine, histidine, serine or asparagine; residue corresponding to X94 is alanine, valine, threonine, serine, or arginine; residue corresponding to X96 is asparagine, serine, proline, alanine, or glutamic acid; residue corresponding to X108 is arginine or histidine; residue corresponding to X117 is glycine or serine; residue corresponding to X157 is asparagine, glutamine, threonine, serine, or aspartic acid; residue corresponding to X173 is aspartic acid or glycine; residue corresponding to X206 is methionine or glutamine; and residue corresponding to X223 is isoleucine or valine. In some embodiments, the ketoreductase polypeptides can include further include, in addition to the preceding features, one or more of features selected from the following: residue corresponding to X3 is asparagine, aspartic acid, or tyrosine; residue corresponding to X11 is isoleucine or threonine; residue corresponding to X16 is threonine, alanine, valine, or glycine; residue corresponding to X19 is isoleucine or valine; residue corresponding to X23 is an isoleucine or phenylalanine; residue corresponding to X41 is serine, alanine, or valine; residue corresponding to X45 is glutamic acid or glycine; residue corresponding to X49 is lysine or arginine, particularly arginine; residue corresponding to X57 is isoleucine or valine; residue corresponding to X60 is phenylalanine, valine, or threonine; residue corresponding to X64 is alanine, serine, or threonine; residue corresponding to X72 is lysine or arginine, particularly arginine; residue corresponding to X82 is glycine or serine; residue corresponding to X95 is valine or alanine; residue corresponding to X97 is lysine, arginine or leucine; residue corresponding to X106 is glutamic acid or aspartic acid; residue corresponding to X111 is leucine or methionine; residue corresponding to X126 is isoleucine or valine; residue corresponding to X127 is glutamine or arginine; residue corresponding to X147 is phenylalanine, leucine or serine; residue corresponding to X152 is threonine, serine, or methionine; residue corresponding to X163 is valine or isoleucine; residue corresponding to X177 is lysine or arginine; residue corresponding to X192 is lysine, arginine or glutamic acid; residue corresponding to X194 is proline, glycine, aspartic acid, arginine, or leucine; residue corresponding to X198 is aspartic acid or glycine; residue corresponding to X200 is proline, glutamic acid, or lysine; residue corresponding to X208 is glutamine, histidine or arginine; residue corresponding to X210 is threonine or alanine; residue corresponding to X211 is lysine or glutamic acid; residue corresponding to X214 is methionine, valine or threonine, or serine, particularly valine or threonine; residue corresponding to X217 is isoleucine or phenylalanine; and residue corresponding to X226 is isoleucine or valine. In some embodiments, the polypeptides comprising an amino acid sequence that corresponds to the sequence formulas as laid out in SEQ ID NO:143, 144 or 145 (or domain thereof) can have one or more of the residues not specified by an X to be conservatively mutated. In some embodiments, the conservative mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine; and residue corresponding to X3 is a polar, acidic, or aromatic residue, particularly tyrosine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X7 is a non-polar, polar, or constrained residue, particularly serine, histidine, or arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X11 is an aliphatic, non-polar, or polar residue. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X16 is an aliphatic or non-polar residue, particularly alanine or glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X19 is a non-polar or aliphatic residue, particularly alanine or glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X23 is a non-polar or aromatic residue, particularly phenylalanine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X41 is an aliphatic, non-polar, or polar residue, particularly serine, alanine or valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X45 is an glycine, aliphatic, non-polar, or polar residue, particularly glutamic acid or glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X49 is a basic residue, particularly arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X57 is an aliphatic or non-polar residue, particularly isoleucine or valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X60 is an aromatic, aliphatic, non-polar, or polar residue, particularly phenylalanine, valine, or threonine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X64 is an aliphatic or non-polar residue, particularly alanine, serine, or threonine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X72 is a basic residue, particularly alanine, serine, or threonine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X82 is a non-polar or polar residue, particularly glycine or serine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X94 is a polar, basic, aliphatic, or non-polar residue, particularly valine, threonine, or arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X95 is a non-polar residue or aliphatic residue, particularly alanine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X96 is a constrained, aliphatic, non-polar, acidic, or polar residue, particularly asparagine, serine, proline, alanine, or glutamic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X97 is acidic, basic, or aliphatic residue, particularly lysine, arginine or leucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X106 is an acidic residue, particularly aspartic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X108 is a basic, constrained, or aromatic residue, particularly arginine or histidine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X111 is an aliphatic or non-polar residue, particularly methionine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X117 is a non-polar or polar residue, particularly serine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X126 is a an aliphatic or non-polar residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X127 is a polar or basic residue, particularly glutamine or arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue correspond to X147 is an aromatic, aliphatic residue, non-polar, or polar residue, particularly phenylalanine, leucine or serine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X152 is a polar, aliphatic or non-polar residue, non-polar, or polar residue, particularly threonine, serine, or methionine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X157 is a polar or basic residue, particularly asparagine, threonine, serine, or aspartic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X163 is a an aliphatic or non-polar residue, particularly valine or isoleucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X173 is an acidic or non-polar residue, particularly aspartic acid or glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X177 is a basic residue, particularly arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X192 is a basic or acidic residue, particularly lysine, arginine or glutamic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X194 is a constrained, polar, non-polar, acidic, or aliphatic residue, particularly proline, glycine, aspartic acid, arginine, or leucine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X198 is an acidic or non-polar residue, particularly aspartic acid or glycine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X200 is a constrained, acidic, or basic residue, particularly proline, glutamic acid, or lysine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X200 is a constrained, acidic, or basic residue, particularly proline, glutamic acid, or lysine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X206 is a polar or non-polar residue, particularly methionine or glutamine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X208 is a polar, constrained, or basic residue, particularly glutamine, histidine or arginine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X210 is an aliphatic, non-polar, or polar residue, particularly threonine or alanine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X211 is a basic or acidic residue, particularly lysine or glutamic acid. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X214 is a non-polar, aliphatic or polar residue, particularly valine or threonine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X217 is an aromatic, aliphatic, or non-polar residue, particularly isoleucine or phenylalanine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X223 is an aliphatic or non-polar residue, particularly isoleucine or valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X226 is a non-polar or aliphatic residue, particularly isoleucine or valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence based on the sequence formula of SEQ ID NO: 143, 144, or 145, or a domain thereof, such as residues 90-211, in which the amino acid sequence has at least the following features: residue corresponding to X145 is a polar residue, particularly serine, and residue corresponding to X228 is a non-polar or aliphatic residue, particularly valine or alanine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine or asparagine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X94 is a polar, basic, aliphatic, or nonpolar residue; particularly valine, threonine, or arginine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X96 is a constrained, aliphatic, non-polar, acidic, or polar residue, particularly asparagine, proline, alanine, or glutamic acid; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X108 is a basic, constrained, or aromatic residue, particularly histidine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X117 is a non-polar or polar residue, particularly serine; residue corresponding to X145 is a polar residue, particularly serine; residue corresponding to X173 is an acidic or non-polar residue, particularly glycine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X108 is a basic, constrained, or aromatic residue, particularly histidine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X108 is a basic, constrained, or aromatic residue, particularly histidine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 is a polar residue, particularly serine; and residue corresponding to X157 is a polar or acidic residue, particularly a threonine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X108 is a basic, constrained, or aromatic residue, particularly histidine; residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X108 is a basic, constrained, or aromatic residue, particularly histidine; residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X108 is a basic, constrained, or aromatic residue, particularly histidine; residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 is a polar residue, particularly serine; residue corresponding to X157 is a polar or acidic residue, particularly a threonine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X117 is a non-polar or polar residue, particularly serine; residue corresponding to X145 is a polar residue, particularly serine; residue corresponding to X157 is a polar or acidic residue, particularly a threonine; residue corresponding to X173 is an acidic or non-polar residue, particularly glycine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X117 is a non-polar or polar residue, particularly serine; residue corresponding to X145 is a polar residue, particularly serine; residue corresponding to X157 is a polar or acidic residue, particularly a threonine; residue corresponding to X173 is an acidic or non-polar residue, particularly glycine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X96 is a constrained, aliphatic, non-polar, acidic, or polar residue, particularly asparagine, proline, alanine, or glutamic acid; residue corresponding to X117 is a non-polar or polar residue, particularly serine; residue corresponding to X145 is a polar residue, particularly serine; residue corresponding to X157 is a polar or acidic residue, particularly a threonine; residue corresponding to X173 is an acidic or non-polar residue, particularly glycine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase polypeptide comprises an amino acid sequence based on the sequence formula of SEQ ID NO: 143, 144, or 145, or a domain thereof, such as residues 90-211, in which the amino acid sequence has at least the following features: residue corresponding to X7 is a non-polar, polar, or constrained residue, particularly serine, histidine, or asparagine; residue corresponding to X94 is a polar, basic, aliphatic, or non-polar residue; particularly valine, threonine, or arginine; residue corresponding to X96 is a constrained, aliphatic, non-polar, acidic, or polar residue, particularly asparagine, proline, alanine, or glutamic acid; residue corresponding to X117 is a non-polar or polar residue, particularly serine; residue corresponding to X145 is a polar residue, particularly serine; residue corresponding to X157 is a polar or acidic residue, particularly a threonine; residue corresponding to X173 is an acidic or non-polar residue, particularly glycine; and residue corresponding to X206 is a polar or non-polar residue, particularly glutamine. In some embodiments the ketoreductases can have additionally at residue corresponding to X223 an aliphatic residue, particularly valine. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO: 2, 4, or 142 having the preceding features. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to a reference sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, and 134, as listed in Table 2, wherein the improved ketoreductase polypeptide amino acid sequence includes any one set of the specified amino acid substitution combinations presented in Table 2. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, the improved ketoreductases comprise polypeptides with amino acid sequences corresponding to SEQ ID NOS: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, and 134.

In some embodiments, an improved ketoreductase comprises an amino acid sequence based on the sequence formula of SEQ ID NO: 143, 144, or 145, or a domain thereof, such as residues 90-211, having at least the following features: residue corresponding to X72 is a basic residue, particularly arginine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:104. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:104.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:44. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:44.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X49 is a basic residue, particularly arginine; residue corresponding to X111 is a non-polar residue, particularly methionine; residue corresponding to X117 is a polar residue, particularly serine; residue corresponding to X145 is a polar residue, particularly serine; residue corresponding to X157 is a polar residue, particularly threonine; residue corresponding to X173 is a non-polar residue, particularly glycine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:68. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:68.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X94 is a non-polar or polar residue, particularly threonine; residue corresponding to X97 is a non-polar or aliphatic residue, particularly leucine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X223 is an aliphatic residue, particularly valine; and residue corresponding to X226 is an aliphatic residue, particularly leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:42. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:42.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X94 is a non-polar or polar residue, particularly threonine; residue corresponding to X96 is a constrained or acidic residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:24. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:24.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X94 is a non-polar or polar residue, particularly threonine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:38. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:38.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly serine; residue corresponding to X94 is a non-polar or polar residue, particularly threonine; residue corresponding to X96 is a constrained or acidic residue, particularly glutamic acid; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:32. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:32.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X94 is a non-polar or polar residue, particularly threonine; residue corresponding to X106 is an acidic residue, particularly aspartic acid; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:8. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:8.

In some embodiments, an improved ketoreductase comprises an amino acid sequence based on the sequence formula of SEQ ID NO: 143, 144, or 145, or a domain thereof, such as residues 90-211, having at least the following features: residue corresponding to X3 is an aromatic residue, particularly tyrosine; residue corresponding to X7 is a polar residue, particularly arginine; residue corresponding to X94 is a non-polar or polar residue, particularly threonine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:134. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:134.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X94 is a non-polar or polar residue, particularly threonine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X208 is a constrained residue, particularly histidine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:6. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:6.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X94 is a non-polar or polar residue, particularly threonine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:26. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:26.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:52. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:52.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:50. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:50.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X16 is a non-polar or aliphatic residue, particularly glycine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:76. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:76.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X16 is a non-polar or aliphatic residue, particularly valine; residue corresponding to X94 is a non-polar or polar residue, particularly threonine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:80. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:80.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X16 is a non-polar or aliphatic residue, particularly glycine; residue corresponding to X94 is a non-polar or polar residue, particularly threonine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:78. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:78.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X94 is a non-polar or polar residue, particularly threonine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X194 is a non-polar residue, particularly glycine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:30. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:30.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X94 is a non-polar or polar residue, particularly threonine; residue corresponding to X96 is a constrained residue, particularly proline; residue corresponding to X108 is a constrained residue, particularly histidine; residue corresponding to X117 is a polar residue, particularly serine; residue corresponding to X145 is a polar residue, particularly serine; residue corresponding to X157 is a polar residue, particularly threonine; residue corresponding to X194 is a basic residue, particularly arginine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:22. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:22.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X49 is a basic residue, particularly arginine; residue corresponding to X111 is a non-polar or aliphatic residue, particularly methionine; residue corresponding to X117 is a polar residue, particularly serine; residue corresponding to X145 is a polar residue, particularly serine; residue corresponding to X157 is a polar residue, particularly threonine; residue corresponding to X173 is a non-polar residue, particularly glycine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:70. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:70.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X49 is a basic residue, particularly arginine; residue corresponding to X96 is a constrained residue, particularly proline; residue corresponding to X111 is a non-polar or aliphatic residue, particularly methionine; residue corresponding to X117 is a polar residue, particularly serine; residue corresponding to X145 is a polar residue, particularly serine; residue corresponding to X157 is a polar residue, particularly threonine; residue corresponding to X173 is a non-polar residue, particularly glycine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:66. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:66.

In some embodiments, an improved ketoreductase comprises an amino acid sequence based on the sequence formula of SEQ ID NO: 143, 144, or 145, or a domain thereof, such as residues 90-211, having at least the following features: residue corresponding to X7 is a polar residue, particularly arginine; residue corresponding to X49 is a basic residue, particularly arginine; residue corresponding to X94 is a polar residue, particularly threonine; residue corresponding to X96 is a constrained residue, particularly proline; residue corresponding to X111 is a non-polar or aliphatic residue, particularly methionine; residue corresponding to X117 is a polar residue, particularly serine; residue corresponding to X145 is a polar residue, particularly serine; residue corresponding to X157 is a polar residue, particularly threonine; residue corresponding to X173 is a non-polar residue, particularly glycine; residue corresponding to X206 is a polar residue, particularly glutamine; and residue corresponding to X223 is an aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:58. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:58.

In some embodiments, an improved ketoreductase comprises an amino acid sequence that has a region or domain corresponding to residues 90-211 of sequence formula of SEQ ID NO: 143, 144, or 145, in which the residue corresponding to X145 in the domain is a polar residue. In some embodiments, the region or domain that corresponds to residues 90-211 of sequence formula of SEQ ID NOS: 143, 144, or 145 has at the residue corresponding to X145 a serine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence of based on SEQ ID NO:2, 4 or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, the ketoreductase polypeptides with a domain corresponding to residues 90-211 and having a polar residue, particularly serine, at the residue corresponding to X145, can further include one or more features selected from the following: residue corresponding to X94 is a polar, basic, aliphatic, or non-polar residue; residue corresponding to X95 is a non-polar or aliphatic residue; residue corresponding to X96 is a constrained, aliphatic, non-polar, acidic, or polar residue; residue corresponding to X97 is acidic, basic, or aliphatic residue; residue corresponding to X106 is an acidic residue; residue corresponding to X108 is a basic, constrained, or aromatic residue; residue corresponding to X111 is an aliphatic or non-polar residue; residue corresponding to X117 is a non-polar or polar residue; residue corresponding to X126 is an aliphatic or non-polar residue; residue corresponding to X127 is a polar or basic residue; residue corresponding to X147 is an aromatic, aliphatic residue, non-polar, or polar residue; residue corresponding to X152 is a polar, aliphatic or non-polar residue; residue corresponding to X157 is a polar or acidic residue; residue corresponding to X163 is an aliphatic or non-polar residue; residue corresponding to X173 is an acidic or non-polar residue; residue corresponding to X177 is a basic residue; residue corresponding to X192 is a basic or acidic residue; residue corresponding to X194 is a constrained, polar, non-polar, acidic, or aliphatic residue; residue corresponding to X198 is an acidic or non-polar residue; residue corresponding to X200 is a constrained, acidic, or basic residue; residue corresponding to X206 is a polar or non-polar residue; residue corresponding to X208 is a polar, constrained, or basic residue; residue corresponding to X210 is an aliphatic, non-polar, or polar residue; and residue corresponding to X211 is a basic or acidic residue. In some embodiments, residue corresponding to X94 is not an aromatic residue, histidine, or glycine. In some embodiments, the residue corresponding to X96 is not an aromatic residue, glycine, isoleucine or cysteine. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides having a domain or region corresponding to residues 90-211 based on sequence formula of SEQ ID NO:143, 144, or 145 can have one or more conservative mutations as compared to the amino acid sequence of SEQ ID NO: 4, 2, or 142. Exemplary conservative substitutions include amino acid replacements such as, but not limited to: replacement of residue corresponding to X94 (A) with another aliphatic amino acid, e.g., valine; replacement of residue corresponding to X95 ((V) with another non-polar or aliphatic residue, e.g., alanine; replacement of residue corresponding to X97 (K) with another basic amino acid, e.g., arginine; replacement of residue corresponding to X106 (E) with another acidic amino acid, e.g., aspartic acid; replacement of residue corresponding to X111 (L) with another non-polar or aliphatic amino acid, e.g., methionine; replacement of residue X147 (F) with another non-polar amino acid, e.g., leucine; replacement of residue corresponding to X177 (K) with another basic amino acid, e.g., arginine; and replacement of residue corresponding to X192 (K) with another basic amino acid, e.g., arginine.

In some embodiments, the ketoreductase polypeptides with a domain corresponding to residues 90-211 and having a polar residue, particularly serine, at the residue corresponding to X145, can further include one or more features selected from the following: residue corresponding to X94 is alanine, valine, threonine, serine, or arginine; residue corresponding to X95 is valine or alanine; residue corresponding to X96 is asparagine, serine, proline, alanine, or glutamic acid; residue corresponding to X97 is lysine, arginine or leucine; residue corresponding to X106 is glutamic acid or aspartic acid; residue corresponding to X108 is arginine or histidine; residue corresponding to X111 is leucine or methionine; residue corresponding to X117 is glycine or serine; residue corresponding to X126 is isoleucine or valine; residue corresponding to X127 is glutamine or arginine; residue corresponding to X147 is phenylalanine, leucine or serine; residue corresponding to X152 is threonine, serine, or methionine; residue corresponding to X157 is asparagine, glutamine, threonine, serine, or aspartic acid; residue corresponding to X163 is valine or isoleucine; residue corresponding to X173 is aspartic acid or glycine; residue corresponding to X177 is lysine or arginine; residue corresponding to X192 is lysine, arginine or glutamic acid; residue corresponding to X194 is proline, glycine, aspartic acid, arginine, or leucine; residue corresponding to X198 is aspartic acid or glycine; residue corresponding to X200 is proline, glutamic acid, or lysine; residue corresponding to X206 is methionine or glutamine; residue corresponding to X208 is glutamine, histidine or arginine; residue corresponding to X210 is threonine or alanine; and residue corresponding to X211 is lysine or glutamic acid. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides with a domain corresponding to residues 90-211, and having a polar residue, particularly serine, at the residue corresponding to X145, can further include one or more or at least all of the features selected from the following: residue corresponding to X94 is a polar, basic, aliphatic, or non-polar residue; residue corresponding to X96 is a constrained, aliphatic, non-polar, acidic, or polar residue; residue corresponding to X108 is a basic, constrained, or aromatic residue; residue corresponding to X117 is a non-polar or polar residue; residue corresponding to X157 is a polar or acidic residue; residue corresponding to X173 is an acidic or non-polar residue; and residue corresponding to X206 is a polar or non-polar residue. In some embodiments, the domain or region can include further include, in addition to the preceding features, one or more of the features selected from the following: residue corresponding to X97 is acidic, basic, or aliphatic residue; residue corresponding to X106 is an acidic residue; residue corresponding to X111 is an aliphatic or non-polar residue; residue corresponding to X126 is an aliphatic or non-polar residue; residue corresponding to X127 is a polar or basic residue; residue correspond to X147 is an aromatic, aliphatic residue, non-polar, or polar residue; residue corresponding to X152 is a polar, aliphatic or non-polar residue; residue corresponding to X163 is an aliphatic or non-polar residue; residue corresponding to X177 is a basic residue; residue corresponding to X192 is a basic or acidic residue; residue corresponding to X194 is a constrained, polar, non-polar, acidic, or aliphatic residue; residue corresponding to X198 is an acidic or non-polar residue; residue corresponding to X200 is a constrained, acidic, or basic residue; residue corresponding to X208 is a polar, constrained, or basic residue; residue corresponding to X210 is an aliphatic, non-polar, or polar residue; and residue corresponding to X211 is a basic or acidic residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides with a domain corresponding to residues 90-211 and having a polar residue, particularly serine, at the residue corresponding to X145, can further include one or more or at least all of the features selected from the following: residue corresponding to X94 is alanine, valine, threonine, serine, or arginine; residue corresponding to X96 is asparagine, serine, proline, alanine, or glutamic acid; residue corresponding to X108 is arginine or histidine; residue corresponding to X117 is glycine or serine; residue corresponding to X157 is asparagine, glutamine, threonine, serine, or aspartic acid; residue corresponding to X173 is aspartic acid or glycine; and residue corresponding to X206 is methionine or glutamine. In some embodiments, the domain or region can include further include, in addition to the preceding features, one or more of the features selected from the following: residue corresponding to X95 is valine or alanine; residue corresponding to X97 is lysine, arginine or leucine; residue corresponding to X106 is glutamic acid or aspartic acid;

residue corresponding to X111 is leucine or methionine; residue corresponding to X126 is isoleucine or valine; residue corresponding to X127 is glutamine or arginine; residue corresponding to X147 is phenylalanine, leucine or serine; residue corresponding to X152 is threonine, serine, or methionine; residue corresponding to X163 is valine or isoleucine; residue corresponding to X173 is aspartic acid or glycine; residue corresponding to X177 is lysine or arginine; residue corresponding to X192 is lysine, arginine or glutamic acid; residue corresponding to X194 is proline, glycine, aspartic acid, arginine, or leucine; residue corresponding to X198 is aspartic acid or glycine; residue corresponding to X200 is proline, glutamic acid, or lysine; residue corresponding to X208 is glutamine, histidine or arginine; residue corresponding to X210 is threonine or alanine; and residue corresponding to X211 is lysine or glutamic acid. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X117 is a non-polar or polar residue, particularly serine; residue corresponding to X145 a polar residue, particularly a serine; and residue corresponding to X157 is a polar or acidic residue, particularly serine or threonine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a polar, basic, aliphatic, or non-polar residue, particularly threonine or valine; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 mutations at other amino acid residues in the domain. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a non-polar or polar residue, particularly threonine or valine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a non-polar or polar residue, particularly threonine or valine; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a non-polar or polar residue, particularly threonine or valine; residue corresponding to X96 is a constrained, aliphatic, non-polar, acidic, or polar residue, particularly asparagine, proline, alanine, or glutamic acid; residue corresponding to X108 is a basic, constrained, or aromatic residue, particularly histidine; residue corresponding to X117 is a non-polar or polar residue, particularly serine; residue corresponding to X145 a polar residue, particularly a serine; and residue corresponding to X157 is a polar or acidic residue, particularly serine or threonine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X117 is a non-polar or polar residue, particularly serine; residue corresponding to X145 a polar residue, particularly a serine; and residue corresponding to X157 is a polar or acidic residue, particularly serine or threonine; residue corresponding to X173 is an acidic or non-polar residue, particularly glycine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a non-polar or polar residue, particularly threonine or valine; residue corresponding to X117 is a non-polar or polar residue, particularly serine; residue corresponding to X145 a polar residue, particularly a serine; and residue corresponding to X157 is a polar or acidic residue, particularly serine or threonine; residue corresponding to X173 is an acidic or non-polar residue, particularly glycine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X96 is a constrained, aliphatic, non-polar, acidic, or polar residue, particularly asparagine, proline, alanine, or glutamic acid; residue corresponding to X117 is a non-polar or polar residue, particularly serine; residue corresponding to X145 a polar residue, particularly a serine; and residue corresponding to X157 is a polar or acidic residue, particularly serine or threonine; residue corresponding to X173 is an acidic or non-polar residue, particularly glycine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 90-211 based on the sequence formula of SEQ ID NO: 143, 144, or 145, having at least the following features: residue corresponding to X94 is a non-polar or polar residue, particularly threonine or valine;

residue corresponding to X96 is a constrained, aliphatic, non-polar, acidic, or polar residue, particularly asparagine, proline, alanine, or glutamic acid; residue corresponding to X117 is a non-polar or polar residue, particularly serine; residue corresponding to X145 a polar residue, particularly a serine; and residue corresponding to X157 is a polar or acidic residue, particularly serine or threonine; residue corresponding to X173 is an acidic or non-polar residue, particularly glycine; and residue corresponding to X206 is a polar or non-polar residue, particularly glutamine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4, or 142. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 142 with the preceding features.

In some embodiments, an improved ketoreductase comprises an amino acid sequence that has a region or domain corresponding to residues 1-89 of sequence formula of SEQ ID NO: 143, 144, or 145. In some embodiments, the residue corresponding to X7 in the domain is a polar or constrained residue, particularly serine, histidine, or asparagine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 142. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 142 with the preceding feature at residue X7.

In some embodiments, the region or domain corresponding to residues 1-89 can have one or more of the features selected from the following: residue corresponding to X3 is a polar, acidic, or aromatic residue, particularly tyrosine or aspartic acid; residue corresponding to X7 is a non-polar, polar, or constrained residue, particularly serine, histidine, or asparagine; residue corresponding to X11 is an aliphatic, non-polar, or polar residue, particularly isoleucine or threonine; residue corresponding to X16 is an aliphatic or non-polar residue, particularly threonine, alanine, valine, or glycine; residue corresponding to X19 is a non-polar or aliphatic residue, particularly isoleucine or valine; residue corresponding to X23 is a nonpolar or aromatic residue, particularly phenylalanine; residue corresponding to X41 is an aliphatic, non-polar, or polar residue, particularly serine, alanine, or valine; residue corresponding to X45 is an aliphatic, non-polar, or polar residue, particularly glutamic acid or glycine; residue corresponding to X49 is a basic residue, particularly lysine or arginine; residue corresponding to X57 is an aliphatic or non-polar residue, particularly isoleucine or valine; residue corresponding to X60 is an aromatic, aliphatic, non-polar, or polar residue, particularly phenylalanine, valine, or threonine; residue corresponding to X64 is an aliphatic or non-polar residue, particularly alanine, serine, or threonine; residue corresponding to X72 is a basic residue, particularly lysine or arginine; and residue corresponding to X82 is a non-polar or polar residue, particularly glycine or serine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 142. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 142 with the preceding feature at residue X7.

In some embodiments, an improved ketoreductase comprises an amino acid sequence that has a region or domain corresponding to residues 212-252 of sequence formula of SEQ ID NO: 143, 144, or 145. In some embodiments, the residue corresponding to X223 in the domain is an aliphatic residue, particularly valine. In some embodiments, the region or domain corresponding to residues 212-252 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues in the domain as compared to a reference sequence of SEQ ID NO:2, 4 or 142. In some embodiments, the number of difference can be 1, 2, 3, 4, 5, 6, 7, 8, 9, 10, 11, 12, 14, 15, 16, 18, or about 20 residue differences in the domain. In some embodiments, the differences comprise conservative mutations as compared to the reference sequence. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 212-252 of a reference sequence based on SEQ ID NO:2, 4 or 142 with the preceding feature at residue X223.

In some embodiments, the region or domain corresponding to residues 212-252 can have one or more or at least all of the features selected from the following: residue corresponding to X214 is a non-polar, aliphatic or polar residue, particularly methionine, valine, threonine, or serine; residue corresponding to X217 is an aromatic, aliphatic, or non-polar residue, particularly isoleucine or phenylalanine; residue corresponding to X223 is an aliphatic or non-polar residue, particularly isoleucine or valine; and residue corresponding to X226 is a non-polar or aliphatic residue, particularly isoleucine or valine. In some embodiments, the region or domain corresponding to residues 212-252 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain based on reference sequence of SEQ ID NO:2, 4 or 142. In some embodiments, the number of difference can be 1, 2, 3, 4, 5, 6, 7, 8, 9, 10, 11, 12, 14, 15, 16, 18, or about 20 residue differences at other residues in the domain. In some embodiments, the differences comprise conservative mutations. In some embodiments, the ketoreductase polypeptide comprises an amino acid sequence that has at least 85%, 86%, 87%, 88%, 89%, 90%, 91%, 92%, 93%, 94%, 95%, 96%, 97%, 98%, or 99% identity as compared to the amino acid sequence corresponding to residues 212-252 of a reference sequence based on SEQ ID NO:2, 4 or 142 with the preceding feature at residue X223.

In some embodiments, the ketoreductase polypeptides of the present disclosure can comprise an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO:2, SEQ ID NO:4, or SEQ ID NO:142, or a region or domain thereof, such as residues 90-211, with the proviso that the residue corresponding to residue 145 is a polar residue. In some embodiments, the residue corresponding to residue 145 can be a polar residue and the polypeptide is capable of reducing the substrate to the product with at least about 70% s.e. In some embodiments, the residue corresponding to residue 145 is serine, and additionally has one or more of the following substitutions such that the polypeptide is further improved (with respect to stereoselectivity, enzymatic activity, and/or thermostability) over the wild-type kefir ketoreductase or another engineered ketoreductase: 3→Y (i.e., the residue corresponding to residue 3 of SEQ ID NO:2, 4, or 142, is substituted to tyrosine); 7→S,N; 11→T; 16→A,V,G; 19→V; 23→F; 41→V; 45→G; 49→R; 57→V; 60→T; 64→T; 72→R; 82→S; 94→T,R; 95→A; 96→P,A,E; 97→R; 106→D; 108→H; 111→M; 117→S; 126→V; 127→R; 147→L,S; 152→M; 157→T,S,D; 163→I; 173→G; 177→R; 192→R,E; 194→G,D,N,L; 198→G; 200→K; 206→Q; 208→H,R; 210→A; 211→E; 214→V,T; 217→F; 223→V; 226→L; and 228→A.

In some embodiments, the residue corresponding to residue 145 is serine, and additionally has one or more of the following substitutions such that the polypeptide is further improved over the wild-type kefir ketoreductase or another engineered ketoreductase: 7→S,N; 94→T,V; 96→P; 108→H; 117→S; 157→T; 194→N; 206→Q; and 223→V.

In some embodiments, the residue corresponding to residue 145 is serine, and additionally has one or more of the following substitutions such that the polypeptide is further improved over the wild-type kefir ketoreductase or another engineered ketoreductase: 7→S,N; 94→T,V; 96→P; 108→H; 117→S; 157→T; 173→G; 194→N; 206→Q; and 223→V.

In some embodiments, each of the improved engineered ketoreductase enzymes described herein can comprise deletions of the polypeptides described herein. Thus, for each and every embodiment of the ketoreductase polypeptides of the disclosure, the deletions can be one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acids. In some embodiments, the deletions can comprise deletions of 1-2, 1-3, 1-4, 1-5, 1-6, 1-7, 1-8, 1-9, 1-10, or 1-20 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As will be appreciated by those of skill in the art, some of the above-defined categories of amino acid residues, unless otherwise specified, are not mutually exclusive. Thus, amino acids having side chains exhibiting two or more physicochemical properties can be included in multiple categories. The appropriate classification of any amino acid or residue will be apparent to those of skill in the art, especially in light of the detailed disclosure provided herein.

As described herein, the ketoreductase polypeptides of the disclosure can be in the form of fusion polypeptides in which the ketoreductases polypeptides are fused to other polypeptides, such as antibody tags (e.g., myc epitope) or purifications sequences (e.g., His tags). Thus, the ketoreductase polypeptides can be used with or without fusions to other polypeptides.

In some embodiments, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Pat); 4-iodophenylalanine (Pit); 4-aminomethylphenylalanine (Pamf); 2,4-dichlorophenylalanine (Opcf); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); δ-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

7.3 Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 3 has been codon optimized for expression in *E. coli*, but otherwise encodes the naturally occurring ketoreductase of *L. kefir*.

In some embodiments, the polynucleotide comprises a nucleotide sequence encoding a ketoreductase polypeptide with an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, where the encoded ketoreductase polypeptide comprises an amino acid sequence that has at the residue corresponding to residue position 145 of SEQ ID NO:2, 4 or 142 a polar residue, particularly a serine. In some embodiments, the polynucleotides encode an engineered ketoreductase polypeptide comprising an amino acid sequence selected from SEQ ID NOS: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, or 134.

In some embodiments, the polynucleotides encoding the engineered ketoreductases are selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and 133.

In some embodiments, the polynucleotides are capable of hybridizing under highly stringent conditions to one of the polynucleotides comprising a sequence corresponding to SEQ ID NO:5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and 133, where the polynucleotide that hybridizes under highly stringent conditions encode a functional ketoreductase capable of converting the substrate of structural formula (I) to the product of structural formula (II).

In some embodiments, the polynucleotides comprise a nucleic acid sequence that encodes the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding an engineered ketoreductase, where the polynucleotide encodes a functional ketoreductase capable of converting the substrate of structural formula (I) to the product of structural formula (II). In some embodiments, the reference polynucleotide is selected from the sequences corresponding to SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and 133.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual*, 3rd Ed., Cold Spring Harbor Laboratory Press; and *Current Protocols in Molecular Biology*, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus maltogenic amylase* gene (amyM), *Bacillus amyloliquefaciens* alpha-amylase gene (amyQ), *Bacillus licheniformis* penicillinase gene (penP), *Bacillus subtilis* xylA and xylB genes, and prokaryotic β-lactamase gene (Villa-Kamaroff et al., 1978, *Proc. Natl Acad. Sci. USA* 75: 3727-3731), as well as the tac promoter (DeBoer et al., 1983, *Proc. Natl Acad. Sci. USA* 80: 21-25). Further promoters are described in "Useful proteins from recombinant bacteria" in *Scientific American*, 1980, 242:74-94; and in Sambrook et al., supra.

For filamentous fungal host cells, suitable promoters for directing the transcription of the nucleic acid constructs of the present disclosure include promoters obtained from the genes for Aspergillus oryzae TAKA amylase, Rhizomucor miehei aspartic proteinase, Aspergillus niger neutral alpha-amylase, Aspergillus niger acid stable alpha-amylase, Aspergillus niger or Aspergillus awamori glucoamylase (glaA), Rhizomucor miehei lipase, Aspergillus oryzae alkaline protease, Aspergillus oryzae triose phosphate isomerase, Aspergillus nidulans acetamidase, and Fusarium oxysporum trypsin-like protease (WO 96/00787), as well as the NA2-tpi promoter (a hybrid of the promoters from the genes for Aspergillus niger neutral alpha-amylase and Aspergillus oryzae triose phosphate isomerase), and mutant, truncated, and hybrid promoters thereof.

In a yeast host, useful promoters can be from the genes for Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH2/GAP), and Saccharomyces cerevisiae 3-phosphoglycerate kinase. Other useful promoters for yeast host cells are described by Romanos et al., 1992, *Yeast* 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for Aspergillus oryzae TAKA amylase, Aspergillus niger glucoamylase, Aspergillus nidulans anthranilate synthase, Aspergillus niger alpha-glucosidase, and Fusarium oxysporum trypsin-like protease.

Exemplary terminators for yeast host cells can be obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for Aspergillus oryzae TAKA amylase and Aspergillus nidulans triose phosphate isomerase. Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for Aspergillus oryzae TAKA amylase, Aspergillus niger glucoamylase, Aspergillus nidulans anthranilate synthase, Fusarium oxysporum trypsin-like protease, and Aspergillus niger alpha-glucosidase. Useful polyadenylation sequences for yeast host cells are described by Guo and Sherman, 1995, *Mol Cell Bio.* 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137.

Effective signal peptide coding regions for filamentous fungal host cells can be the signal peptide coding regions obtained from the genes for Aspergillus oryzae TAKA amylase, Aspergillus niger neutral amylase, Aspergillus niger glucoamylase, Rhizomucor miehei aspartic proteinase, Humicola insolens cellulase, and Humicola lanuginosa lipase.

Useful signal peptides for yeast host cells can be from the genes for Saccharomyces cerevisiae alpha-factor and Saccharomyces cerevisiae invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for Bacillus subtilis alkaline protease (aprE), Bacillus subtilis neutral protease (nprT), Saccharomyces cerevisiae alpha-factor, Rhizomucor miehei aspartic proteinase, and Myceliophthora thermophila lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, Aspergillus niger glucoamylase promoter, and Aspergillus oryzae glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in some embodiments, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

In some embodiments, the expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vectors of the present disclosure can contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from Bacillus subtilis or Bacillus licheniformis, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an Aspergillus cell include the amdS and pyrG genes of Aspergillus nidulans or Aspergillus oryzae and the bar gene of Streptomyces hygroscopicus.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proc Natl Acad Sci. USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAG™ expression vectors from Sigma-Aldrich Chemicals, St. Louis MO, which includes a CMV promoter and hGH polyadenylation site for expression in mammalian host cells and a pBR322 origin of replication and ampicillin resistance markers for amplification in *E. coli*. Other suitable expression vectors are pBluescriptII SK(-) and pBK-CMV, which are commercially available from Stratagene, LaJolla CA, and plasmids which are derived from pBR322 (Gibco BRL), pUC (Gibco BRL), pREP4, pCEP4 (Invitrogen) or pPoly (Lathe et al., 1987, *Gene* 57:193-201).

7.4 Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Streptomyces* and *Salmonella typhimurium* cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include, among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved ketoreductase into the plasmid pCK110900 operatively linked to the lac promoter under control of the lacI repressor. The expression vector also contains the P15a origin of replication and the chloramphenicol resistance gene. Cells containing the subject polynucleotide in *Escherichia coli* W3110 were isolated by subjecting the cells to chloramphenicol selection.

7.5 Methods of Generating Engineered Ketoreductase Polypeptides

In some embodiments, to make the improved KRED polynucleotides and polypeptides of the present disclosure, the naturally-occurring ketoreductase enzyme that catalyzes the reduction reaction is obtained (or derived) from *Lactobacillus kefir* or *Lactobacillus brevis*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity. The sequence designated (SEQ ID NO: 1) was the parent sequence utilized as the starting point for most experiments and library construction of engineered ketoreductases evolved from the *Lactobacillus kefir* ketoreductase.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. (For example, see Example 7.) In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, TX, The Great American Gene Company, Ramona, CA, ExpressGen Inc. Chicago, IL, Operon Technologies Inc., Alameda, CA, and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis MO.

Chromatographic techniques for isolation of the ketoreductase polypeptide include, among others, reverse phase chromatography, high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and Corynebacterium parvum.

7.6 Methods of Using the Engineered Ketoreductase Enzymes and Compounds Prepared Therewith The ketoreductase enzymes described herein are capable of catalyzing the reduction reaction of the keto group in the compound of structural formula (I), 3-ketothiolane:

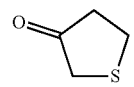

(I)

to the corresponding chiral alcohol product of structural formula (II), (R)-3-hydroxythiolane:

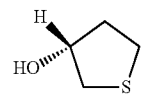

(II)

In some embodiments, the invention provides a method for reducing a substrate of structural compound of formula (I) to the product of the structural formula (II), where the method comprises contacting or incubating the substrate with a ketoreductase polypeptide disclosed herein under reaction conditions suitable for reducing the substrate to the alcohol product.

For example, in some embodiments of the method, the ketoreductase polypeptides comprise an amino acid sequence having, as compared to the wild-type *L. kefir* or *L. brevis* or *L. minor* KRED sequences of SEQ ID NO: 4, 2 and 142, respectively, a polar residue, particularly a serine, at the residue corresponding to X145. As noted herein, the ketoreductase polypeptide can have in addition, one or more mutations at other amino acid residues as compared to the references sequences of SEQ ID NO:2, 4, or 106. Such differences are described in the sequence formulas of SEQ ID NO:143, 144, and 145 and the descriptions herein.

In some embodiments of this method, the ketoreductase polypeptide comprises, by way of example and not limitation, an amino acid sequence that is at least 85%, 86%, 87%, 88%, 89%, 90%, 91%, 92%, 93%, 94%, 95%, 96%, 97%, 98%, 99% or more identical to a reference sequence based on SEQ ID NO: 2, 4, or 142 having a polar residue, particularly serine, at the residue corresponding to X145, where the ketoreductase polypeptide also has a polar residue, particularly serine, at the residue corresponding to X145.

In some embodiments of the method, the product is reduced in greater than about 65% stereomeric excess, where the ketoreductase polypeptide comprises a sequence corresponding to SEQ ID NOS: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, or 134.

In some embodiments of the method, the substrate is reduced to the product in greater than about 90% stereomeric excess, wherein the ketoreductase polypeptide comprises an amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 86, 88, 90, 92, 94, 96, 100, 102, 104, 106, 108, 110, 112, 126, 128, 130, or 134.

In some embodiments of the method, the substrate is reduced to the product in greater than about 98% s.e., wherein the ketoreductase polypeptide comprises an amino acid sequences corresponding to corresponding to SEQ ID NO: 6, 8, 10, 18, 20, 22, 24, 26, 28, 30, 34, 36, 38, 40, 42, 50, 52, 54, 58, 62, 66, 70, 72, 76, 78, 80, and 134.

In some embodiments of the method for reducing the substrate to the product, the substrate is reduced to the product at an improved rate as compared to the wild-type enzyme (SEQ ID NO:4), wherein the ketoreductase polypeptide comprises an amino acid sequence corresponding to SEQ ID NO: 6, 8, 10, 12, 14, 16, 18, 20, 22, 24, 26, 30, 32, 38, 40, 42, 44, 46, 48, 50, 52, 54, 56, 58, 60, 64, 66, 68, 70, 74, 76, 78, 80, 86, 88, 90, 92, 104, 106, 110, 112, 124, 126, 130, or 134.

In some embodiments, the reaction condition is pH 7.5 or less. In some embodiments, the reaction condition is at a pH of from about 5.0 to about 7.5. In some embodiments, the reaction condition is at a pH of from about pH 6.0 to 7.5. In some embodiments, the reaction condition temperature is about 25° C. or less. In some embodiments, the reaction condition is at a temperature of 5° C. to about 25° C. or 5° C. to 15° C. In some embodiments, the reaction condition also includes a cofactor regenerating system, as further described below.

In some embodiments, a method for reducing the substrate to the product can comprise contacting the substrate with a ketoreductase of the disclosure in a reaction condition comprising at least 100 g/L of substrate and at least 0.8-1.0 g/L of the ketoreductase polypeptide, wherein at least 90% of the substrate is converted to product in less than 24 hrs (e.g., 20-24 hrs). In some embodiments, greater than 95%, 96%, 97%, 98%, or 99% or more of the substrate is converted to the product under the reaction condition. Exemplary polypeptides for use in the method, include, but are not limited to, polypeptides comprising the amino acid sequences corresponding to SEQ ID NO: 6, 8, 10, 12, 14, 18, 20, 22, 24, 26, 30, 32, 38, 40, 42, 44, 46, 48, 50, 52, 54, 56, 58, 60, 64, 66, 68, 70, 74, 76, 78, 80, 82, 86, 88, 90, 92, 104, 106, 110, 112, 126, 130, and 134.

In some embodiments, a method for reducing the substrate to the product can comprise contacting the substrate with a ketoreductase of the disclosure in a reaction condition comprising at least 100 g/L of substrate and at least 0.8-1.0 g/L of the ketoreductase polypeptide, wherein at least 90% of the substrate is converted to product in 12-20 hrs. In some embodiments, greater than 95%, 96%, 97%, 98%, or 99% or more of the substrate is converted to the product under the reaction condition. Exemplary polypeptides for use in the method, include, but are not limited to, SEQ ID NO: 26, 44, 68, and 104.

In some embodiments, any one of the ketoreductases polypeptide provided herein can be used in the production of (R)-3-hydroxythiolane, which is an intermediate for producing various drugs, such as antibiotics and protease inhibitors. In some embodiments, the ketoreductase polypeptides can be used in the production of the antibiotic sulopenem (CP-70,429), having the following structural formula (III), and salts thereof, and solvates and hydrates thereof:

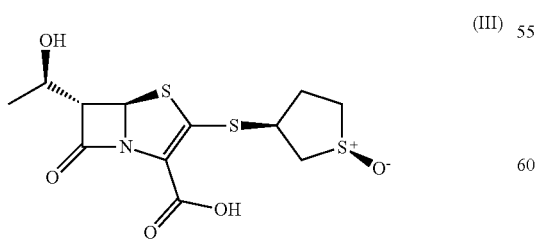

(III)

Thus, in some embodiments, in a method for the synthesis of the antibiotic of structural formula (III) (i.e., CP-70,429), a step in the method can comprise contacting the substrate of formula (I) with any of the ketoreductases described herein, thereby converting or reducing the substrate to the product of structural formula (II).

The product of structural formula (II) can be converted to sulopenem, having structural formula (III), and intermediates thereto, by the synthetic route described in *J. Org. Chem.*, 1992, 57:4352, incorporated by reference herein. The route described therein is depicted below, wherein Ts is p-tosyl, Ac is acetyl, and TBS is t-butyldimethylsilyl.

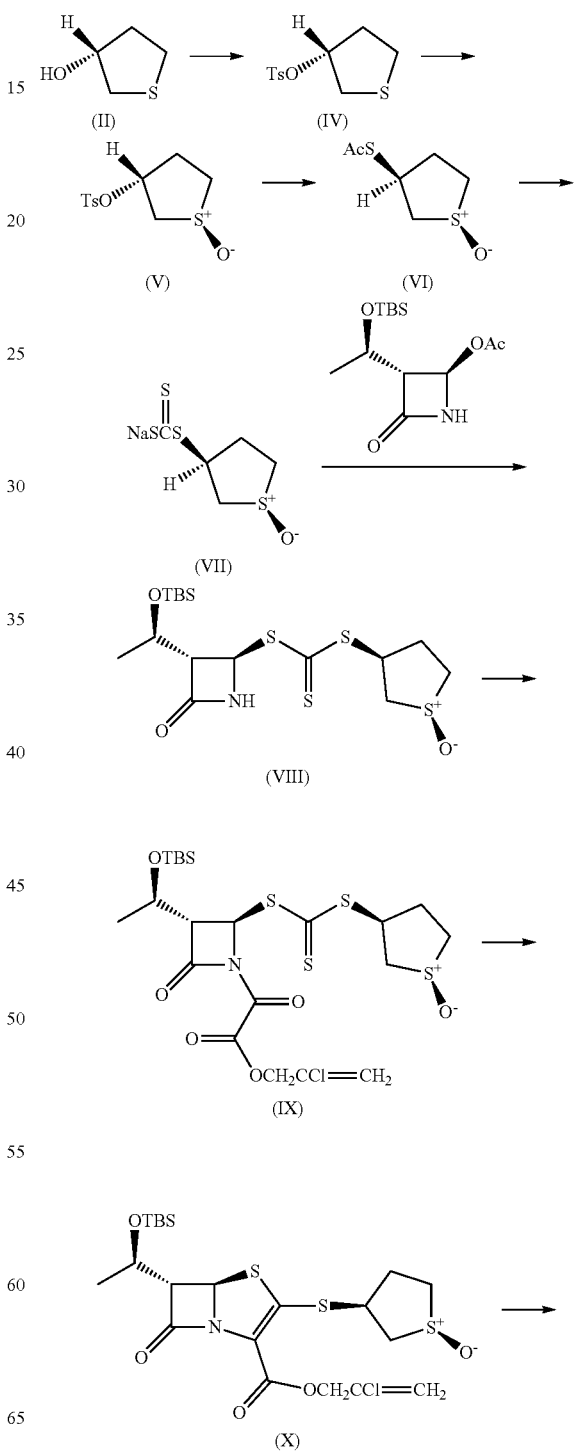

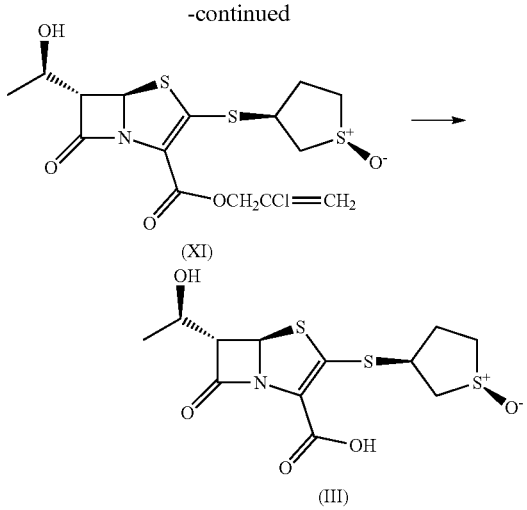

(XI)

(III)

In some embodiments, methods provide for the syntheses of each one of the intermediates of structural formulae (IV), (V), (VI), (VII), (VIII), (IX), (X), and (XI), where a step in the method for synthesis of the intermediates can comprise contacting the substrate of formula (I) with any of the ketoreductases described herein under suitable conditions for converting or reducing the substrate to the product of structural formula (II).

The additional step or steps in such methods may be according to the procedures for the step or steps described in J. Org. Chem., 1992, 57:4352, incorporated by reference, or modifications thereof. For the conversion of the product of structural formula (II) to the intermediate of structural formula (IV), the dimethylaminopyridine reagent used in the procedure described in J. Org. Chem., 1992, 57:4352 may be substituted with pyridine or 1-methylimidazole. For the conversion of the intermediate of structural formula (IV) to the intermediate of structural formula (V), the reaction that is conducted at 0° C. in the procedure described in J. Org. Chem., 1992, 57:4352 may be conducted at lower temperatures, e.g., at −25° C., to further minimize the formation of the corresponding sulfone by-product.

In some embodiments, the (R)-3-hydroxythiolane intermediate can be used in the synthesis of HIV-protease inhibitors (*J. Med. Chem.*, 1994, 37:1177) or other compounds or drugs whose synthesis relies on the intermediate (R)-3-hydroxythiolane (formula (II)), wherein a step in the method for synthesis of the drug compound comprises reducing or converting the compound of formula (I) to the compound of formula (II) using any one of the ketoreductase polypeptides provided herein.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, NADP$^+$ (nicotinamide adenine dinucleotide phosphate), NADPH (the reduced form of NADP$^+$), NAD$^+$ (nicotinamide adenine dinucleotide) and NADH (the reduced form of NAD$^+$). Generally, the reduced form of the cofactor is added to the reaction mixture. The reduced NAD(P)H form can be optionally regenerated from the oxidized NAD(P)$^+$ form using a cofactor regeneration system.

The term "cofactor regeneration system" refers to a set of reactants that participate in a reaction that reduces the oxidized form of the cofactor (e.g., NADP$^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD$^+$ or NADP$^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NAD$^+$/NADPH or NAD$^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an NAD$^+$ or NADP$^+$-dependent enzyme that catalyzes the conversion of D-glucose and NAD$^+$ or NADP$^+$ to gluconic acid and NADH or NADPH, respectively. Equation (1), below, describes the glucose dehydrogenase-catalyzed reduction of NAD$^+$ or NADP$^+$ by glucose.

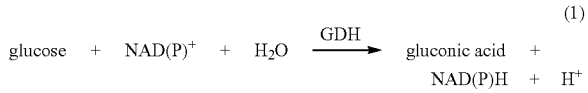

(1)

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (*Nature*, 2003, 423:87-91; Genbank Acc. No. AE017013)

and *B. megaterium* (*Eur. J. Biochem.*, 1988, 174:485-490, Genbank Acc. No. X12370; J. Ferment. Bioeng., 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incoporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octacnol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (1) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an $NAD^+$ or $NADP^+$-dependent enzyme that catalyzes the conversion of formate and $NAD^+$ or $NADP^+$ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 µmol/min/mg, sometimes at least about 10 µmol/min/mg, or at least about $10^2$ µmol/min/mg, up to about $10^3$ µmol/min/mg or higher, and can be readily screened for activity in the assay described in Example 4 of PCT publication WO 2005/018579.

As used herein, the term "formate" refers to formate anion ($HCO_2^-$), formic acid ($HCO_2H$), and mixtures thereof. Formate may be provided in the form of a salt, typically an alkali or ammonium salt (for example, $HCO_2Na$, $KHCO_2NH_4$, and the like), in the form of formic acid, typically aqueous formic acid, or mixtures thereof. Formic acid is a moderate acid. In aqueous solutions within several pH units of its pKa (pKa=3.7 in water) formate is present as both $HCO_2$ and $HCO_2H$ in equilibrium concentrations. At pH values above about pH 4, formate is predominantly present as $HCO_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like.

For pH values above about pH 5, at which formate is predominantly present as $HCO_2^-$, Equation (2) below, describes the formate dehydrogenase-catalyzed reduction of $NAD^+$ or $NADP^+$ by formate.

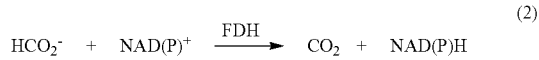

(2)

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., $KH_2PO_4$), bisulfate salts (e.g., $NaHSO_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an $NAD^+$ or $NADP^+$-dependent enzyme that catalyzes the conversion of a secondary alcohol and $NAD^+$ or $NADP^+$ to a ketone and NADH or NADPH, respectively. Equation (3), below, describes the reduction of $NAD^+$ or $NADP^+$ by a secondary alcohol, illustrated by isopropanol.

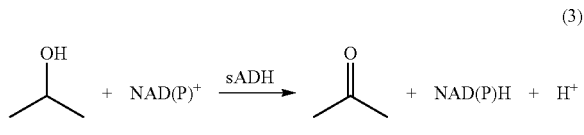

(3)

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occuring secondary alcohol dehydrogenases include known alcohol dehydrogenases from, Thermoanerobium brockii, Rhodococcus etythropolis, Lactobacillus kefiri, and Lactobacillus brevis, and non-naturally occurring secondary alcohol dehydrogenases include engineered alcohol dehdyrogenases derived therefrom. Secondary alcohol dehydrogenases employed in the methods described herein, whether naturally occurring or non-naturally occurring, may exhibit an activity of at least about 1 µmol/min/mg, sometimes at least about 10 µmol/min/mg, or at least about $10^2$ µmol/min/mg, up to about $10^3$ µmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-akyl carbinols include unsubstituted and substituted 1-arylethanols.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than about 90%, and are often greater than about 97%.

8. EXAMPLES

Various features and embodiments of the disclosure are illustrated in the following representative examples, which are intended to be illustrative, and not limiting.

8.1 Example 1: Wild-type Ketoreductase Gene Acquisition and Construction of Expression Vectors Ketoreductase (KRED) encoding genes were designed for expression in *E. coli* based on the reported amino acid sequence of the ketoreductase and a codon optimization algorithm as described in Example 1 of U.S. provisional application Ser. No. 60/848,950 and WO2008042876, incorporated herein by reference. Genes were synthesized using oligonucleotides composed of 42 nucleotides and cloned into expression vector pCK110900 (depicted as FIG. 3 in United States Patent Application Publication 20060195947) under the control of a lac promoter. The expression vector also contained the P15a origin of replication and the chloramphenicol resistance gene. Resulting plasmids were transformed into *E. coli* W3110 using standard methods. Sequences of codon optimized genes and the encoded polypeptides as well are listed in Table 3. The activity of the wild-type ketoreductases was confirmed as described in U.S. provisional application Ser. No. 60/848,950.

TABLE 3

Abbreviations, source and references for Ketoreductases used

| KRED | Microorganism from which enzyme was originally identified | Genbank Acc. No. | GI no. | Polynucleotide SEQ ID No | Polypeptide SEQ ID No, Or Source |
|---|---|---|---|---|---|
| ADH-CM | Candida magnoliae | AB036927.1 | 12657576 | SEQ ID No 1 in US Patent Appln Publn 20060195947 | SEQ ID No 2 in US Patent Appln Publn 20060195947 |
| YDL | Saccharomyces cerevisiae | NP_010159.1 | 6320079 | SEQ ID NO: 146 | SEQ ID NO: 147 |
| ADH-LB | Lactobacillus brevis | 1NXQ_A | 30749782 | SEQ ID NO: 1 (codon optimized) | SEQ ID NO: 2 |
| ADH-RE | Rhodococcus erythropolis | AAN73270.1 | 34776951 | SEQ ID NO: 148 | SEQ ID NO: 149 |
| YGL | Saccharomyces cerevisiae | NP_011476 | 6321399 | SEQ ID NO: 150 | SEQ ID NO: 151 |
| YPR | Saccharomyces cerevisiae | NP_010656.1 | 6320576 | SEQ ID NO: 152 | SEQ ID NO: 153 |
| GRE | Saccharomyces cerevisiae | NP_014490.1 | 6324421 | SEQ ID NO: 154 | SEQ ID NO: 155 |
| ADH-LK | Lactobacillus kefir | AAP94029.1 | 33112056 | SEQ ID NO: 3 (codon optimized) | SEQ ID NO: 4 |
| ADH-SB | Sporobolomyces salmonicolor | Q9UUN9 | 30315955 | SEQ ID NO: 137 | SEQ ID NO: 138 |
| ADH-SC | Streptomyces coelicolor | NP_631415.1 | 21225636 | SEQ ID NO: 135 | SEQ ID NO: 136 |
| ADH-TB | Thermoanaerobium brockii | X64841.1 | 1771790 | SEQ ID NO: 139 | SEQ ID NO: 140 |
| ADH-CP | Candida parapsilosis | BAA24528 | 2815409 | | Julich Chiral Solutions No. 03.11 |
| DR-LB | Lactobacillus brevis (diacetyl reductase) | ABJ63353.1 | 116098204 | | Julich Chiral Solutions No. 8.1 |

Polynucleotides encoding engineered ketoreductases of the present invention were likewise cloned into vector pCK110900 for expression in *E. coli* W3110.

8.2 Example 2: Production of Ketoreductase Powders; Shake Flask Procedure

A single microbial colony of *E. coli* containing a plasmid with the ketoreductase gene of interest was inoculated into 50 ml Luria Bertani broth containing 30 μg/ml chloramphenicol and 1% glucose. Cells were grown overnight (at least 16 hrs) in an incubator at 30° C. with shaking at 250 rpm. The culture was diluted into 250 ml Terrific Broth (12 g/L bacto-tryptone, 24 g/L yeast extract, 4 ml/L glycerol, 65 mM potassium phosphate, pH 7.0, 1 mM MgSO$_4$, 30 μg/ml chloramphenicol) in 1 liter flask) to an optical density at 600 nm (OD600) of 0.2 and allowed to grow at 30° C. Expression of the ketoreductase gene was induced with 1 mM IPTG when the OD600 of the culture is 0.6 to 0.8 and incubated overnight (at least 16 hrs). Cells were harvested by centrifugation (5000 rpm, 15 min, 4° C.) and the supernatant discarded. The cell pellet was resuspended with an equal volume of cold (4° C.) 100 mM triethanolamine (chloride) buffer, pH 7.0 (including 2 mM MgSO$_4$ in the case of ADH-LK and ADH-LB and engineered ketoreductases derived therefrom), and harvested by centrifugation as above. The washed cells were resuspended in two volumes of the cold triethanolamine (chloride) buffer and passed through a French Press twice at 12000 psi while maintained at 4° C. Cell debris was removed by centrifugation (9000 rpm, 45 min., 4° C.). The clear lysate supernatant was collected and stored at −20° C. Lyophilization of frozen clear lysate provided a dry powder of crude ketoreductase enzyme.

The activity of the wild-type ketoreductases was confirmed as described U.S. provisional application Ser. No. 60/848,950. To a solution of 1 mL 100 mM (sodium) phosphate buffer, pH 7.5, were added 10 mg ketoreductase powder, 50 mg NAD(P)H, 100 μL isopropanol and 10 mg 4'-chloroacetophenone or unsubstituted acetophenone. The reaction mixture was stirred at room temperature for 16 hours, then extracted with 1 mL MTBE. A sample of the MTBE phase was analyzed by chiral HPLC for the conversion of the 4'-chloro-acetophenone and the enantiomeric composition of the product.

8.3 Example 3: Production of Ketoreductases—Fermentation Procedure

In an aerated agitated 15 L fermenter, 6.0 L of growth medium containing 0.88 g/L ammonium sulfate, 0.98 g/L of sodium citrate, 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate was brought to a temperature of 30° C. The fermenter was inoculated with a late exponential culture of *E. coli* W3110, containing a plasmid with the ketoreductase gene of interest, grown in a shake flask as described in Example 2 to a starting OD600 of 0.5 to 2.0. The fermenter was agitated at 500-1500 rpm and air was supplied to the fermentation vessel at 1.0-15.0 L/min to maintain dissolved oxygen level of 30% saturation or greater. The pH of the culture was controlled at 7.0 by addition of 20% v/v ammonium hydroxide. Growth of the culture was maintained by the addition of a feed solution containing 500 g/L cerelose, 12 g/L ammonium chloride and 10.4 g/L magnesium sulfate heptahydrate. After the culture reached an OD600 of 50, the expression of ketoreductase was induced by the addition of isopropyl-β-D-thiogalactoside (IPTG) to a final concentration of 1 mM. The culture was grown for another 14 hours. The culture was then chilled to 4° C. and maintained at 4° C. until harvested. Cells were harvested by centrifugation at 5000 G for 40 minutes in a Sorval RC12BP centrifuge at 4° C. Harvested cells were used directly in the following downstream recovery process or were stored at 4° C. until such use.

The cell pellet was resuspended in 2 volumes of 100 mM triethanolamine (chloride) buffer, pH 6.8, at 4° C. to each volume of wet cell paste. The intracellular ketoreductase was released from the cells by passing the suspension through a homogenizer fitted with a two-stage homogenizing valve assembly using a pressure of 12000 psig. The cell homogenate was cooled to 4° C. immediately after disruption. A solution of 10% w/v polyethyleneimine, pH 7.2, was added to the lysate to a final concentration of 0.5% w/v and stirred for 30 minutes. The resulting suspension was clarified by centrifugation at 5000 G in a standard laboratory centrifuge for 30 minutes. The clear supernatant was decanted and concentrated ten fold using a cellulose ultrafiltration membrane with a molecular weight cut off of 30 Kd. The final concentrate was dispensed into shallow containers, frozen at −20° C. and lyophilized to powder. The ketoreductase powder was stored at −80° C.

8.4 Example 4: Analytical Methods to Determine Conversion of 3-Ketothiolane and Enantiomeric Excess of R-3-Hydroxythiolane Achiral GC to determine conversion: Reduction of 3-ketothiolane to 3-hydroxythiolane was determined using an Agilent HP-5MS Gas chromatograph equipped with a 5% phenyl methyl siloxane column (Model 19091S-433: 30 m×250 μm, nominal thickness 0.25 μm) with a helium flow rate of 1.0 mL/min. The inlet temperature was 220° C. and the following temperature program was used: 120° C. for 1 min then 20° C./min to 160° C. then 160° C. for 0.5 min. Compounds were detected spectrophotometrically at 210 nm. The retention times of the ketone and alcohol were 2.8 minutes, and 3.0 minutes respectively.

Chiral HPLC to determine stereomeric purity of 3-hydroxythiolane: The abundance of the R and S enantiomers of 3-hydroxythiolane was determined using an Agilent 1100 or 1050 HPLC equipped with a Chiralpak AD column (4.6× 250 mm and no guard column) with IPA/hexane (2/98) as eluent at a flow rate of 2.5 mL/min at room temperature. The retention times of the ketone, S-alcohol and R-alcohol were 8.6, 12.0 and 13.1 minute respectively Alternatively, an HPLC equipped with a Chiralpak AD-H column (4.6×150 mm and 10 mm guard column) was used with IPA/hexane (2/98) at a flow rate of 2.0 mL/min at 40° C. Compounds were detected spectrophotometrically at 210 nm. The retention times of the ketone, S-alcohol and R-alcohol were 6.3, 8.7 and 9.4 minute respectively.

8.5 Example 5: Evaluation of Wild-Type Ketoreductases for Reduction of 3-Ketothiolane The ketoreductases described in Table 3 (Example 1) were screened for enantioselective reduction of 3-ketothiolane under co-factor limiting conditions: to a vial under air was added 1-20 mg of enzyme, 1 mL of a co-factor stock solution containing 766 mg of NAD(P)H dissolved in 20 mL of 100 mM pH 8.0 triethanolamine(chloride) buffer and 20 μL 3-ketothiolane. After stirring at room temperature overnight, the reaction mixture was extracted with ethyl acetate and the enantioselectivity was assayed as described in Example 4. Results are described in Table 4. (NR=no reaction.)

TABLE 4

Activities of wild-type KREDs on 3-ketothiolane

| Source | Co-Factor Used | | e.e. | Configuration | |
|---|---|---|---|---|---|
| | NADH | NADPH | (%) | R | S |
| GRE | | X | 48 | | X |
| YPR | | X | 42 | | X |
| YGL | | X | 11 | X | |
| ADH-LB | | X | 46 | X | |
| ADH-LK | | X | 67 | X | |
| ADH-SB | | X | 66 | | X |
| ADH-SC | | X | NR | | |
| YDL | | X | ~0 | | |
| YDL | X | | ~0 | | |
| ADH-RE | X | | ~70 | | X |
| ADH-RE | | X | ~70 | | X |
| ADH-CP | | X | NR | | |
| ADH-CP | X | | ~80 | | X |
| ADH-TB | | X | 57 | | X |
| DR-LB | | X | 10 | X | |
| DR-LB | X | | 12 | X | |

This example shows that ADH-LK is the most R-enantioselective ketoreductase among the wild-type enzymes tested, giving R-3-hydroxythiolane in 67% e.e. Accordingly, ADH-LK was chosen as starting point for enzyme engineering towards the desired characteristics.

8.6 Example 6: High Throughput NADPH Fluorescence Prescreen To Identify Improved Enzymes for the Reduction of 3-Ketothiolane Plasmid libraries containing evolved ketoreductase genes were transformed into *E. coli* W3110 and plated on Luria-Bertani (LB) agar plates containing 1% glucose and 30 μg/mL chloramphenicol (CAM). After incubation for at least 16 hrs at 30° C., colonies were picked using a Q-bot® robotic colony picker (Genetix USA, Inc., Beaverton, OR) into shallow, 96-well well microtiter plates containing 180 μL LB, 1% glucose and 30 μg/mL CAM. Cells were grown overnight at 37° C. with shaking at 250 rpm. 10 μL of this culture was then transferred into 96-well microtiter plates (deep well) containing 390 μL Terrific broth (TB) and 30 μg/mL CAM. After incubation of deep-well plates at 30° C. with shaking at 250 rpm for 2.5 to 3 hours ($OD_{600}$ 0.6-0.8), recombinant gene expression by the cell cultures was induced by isopropyl thiogalactoside (IPTG) to a final concentration of 1 mM. The plates were then incubated at 30° C. with shaking at 250 rpm for overnight.

Cells were pelleted via centrifugation, resuspended in 300 μL lysis buffer and lysed by shaking at room temperature for at least 2 hours. The lysis buffer contained 100 mM triethanolamine (chloride) buffer, pH 7.0-7.2, 1 mg/mL lysozyme and 750 μg/mL polymixin B sulfate. The plates were centrifuged at 4000 RPM for 10 minutes and the clear supernatant (lysate) used in the fluorescent assay.

In 96-well black microtiter plates 20 μl of clear supernatant (diluted in 100 mM triethanolamine/chloride buffer, pH 7.0, 1 mM MgSO$_4$ if necessary) was added to 180 μl of an assay mixture consisting of 100 mM triethanolamine(chloride) buffer, pH 7.0, 1 mM MgSO$_4$, 0.25 mM NADPH, 600 mM glucose, 1200 mM sodium gluconate and 1 mM 3-ketothiolane and reaction progress measured by following the decrease in fluorescence of NADPH at 445 nm after excitation at 330 nm in a Flexstation (Molecular Devices, USA). To assess thermostability of KRED variants, clear supernatants were optionally pre-incubated for at least 16 hrs at a temperature ranging from 40 to 50° C., and then added into the assay mixture.

This example describes the method that was used to identify KRED variants improved for the rate of 3-ketothiolane reduction and/or improved for thermostability.

8.7 Example 7: High Throughput HPLC Assay for Ketoreductase Activity and Enantioselectivity for the Reduction of 3-Ketothiolane Using Glucose/Glucose Dehydrogenase for Co-Factor Recycling Lysates were prepared as described in Example 6. Ketoreductase activity was measured by transferring measured quantities of the cell lysates into the wells of deep well microtiter plates. The assay mixture in the wells (final volume 500 μl each well) contained 1 mg/mL GDH, 0.4 mg/ml Na-NADP, 0.2 to 1.25 M glucose 0 to 400 mM sodium gluconate, 100 mM triethanolamine(chloride) buffer (pH 7), 20 mM MgSO$_4$ and up to 50 mg calcium carbonate. Reactions were initiated by addition of up to 100 μl cell lysate and 50 μl 3-ketothiolane (final concentration 1M). After sealing with aluminum/polypropylene laminate heat seal tape (Velocity 11 (Menlo Park, CA), Cat #06643-001), the plates were incubated at 4 to 25° C. for up to 16 hrs. 1 ml ethyl acetate was injected into each well of the plates and the plates were shaken for 10 minutes, then centrifuged for 20 seconds; 100 μl of the ethyl acetate phase was transferred to shallow well microtiter plates. These sample plates were sealed with heat seal tape to prevent evaporation. The samples were analyzed by HPLC by the method of Example 4.

This example shows how ketoreductase variants with improved activity for the reduction of 3-ketothiolane and/or improved enantioselectivity for the formation of R-3-hydroxythiolane were identified in ketoreductase gene libraries.

8.8 Example 8: Reduction of 3-Ketothiolane by Engineered Ketoreductases Derived from ADH-LK Improved ketoreductases derived from ADH-LK variants were evaluated at preparative scale as follows. To a 25 mL three-neck vessel equipped with a PTFE-coated magnetic stirring bar and a pH electrode connected to an automatic titrator for pH-controlled addition of base on-demand via a feeding tube into the vessel, was charged with 18 ml aqueous (water or buffer) phase containing 6.63 g glucose. Subsequently, 3.0 g 3-ketothiolane (re-distilled), 30 to 120 mg KRED variant in 1 mL of the aqueous phase, 30 mg GDH in 1 mL of the aqueous phase, and 12 mg NADP-Na$_2$ were added. The automatic titrator maintained the pH at 7 by the addition of 4N NaOH, which was continuously recorded. Reaction progress was monitored by the rate and cumulative addition of the base and periodic sampling of the reaction mixture for extraction with ethyl acetate and analysis by the method of Example 4. The concentration of R-3-hydroxythiolane at reaction completion was 100±5 g/L.

Table 5 gives the SEQ ID NOs. corresponding to ketoreductase variants, the number of amino acid mutations from the wild-type ADH-LK, their activities for reduction of 3-ketothiolane (as amounts of enzyme powder required to completely convert the 3-ketothiolane to 3-hydroxythiolane in a 24 hr reaction), and their R-enantioselectivities for the 3-hydroxythiolane product (as e.e. ranges).

This Example illustrates that engineered ketoreductases derived from the ketoreductase ADH-LK that provide improved enantioselectivities and activities compared to the wild-type ketoreductase ADH-LK.

TABLE 5

Improved activities and stabilities of engineered ADH-LK variants

| SEQ ID NO. | mutations from ADH-LK | Enantioselectivity[a] | Activity[b] | Stability[c] |
|---|---|---|---|---|
| 4 | none | 0 | 0 | 0 |
| 120 | 1 | 0 | 0 | 0 |
| 166 | 1 | 0 | 0 | 0 |
| 122 | 2 | 0 | 0 | 0 |
| 114 | 2 | + | 0 | 0 |
| 118 | 3 | + | 0 | 0 |
| 132 | 6 | + | 0 | 0 |
| 84 | 3 | + | 0 | 0 |
| 98 | 1 | ++ | 0 | 0 |
| 124 | 6 | 0 | ++ | + |
| 102 | 2 | +++ | 0 | 0 |
| 90 | 2 | +++ | + | + |
| 16 | 3 | +++ | + | 0 |
| 100 | 2 | +++ | 0 | 0 |
| 108 | 2 | +++ | 0 | 0 |
| 128 | 3 | +++ | 0 | 0 |
| 96 | 2 | +++ | 0 | 0 |
| 130 | 2 | +++ | + | 0 |
| 126 | 2 | +++ | + | 0 |
| 104 | 5 | +++ | ++ | + |
| 88 | 3 | +++ | + | + |
| 106 | 6 | +++ | + | + |
| 14 | 5 | +++ | + | + |
| 86 | 6 | +++ | + | + |
| 44 | 6 | +++ | ++ | + |
| 92 | 4 | +++ | + | + |
| 112 | 8 | +++ | + | + |
| 94 | 4 | +++ | 0 | − |
| 12 | 4 | +++ | + | + |
| 56 | 8 | +++ | + | + |
| 110 | 6 | +++ | + | + |
| 36 | 7 | ++++ | 0 | + |
| 46 | 7 | +++ | + | + |
| 68 | 8 | +++ | ++ | + |
| 48 | 8 | +++ | + | − |
| 74 | 7 | +++ | + | + |
| 82 | 6 | +++ | + | + |
| 42 | 9 | ++++ | + | + |
| 24 | 8 | ++++ | + | + |
| 34 | 8 | ++++ | 0 | + |
| 38 | 8 | ++++ | + | + |
| 32 | 8 | +++ | + | + |
| 8 | 8 | ++++ | + | + |
| 134 | 8 | ++++ | + | + |
| 6 | 8 | ++++ | + | + |
| 26 | 9 | +++++ | ++ | + |
| 72 | 10 | +++++ | 0 | − |
| 18 | 10 | ++++ | + | 0 |
| 20 | 9 | ++++ | + | 0 |
| 54 | 9 | ++++ | + | 0 |
| 10 | 10 | ++++ | + | 0 |

TABLE 5-continued

Improved activities and stabilities of engineered ADH-LK variants

| SEQ ID NO. | mutations from ADH-LK | Enantioselectivity[a] | Activity[b] | Stability[c] |
|---|---|---|---|---|
| 40 | 9 | ++++ | + | 0 |
| 52 | 7 | ++++ | + | + |
| 50 | 8 | ++++ | + | + |
| 76 | 9 | ++++ | + | + |
| 80 | 10 | +++++ | + | + |
| 78 | 10 | ++++ | + | + |
| 30 | 10 | +++++ | + | + |
| 28 | 10 | +++++ | 0 | 0 |
| 22 | 10 | +++++ | + | + |
| 60 | 9 | +++ | + | + |
| 64 | 9 | +++ | + | + |
| 70 | 9 | ++++ | + | + |
| 62 | 10 | ++++ | 0 | 0 |
| 66 | 10 | ++++ | + | + |
| 58 | 11 | +++++ | + | + |

[a]Enantioselectivity column:
0 61.0-79.99% ee for the (R) enantiomer
+ 80.0-89.99% ee for the (R) enantiomer
++ 90.0-94.99% ee for the (R) enantiomer
+++ 95.0-97.99% ee for the (R) enantiomer
++++ 98.0-98.99% ee for the (R) enantiomer
+++++ >99.0% ee for the (R) enantiomer
[b]Activity column:
0 A concentration of 1.0-4.0 g/L of this enzyme is required to give full conversion of 100 g/L 3-ketothiolane within 24 h
+ A concentration of 0.8-1.0 g/L of this enzyme gives full conversion of 100 g/L 3-ketothiolane in 20 to 24 h
++ A concentration of 0.8-1.0 g/L of this enzyme gives full conversion of 100 g/L 3-ketothiolane in 12 to 20 h
[c]Stability column:
− less stable than ADH-LK
0 similarly stable as ADH-LK
+ more stable than ADH-LK

8.9 Example 9: Preparative Scale Production of R-(3)-Hydroxythiolane

To a 2-L three-neck jacketed flask under air at room temperature and fitted with mechanical stirrer at ~300 rpm, a thermometer, a pH electrode connected to an automatic titrator for pH-controlled addition of base on-demand via a feeding tube into the vessel, was added 600 mL 100 mM pH 7.0 triethanolamine(chloride) buffer, 2 mL 1 M $MgSO_4$, and 225 g D-glucose. After dissolution of the glucose (~½h), 100 g 3-ketothiolane was added to the reaction to give a biphasic mixture. The reaction temperature was lowered to 15° C. and 1.0 g ketoreductase powder (SEQ-ID No. 22) in 30 mL 100 mM pH 7.0 triethanolamine(chloride) buffer and 0.25 g GDH in 20 mL 100 mM pH 7.0 triethanolamine (chloride) buffer, and 0.4 g of $NADP-Na_2$ in 10 mL 100 mM pH 7.0 triethanolamine(chloride) buffer was added. The reaction temperature was maintained at 15° C. via an external circulating chiller and the automatic titrator maintained the pH at 7.0+0.1 by the addition of 8N NaOH. After stirring at 15° C. for 15 h the circulator temperature was raised to 25° C. and after 1 additional hour, 0.25 g GDH powder was added (final GDH concentration=0.5 g/L). After a total of 23 hours, 10 g $Na_2S_2O_5$ was added. After stirring for one additional hour at 25° C., the product was extracted with 750 mL ethyl acetate. The separated organic phase was filtered through ~20 g Celilte 545. The wet Celite pad was rinsed with 750 mL EtOAc. The combined organic phases were washed with 100 mL water. The separated organic phase was rotatory evaporated under vacuum at 60° C. for give 83.6 g (82% yield) of 3-hydroxythiolane as a pale yellow oil. Chiral HPLC analysis showed the (R)-3-hydroxythiolane in 99.3% enantiomeric excess.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered ketoreductase polypeptide comprising an amino acid sequence that is at least 90% identical to the reference sequence SEQ ID NO:4, and wherein said amino acid sequence comprises a substitution at position 41.

2. The engineered ketoreductase polypeptide of claim 1, in which the ketoreductase polypeptide amino acid sequence further comprises one or more additional substitutions selected from:
the residue corresponding to X3 is asparagine, aspartic acid, or tyrosine;
the residue corresponding to X7 is glycine, histidine, serine or asparagine;
the residue corresponding to X11 is isoleucine or threonine;
the residue corresponding to X16 is threonine, alanine, valine, or glycine;
the residue corresponding to X19 is isoleucine or valine;
the residue corresponding to X23 is isoleucine or phenylalanine;
the residue corresponding to X45 is glutamic acid or glycine;
the residue corresponding to X49 is lysine or arginine;
the residue corresponding to X57 is isoleucine or valine;
the residue corresponding to X60 is phenylalanine, valine, or threonine;
the residue corresponding to X64 is alanine, serine, or threonine;
the residue corresponding to X72 is lysine or arginine, particularly arginine;
the residue corresponding to X82 is glycine or serine;
the residue corresponding to X94 is alanine, valine, threonine, serine, or arginine;
the residue corresponding to X95 is valine or alanine;
the residue corresponding to X96 is asparagine, serine, proline, alanine, or glutamic acid;
the residue corresponding to X97 is lysine, arginine or leucine;
the residue corresponding to X106 is glutamic acid or aspartic acid;

the residue corresponding to X108 is arginine or histidine;
the residue corresponding to X111 is leucine or methionine;
the residue corresponding to X117 is glycine or serine;
the residue corresponding to X126 is isoleucine or valine;
the residue corresponding to X127 is glutamine or arginine;
the residue corresponding to X145 is aspartic acid or serine;
the residue corresponding to X147 is phenylalanine, leucine or serine;
the residue corresponding to X152 is threonine, serine, or methionine;
the residue corresponding to X163 is valine or isoleucine;
the residue corresponding to X173 is aspartic acid or glycine;
the residue corresponding to X177 is lysine or arginine;
the residue corresponding to X192 is lysine, arginine or glutamic acid;
the residue corresponding to X194 is proline, glycine, aspartic acid, arginine, or leucine;
the residue corresponding to X198 is aspartic acid or glycine;
the residue corresponding to X200 is proline, glutamic acid, or lysine;
the residue corresponding to X206 is methionine or glutamine;
the residue corresponding to X208 is glutamine, histidine or arginine;
the residue corresponding to X210 is threonine or alanine;
the residue corresponding to X211 is lysine or glutamic acid;
the residue corresponding to X214 is methionine, valine or threonine, or serine;
the residue corresponding to X217 is isoleucine or phenylalanine;
the residue corresponding to X223 is isoleucine or valine; and
the residue corresponding to X226 is isoleucine or valine.

3. The engineered ketoreductase polypeptide of claim 1, wherein the ketoreductase polypeptide amino acid sequence further comprises at least one additional substitution selected from:
the residue corresponding to X7 is a non-polar, polar, or constrained residue;
the residue corresponding to X94 is a polar, basic, aliphatic, or non-polar residue;
the residue corresponding to X96 is a constrained, aliphatic, non-polar, acidic, or polar residue;
the residue corresponding to X108 is a basic, constrained, or aromatic residue;
the residue corresponding to X117 is a non-polar or polar residue;
the residue corresponding to X147 is a non-polar or aliphatic residue;
the residue corresponding to X173 is an acidic or non-polar residue;
the residue corresponding to X206 is a polar or non-polar residue; and
the residue corresponding to X223 is an aliphatic or non-polar residue.

4. The engineered ketoreductase polypeptide of claim 1, in which the ketoreductase polypeptide amino acid sequence further comprises the following substitutions:
the residue corresponding to X117 is a non-polar or polar residue;
the residue corresponding to X147 is a non-polar or aliphatic residue.

5. The engineered ketoreductase polypeptide of claim 1, in which the ketoreductase polypeptide amino acid sequence further comprises at least one substitution selected from:
the residue corresponding to X7 is a non-polar, polar, or constrained residue;
the residue corresponding to X94 is a polar, basic, aliphatic, or non-polar residue;
the residue corresponding to X108 is a basic, constrained, or aromatic residue;
the residue corresponding to X117 is a non-polar or polar residue, particularly serine;
the residue corresponding to X147 is a non-polar or aliphatic residue.

6. The engineered ketoreductase polypeptide of claim 1 in which the ketoreductase polypeptide amino acid sequence comprises the following substitutions:
the residue corresponding to X7 is a non-polar, polar, or constrained residue;
the residue corresponding to X96 is a constrained, aliphatic, non-polar, acidic, or polar residue;
the residue corresponding to X108 is a basic, constrained, or aromatic residue;
the residue corresponding to X117 is a non-polar or polar residue, particularly serine; and
the residue corresponding to X147 is leucine.

7. The engineered ketoreductase polypeptide of claim 1, in which the ketoreductase polypeptide amino acid sequence further comprises the following substitutions:
the residue corresponding to X7 is a non-polar, polar, or constrained residue;
the residue corresponding to X94 is a polar, basic, aliphatic, or non-polar residue;
the residue corresponding to X96 is a constrained, aliphatic, non-polar, acidic, or polar residue;
residue corresponding to X108 is a basic, constrained, or constrained residue;
the residue corresponding to X117 is a non-polar or polar residue, particularly serine.

8. The engineered ketoreductase polypeptide of claim 1, in which the ketoreductase polypeptide amino acid sequence further comprises the following substitutions:
the residue corresponding to X7 is a non-polar, polar, or constrained residue;
the residue corresponding to X108 is a basic, constrained, or aromatic residue;
the residue corresponding to X117 is a non-polar or polar residue; and
the residue corresponding to X206 is a polar or non-polar residue.

9. The engineered ketoreductase polypeptide of claim 1, in which the ketoreductase polypeptide amino acid sequence further comprises the following substitutions:
the residue corresponding to X7 is a non-polar, polar, or constrained residue;
the residue corresponding to X94 is a polar, basic, aliphatic, or non-polar residue;
the residue corresponding to X108 is a basic, constrained, or aromatic residue;
the residue corresponding to X117 is a non-polar or polar residue; and
the residue corresponding to X206 is a polar or non-polar residue.

10. The engineered ketoreductase polypeptide of claim 1, in which the ketoreductase polypeptide amino acid sequence further comprises at least one of the following substitutions:

the residue corresponding to X7 is a non-polar, polar, or constrained residue;

the residue corresponding to X96 is a constrained, aliphatic, non-polar, acidic, or polar residue;

the residue corresponding to X108 is a basic, constrained, or aromatic residue;

the residue corresponding to X117 is a non-polar or polar residue; and the residue corresponding to X206 is a polar or non-polar residue.

11. The engineered ketoreductase polypeptide of claim 1, in which the ketoreductase polypeptide amino acid sequence further comprises at least one of the following substitutions:

the residue corresponding to X7 is a non-polar, polar, or constrained residue;

the residue corresponding to X94 is a polar, basic, aliphatic, or non-polar residue;

the residue corresponding to X96 is a constrained, aliphatic, non-polar, acidic, or polar residue;

the residue corresponding to X108 is a basic, constrained, or aromatic residue;

the residue corresponding to X117 is a non-polar or polar residue; and the residue corresponding to X206 is a polar or non-polar residue.

12. The engineered ketoreductase polypeptide of claim 1, in which the ketoreductase polypeptide amino acid sequence further comprises the following substitutions:

the residue corresponding to X117 is a non-polar or polar residue;

the residue corresponding to X173 is an acidic or non-polar residue; and the residue corresponding to X206 is a polar or non-polar residue.

13. The engineered ketoreductase polypeptide of claim 1, in which the ketoreductase polypeptide amino acid sequence further comprises the following substitutions:

the residue corresponding to X7 is a non-polar, polar, or constrained residue;

the residue corresponding to X117 is a non-polar or polar residue;

the residue corresponding to X173 is an acidic or non-polar residue; and the residue corresponding to X206 is a polar or non-polar residue.

14. The engineered ketoreductase polypeptide of claim 1, in which the ketoreductase polypeptide amino acid sequence further comprises the following substitutions:

the residue corresponding to X7 is a non-polar, polar, or constrained residue;

the residue corresponding to X94 is a polar, basic, aliphatic, or non-polar residue;

the residue corresponding to X117 is a non-polar or polar residue;

the residue corresponding to X173 is an acidic or non-polar residue; and the residue corresponding to X206 is a polar or non-polar residue.

15. The engineered ketoreductase polypeptide of claim 1, in which the ketoreductase polypeptide amino acid sequence further comprises at least one of the following substitutions:

the residue corresponding to X7 is a non-polar, polar, or constrained residue;

the residue corresponding to X96 is a constrained, aliphatic, non-polar, acidic, or polar residue;

the residue corresponding to X117 is a non-polar or polar residue;

the residue corresponding to X173 is an acidic or non-polar residue; and the residue corresponding to X206 is a polar or non-polar residue.

16. The engineered ketoreductase polypeptide of claim 1, in which the ketoreductase polypeptide amino acid sequence further comprises at least one of the following substitutions:

the residue corresponding to X7 is a non-polar, polar, or constrained residue;

the residue corresponding to X94 is a polar, basic, aliphatic, or non-polar residue;

the residue corresponding to X96 is a constrained, aliphatic, non-polar, acidic, or polar residue;

the residue corresponding to X117 is a non-polar or polar residue;

the residue corresponding to X173 is an acidic or non-polar residue;

the residue corresponding to X206 is a polar or non-polar residue.

17. The engineered ketoreductase polypeptide of claim 1, wherein the percent stereomeric excess is at least 90%.

18. A method for stereoselectively reducing substrate 3-ketothiolane to product (R)-3-hydroxythiolane, which comprises contacting the 3-ketothiolane with the engineered ketoreductase polypeptide of claim 1, under reaction conditions suitable for reducing or converting the 3-ketothiolane to the(R)-3-hydroxythiolane.

19. The method of claim 18, wherein 3-ketothiolane is reduced to (R)-3-hydroxythiolane with at least 70% stereomeric excess.

* * * * *